US008092397B2

(12) United States Patent
Wallace et al.

(10) Patent No.: US 8,092,397 B2
(45) Date of Patent: Jan. 10, 2012

(54) APPARATUS FOR MEASURING DISTAL FORCES ON A WORKING INSTRUMENT

(75) Inventors: Daniel T. Wallace, Burlingame, CA (US); Gregory Stahler, San Jose, CA (US); Alex Goldenberg, San Francisco, CA (US); Gene Reis, San Jose, CA (US); Robert G. Younge, Portola Valley, CA (US); Mathew Clopp, Santa Clara, CA (US); David B. Camarillo, Stanford, CA (US); Toby St. John King, Warshash (GB)

(73) Assignee: Hansen Medical, Inc., Mountain View, CA (US)

( * ) Notice: Subject to any disclaimer, the term of this patent is extended or adjusted under 35 U.S.C. 154(b) by 1093 days.

(21) Appl. No.: 11/678,001

(22) Filed: Feb. 22, 2007

(65) Prior Publication Data
US 2007/0233044 A1    Oct. 4, 2007

Related U.S. Application Data

(60) Provisional application No. 60/776,065, filed on Feb. 22, 2006, provisional application No. 60/801,355, filed on May 17, 2006.

(51) Int. Cl.
*A61B 5/103* (2006.01)
*A61B 5/117* (2006.01)
*A61M 25/00* (2006.01)

(52) U.S. Cl. ......................... 600/587; 600/585

(58) Field of Classification Search .................. 600/587, 600/585, 550, 561, 595; 901/1–50
See application file for complete search history.

(56) References Cited

U.S. PATENT DOCUMENTS

| 5,003,982 | A | 4/1991 | Halperin |
| 5,060,632 | A | 10/1991 | Hibino et al. |
| 5,067,346 | A | 11/1991 | Field |
| 5,433,215 | A | 7/1995 | Athanasiou et al. |
| 5,524,635 | A | 6/1996 | Uflacker et al. |

(Continued)

FOREIGN PATENT DOCUMENTS
EP        1285634        2/2003
(Continued)

OTHER PUBLICATIONS

PCT International Search Report forms PCT ISA 220 and 210, mailed Jul. 12, 2007, for PCT/US2007/062617, Applicant Hansen Medical Inc. (6 pages).

(Continued)

*Primary Examiner* — Jeffrey G Hoekstra
(74) *Attorney, Agent, or Firm* — Vista IP Law Group LLP

(57) ABSTRACT

A robotic catheter manipulator includes a guide catheter including proximal and distal ends and lumen extending there through. A flexible bellows is secured at one end to the proximal end of the guide catheter and at the other end to a seal configured to receive a working catheter. In a loaded state, the working catheter is fixed relative to the seal. A ditherer is operatively connected to the seal for dithering the working catheter relative to the guide catheter when placed therein. The robotic catheter manipulator includes at least one force sensor for measuring the force applied to the working catheter by the ditherer. Force measurements may be translated into an estimated force that is experienced at the distal end of the working catheter which may then be displayed to the physician via a monitor or display.

36 Claims, 44 Drawing Sheets

U.S. PATENT DOCUMENTS

| | | | |
|---|---|---|---|
| 5,810,716 | A | 9/1998 | Mukherjee et al. |
| 5,911,694 | A | 6/1999 | Ikeda et al. |
| 6,068,604 | A | 5/2000 | Krause et al. |
| 6,102,850 | A | 8/2000 | Wang et al. |
| 6,126,651 | A | 10/2000 | Mayer |
| 6,565,554 | B1 | 5/2003 | Niemeyer |
| 6,786,896 | B1 | 9/2004 | Madhani |
| 2002/0133174 | A1 | 9/2002 | Charles et al. |
| 2003/0055360 | A1 | 3/2003 | Zeleznik et al. |
| 2003/0060927 | A1 | 3/2003 | Gerbi et al. |
| 2005/0085728 | A1 | 4/2005 | Fukuda |
| 2006/0161045 | A1 | 7/2006 | Merril et al. |
| 2006/0293864 | A1 | 12/2006 | Soss |
| 2007/0043338 | A1 | 2/2007 | Moll et al. |
| 2007/0156123 | A1 | 7/2007 | Moll et al. |
| 2007/0197896 | A1 | 8/2007 | Moll et al. |
| 2007/0197939 | A1 | 8/2007 | Wallace et al. |

FOREIGN PATENT DOCUMENTS

| | | |
|---|---|---|
| GB | 2102590 | 2/1983 |
| WO | 2004104714 | 12/2004 |

OTHER PUBLICATIONS

PCT Written Opinion of the International Searching Authority form PCT/ISA/237, mailed Jul. 12, 2007, for PCT/ US2007/062617, Applicant Hansen Medical Inc. (6 pages).

Non-Final office action for related U.S. Appl. No. 11/678,016, mailed Aug. 31, 2010. (30 pages).

PCT International Preliminary Report on Patentability for PCT/US2007/062617, Applicant Hansen Medical, Inc., Forms PCT/IB/326, 373, and PCT/ISA/237 dated Feb. 22, 2006. (8 pages).

Office Action from related Chinese patent application No. 200780006359.8, Applicant Hansen Medical, Inc., mailed Aug. 9, 2010, in Chinese language with translation provided by Chinese associate. (6 pages).

Office Action from related European patent application No. 07757358.2, Applicant Hansen Medical, Inc., Forms EPO 2001 and 2906, mailed Dec. 9, 2008. (3 pages).

Amendment Response to Non-Final office action for related application U.S. Appl. No. 11/678,016, mailed Aug. 31, 2010, response submitted on Dec. 27, 2010. (21 pages).

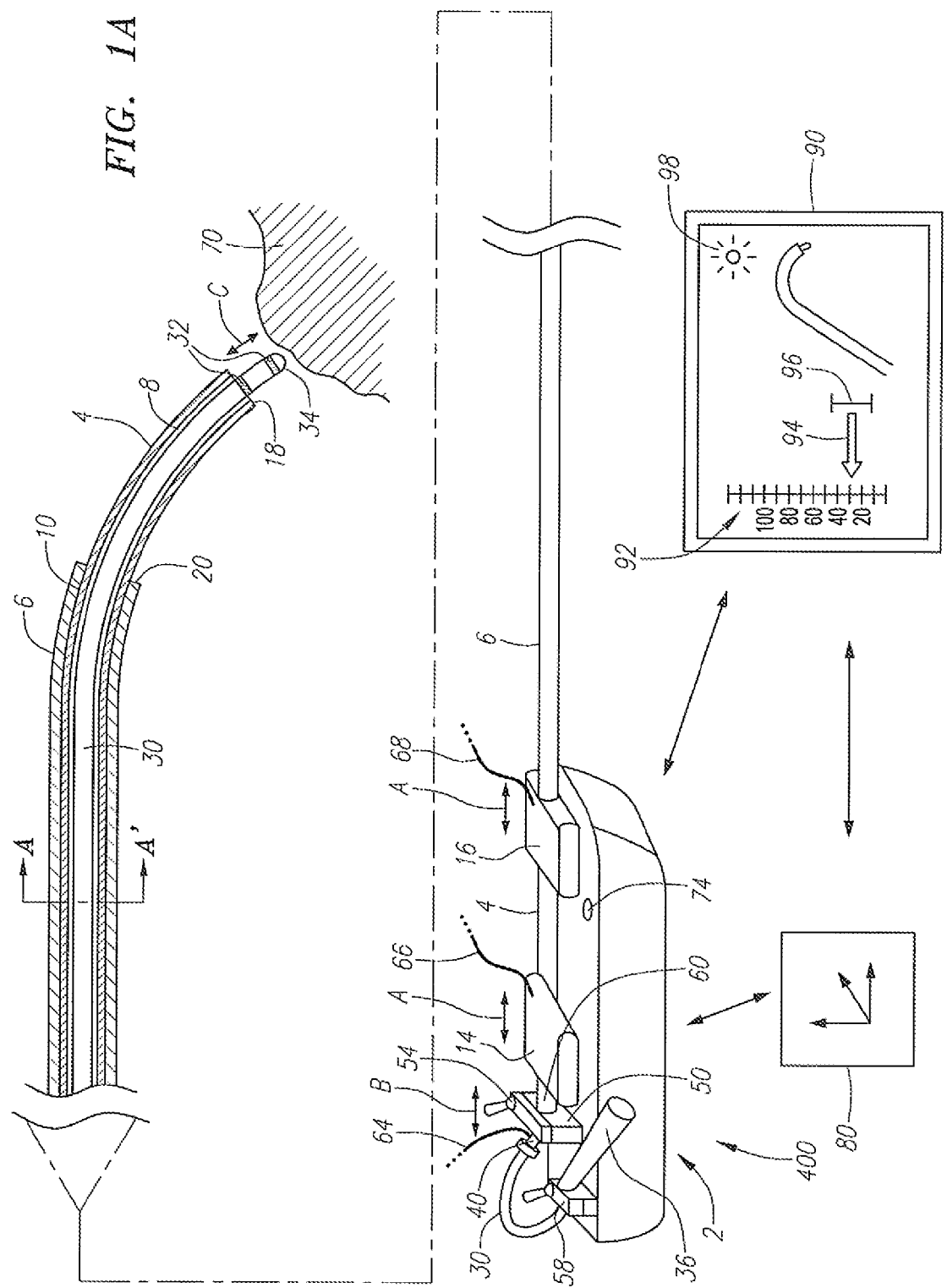

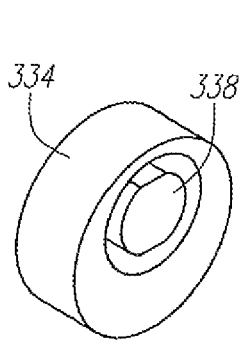
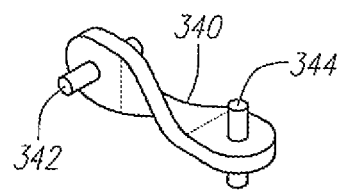
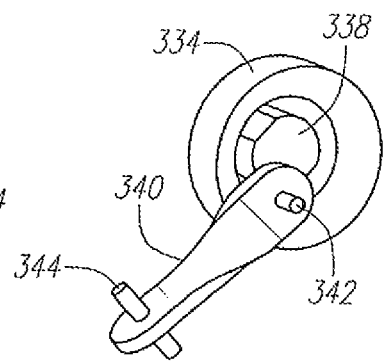
FIG. 33C    FIG. 33D    FIG. 33E
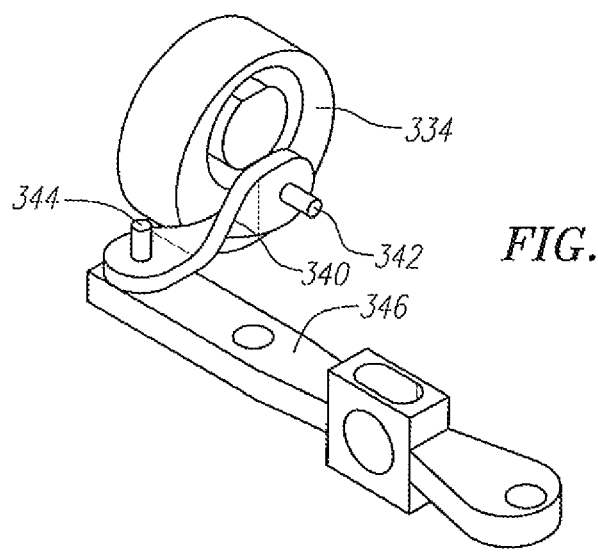
FIG. 33F
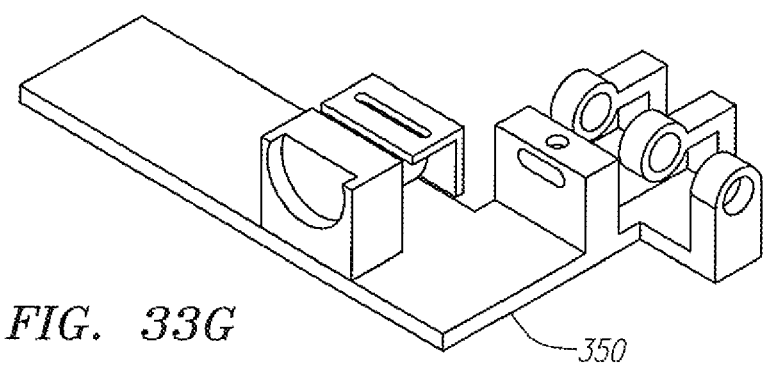
FIG. 33G

APPARATUS FOR MEASURING DISTAL FORCES ON A WORKING INSTRUMENT

REFERENCE TO RELATED APPLICATIONS

The present application claims the benefit under 35 U.S.C. §119 to U.S. Provisional Patent Application Ser. Nos. 60/776,065, filed on Feb. 22, 2006, and 60/801,355, filed on May 17, 2006. The foregoing applications are all incorporated by reference into the present application in their entirety for all purposes.

FIELD OF THE INVENTION

The invention relates generally to minimally-invasive instruments and systems, such as manually or robotically steerable catheter systems, and more particularly to steerable catheter systems for performing minimally invasive diagnostic and therapeutic procedures. More particularly, the invention pertains to devices and methods that are capable of measuring or sensing forces experienced by a medical instrument when in contact with surrounding objects such as tissue structures.

BACKGROUND

Currently known minimally invasive procedures for the treatment of cardiac and other disease conditions use manually or robotically actuated instruments which may be inserted transcutaneously into body spaces such as the thorax or peritoneum, transcutaneously or percutaneously into lumens such as the blood vessels, through natural orifices and/or lumens such as the mouth and/or upper gastrointestinal tract, etc. For example, many conventional minimally-invasive cardiac diagnostic and/or interventional techniques involve accessing the right atrium of the heart percutaneously with a catheter or catheter system by way of the inferior vena cava. When controlling an elongate instrument, such as a catheter, in any one of these applications, the physician operator can push on the proximal end of the catheter and attempt to feel the distal end make contact with pertinent tissue structures, such as the walls of the heart. Some experienced physicians attempt to determine or gauge the approximate force being applied to the distal end of a catheter due to contact with tissue structures or other objects, such as other instruments, prostheses, or the like, by interpreting the loads they tactically sense at the proximal end of the inserted catheter with their fingers and/or hands. Such an estimation of the force, however, is quite challenging and somewhat imprecise given the generally compliant nature of many minimally-invasive instruments, associated frictional loads, dynamic positioning of the instrument versus nearby tissue structures, and other factors.

Manually and robotically-navigated interventional systems and devices, such as steerable catheters, are well suited for performing a variety of minimally invasive procedures. Manually-navigated catheters generally have one or more handles extending from their proximal end with which the operator may steer the pertinent instrument. Robotically-navigated catheters may have a proximal interface configured to interface with a catheter driver comprising, for example, one or more motors configured to induce navigation of the elongate portion of the instrument in response to computer-based automation commands, commands input by the operator at a master input device, combinations thereof, or the like. Regardless of the manual or electromechanical nature of the driving mechanism for a diagnostic or interventional instrument, the operator performing the procedure would prefer to have accurate, timely information regarding the forces experienced at the distal portion of the working instrument. There thus is a need for an improved force-sensing technology to facilitate the execution of minimally-invasive interventional procedures. It is desirable to have the capability to accurately monitor the loads applied by or to the subject medical instrument or device from adjacent tissues and other objects.

SUMMARY

In one embodiment of the invention, a robotic catheter manipulator includes a robotically operated guide catheter including proximal and distal ends and lumen extending there through. A flexible bellows is secured at one end to the proximal end of the guide catheter and at the other end to a seal configured to receive a working catheter. For example, the seal may include a Touhy seal. A ditherer is operatively connected to the seal for dithering the working catheter relative to the guide catheter when placed therein. The robotic catheter manipulator includes at least one force sensor for measuring the force applied to the working catheter by the ditherer.

In another embodiment, the ditherer includes a reciprocating dither carriage containing a pivotable load bearing member that can swing back-and-forth as the dither carriage is dithered. Opposing load cells are positioned on either side of the pivotable load bearing member with each load cell containing a force sensor that measures compression forces when in contact with the pivotable load bearing member. The pivotable load bearing member may be mounted to the working catheter either directly or through a seal such as the Touhy seal. Force measurements throughout one or more dither cycles are then subject to data processing which determines the estimated force at the distal end of the working catheter. The data processing may include a comparison of the waveform or force profile taken during an insertion/withdrawal cycle when the distal end is subject to a force and the waveform or force profile of a baseline measurement obtained when the distal end is not subject to any external force.

In still another embodiment, an apparatus for sensing the forces applied to the distal end of a robotically controlled working catheter includes a robotically controlled guide catheter that is configured for insertion into a body lumen of a patient. The body lumen may include, for example, a blood vessel or a chamber within the heart. The guide catheter includes a lumen extending from a proximal end to a distal end dimensioned to receive a working catheter. The working catheter includes a distal end that projects distally from the distal end of the robotically controlled guide catheter and a proximal end that extends proximally from the robotically controlled guide catheter. A ditherer is operatively connected to the proximal region of the working catheter for dithering the working catheter relative to the guide catheter. The ditherer may be directly coupled to the working catheter or indirection through some other component such as, for example, a seal. The apparatus includes at least one force sensor for measuring the force applied to the working catheter by the ditherer.

In still another embodiment, a system for monitoring the estimated force experienced by a distal end of a working catheter includes a guide catheter mounted to a robotic catheter manipulator, the guide catheter including a lumen therein adapted to receive the working catheter. A reciprocating ditherer is disposed on the robotic catheter manipulator, the reciprocating ditherer being operatively connected to a proximal region of the working catheter so as to dither the working catheter with respect to the guide catheter. First and second force sensors are provided for measuring forces applied to the working catheter during insertion and withdrawal, respectively. The system includes a processor or multiple processors for calculating the estimated force on the distal end of the working catheter based at least in part on the measured forces obtained by the first and second force sensors. For instance, the processor(s) may calculate average force values during the insertion and withdrawal strokes when the distal end of the working catheter is in contact with a surface or object and compares this to average force values obtained in a baseline measurement where the distal end of the working catheter is free. The comparison may include, for example, a subtraction process to eliminate substantially all force components acting on the system except for the force at the distal end of the working catheter.

Any number of types of working catheters may be used in connection with the system. These include by way of illustration and not limitation, ablation catheters, dilating catheters, and electrophysiology catheters.

BRIEF DESCRIPTION OF THE DRAWINGS

FIG. 1A schematically illustrates a system for measuring forces on a distal end of a working instrument that is manipulated by a robotic instrument system.

FIG. 33C illustrates a cam having a slot therein.

FIG. 33D illustrates a linkage having pins on opposing ends.

FIG. 33E illustrates the linkage of FIG. 33D in mating arrangement with the cam of FIG. 33C.

FIG. 33F illustrates a pivot holder connected to the linkage of FIG. 33E.

FIG. 33G illustrates a base used to hold the components of the ditherer illustrated in FIGS. 33A and 33B.

FIGS. 34A-34D illustrate various embodiments in which the estimated force and estimated error are presented to a physician via a monitor, display or the like.

DETAILED DESCRIPTION

Figure 1B:
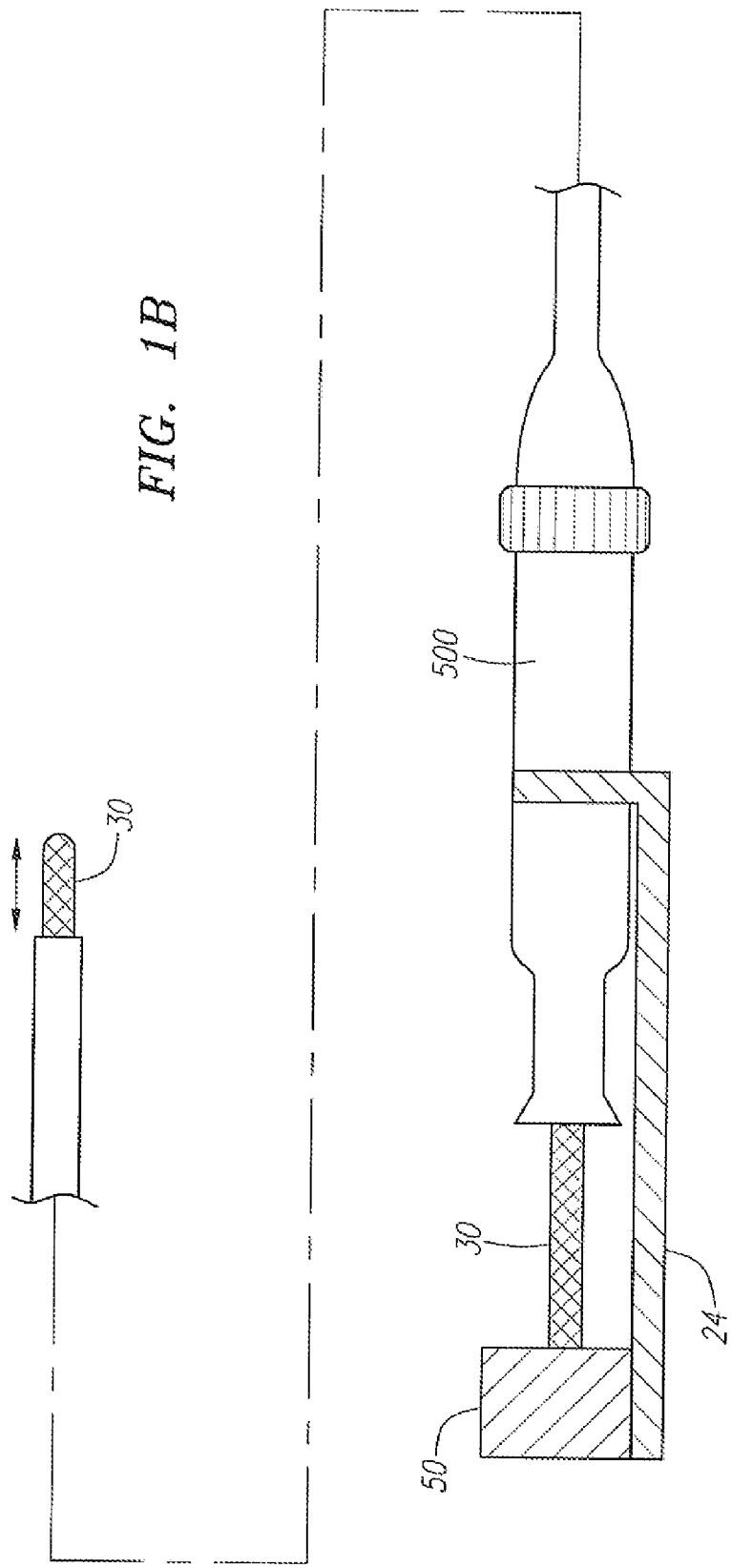
FIG. 1B illustrates a ditherer coupled to a manually operated, steerable guide catheter and a working instrument.

FIG. 1A illustrates a schematic, top-level view of a robotic instrument system 2 according to one embodiment. FIGS. 1B-1F illustrate various other embodiments of a system 2 that may utilize a mechanical ditherer 50 or other dithering mechanism or device as described herein. For example, FIG. 1B illustrates a manually-operated, steerable guide catheter 500 that is mounted via a base 24 containing a ditherer 50. The ditherer 50 is coupled to a working instrument 30 that is dithered back-and-forth relative to the guide catheter 500. The working instrument 30 may include any number generally elongate members that are typically used during medical diagnostic or therapeutic procedures. For example, the working instrument 30 may include by way of illustration and not limitation, a catheter, guide wire, imaging element, laser fiber or bundle of fibers, tool, or other instrument.

Figure 1C:
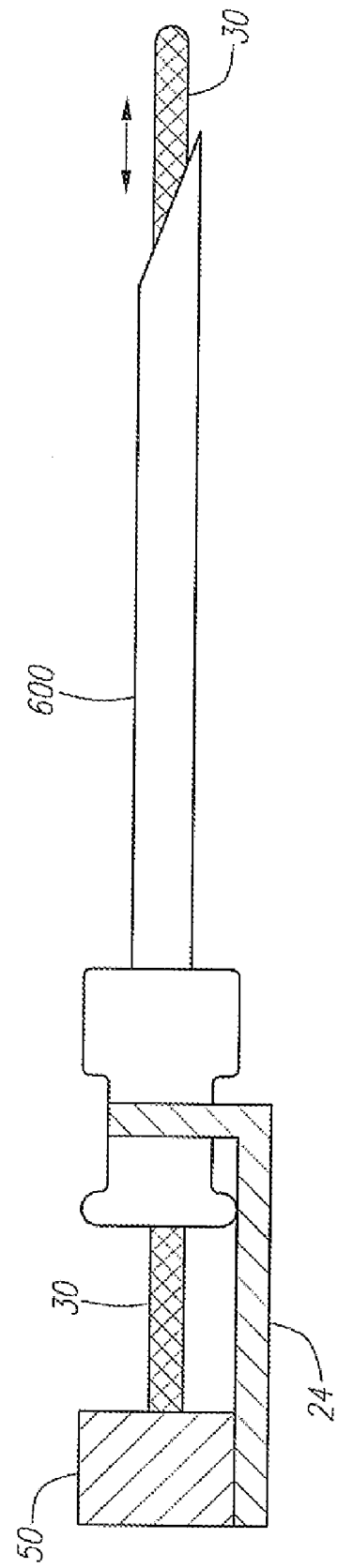
FIG. 1C illustrates a ditherer coupled to a rigid member such as a trocar and a working instrument.

FIG. 1C illustrates a ditherer 50 used in conjunction with a relatively rigid elongate member such as, for example, a trocar 600. The ditherer 50 is coupled to a working instrument 30 that is dithered in a reciprocating fashion through a lumen (not shown) contained in the trocar 600. As in the prior embodiment, a base 24 is used to secure the ditherer 50 relative to the trocar 600.

Figure 1D:
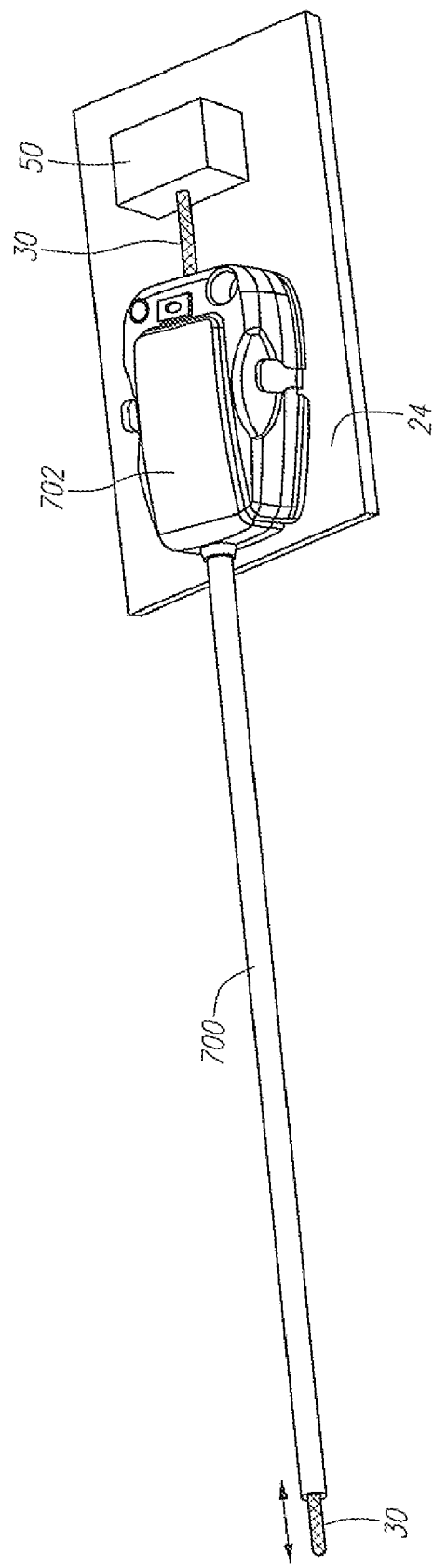
FIG. 1D illustrates a robotically manipulated rigid or semi-rigid tool that includes a ditherer for reciprocating a working instrument therein for determining the force experienced at the distal end of the working instrument.

FIG. 1D illustrates still another embodiment in which the ditherer 50 is coupled to a working instrument 30 that is passed through a tool 700 which may include a rigid or semi-rigid shaft having one or more lumens therein adapted to receive a working instrument 30. The tool 700 may be coupled to a housing 702 that mechanically and electrically couples the tool 700 to a robotically-controlled manipulator. For example, the tool 70 may be coupled to a robotically controlled instrument driver such as, for instance, the DA VINCI surgical system sold by Intuitive Surgical, Inc. of Sunnyvale, Calif.

Figure 1E:
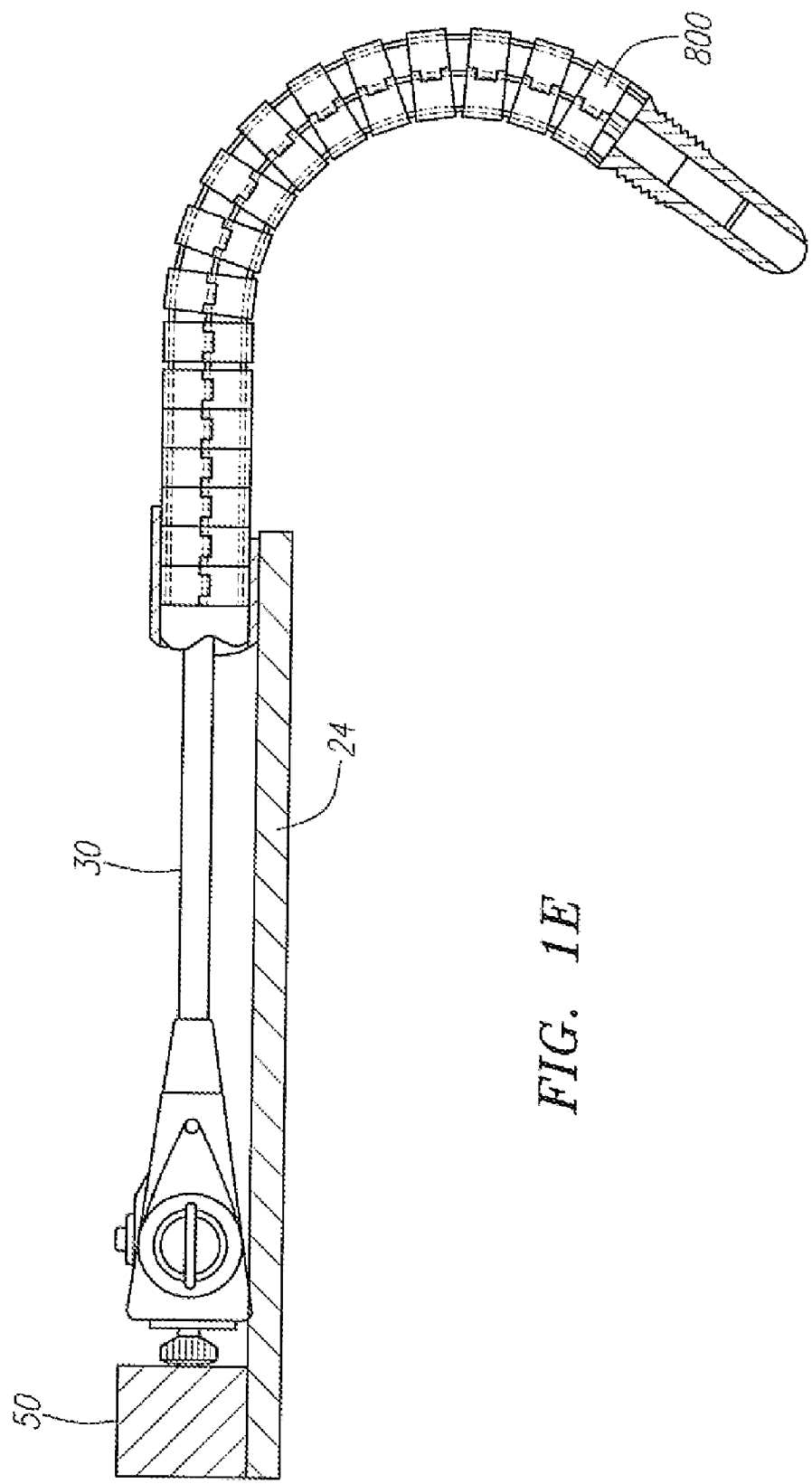
FIG. 1E illustrates a ditherer that is used to move a working instrument back-and-forth within an outer flexible scope or elongate member.
Figure 1F:
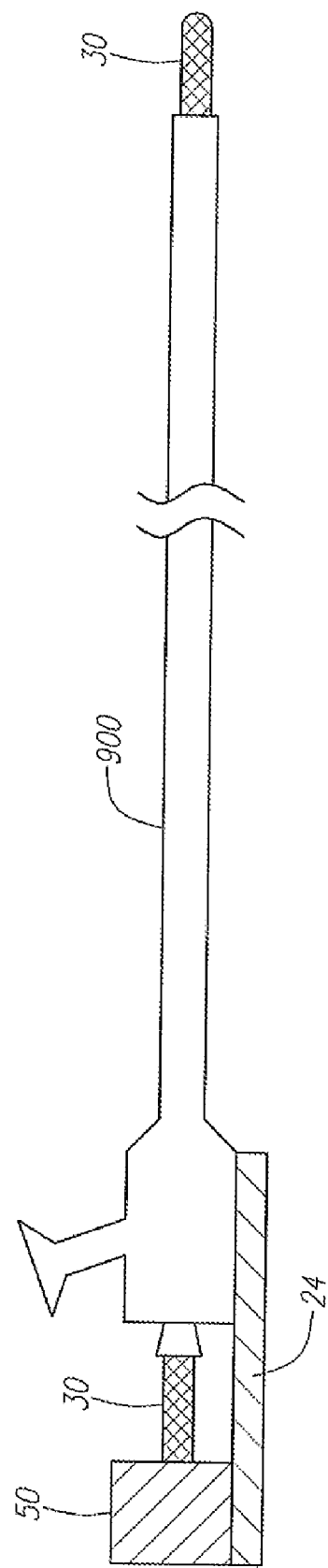
FIG. 1F illustrates a ditherer that is used to move a working instrument such as a guide wire that is disposed within an elongate imaging tool such as an endoscope.

FIG. 1E illustrates an embodiment in which a working instrument 30 such as an endoscope is coupled to the ditherer 50. The working instrument 30 can thus be moved relative to an outer flexible member such as a segmented, flexible scope 800 of the type developed by NeoGuide Systems, Inc. FIG. 1F illustrates still another embodiment in which, for example, the ditherer 50 is used in connection with visualization tool such as an endoscope 900. In this embodiment, the ditherer 30 is coupled to a working instrument 30 such as a guide wire that is dithered back-and-forth with respect to the endoscope 900. The endoscope 900 may be rigid, flexible, or semi-rigid.

Referring back to FIG. 1A, the depicted robotic instrument system 2, variations of which are described in further detail, for example, in U.S. Utility patent application Ser. Nos. 11/640,099 filed on Dec. 14, 2006, 11/637,951 filed on Dec. 11, 2006, and 11/481,433 filed on Jul. 3, 2006, which are incorporated by reference herein in their entirety, comprises a robotically-steerable guide instrument 4 and an outer sheath instrument 6 which may also be robotically-steerable. For illustrative purposes, a system comprising both a flexible robotic guide instrument 4 and a flexible robotic sheath instrument 6, each of which may also be termed a variation of a steerable "catheter", as described in the aforementioned applications which are incorporated by reference, is depicted, although variations comprising only a flexible robotic guide instrument 4 or only a flexible robotic sheath instrument 6, as accompanied by a flexible working instrument 30 as described below, may be desired. Further, the dithering-based force sensing technologies described herein may be utilized with non-steerable and/or non-flexible or semi-flexible instrument set configurations (for example, to sense forces at the distal end of a working instrument advanced through a straight or bent, rigid, flexible, or semi-flexible steerable or nonsteerable trocar, or other straight or bent, rigid, flexible, or semi-flexible, steerable or nonsteerable minimally invasive instrument defining a working lumen in which a working instrument may be moved in an oscillatory fashion—such as the robotic instruments available from manufacturers such as NeoGuide Systems, Inc., Stereotaxis Inc., and Intuitive Surgical, Inc.). Furthermore, the dithering-based force sensing technologies described herein may be utilized in other applications with non-slender, or non-minimally-invasive, instruments, so long as such instruments define a lumen through which a working instrument may be moved in an oscillatory fashion and detected, as described below.

Figure 2:
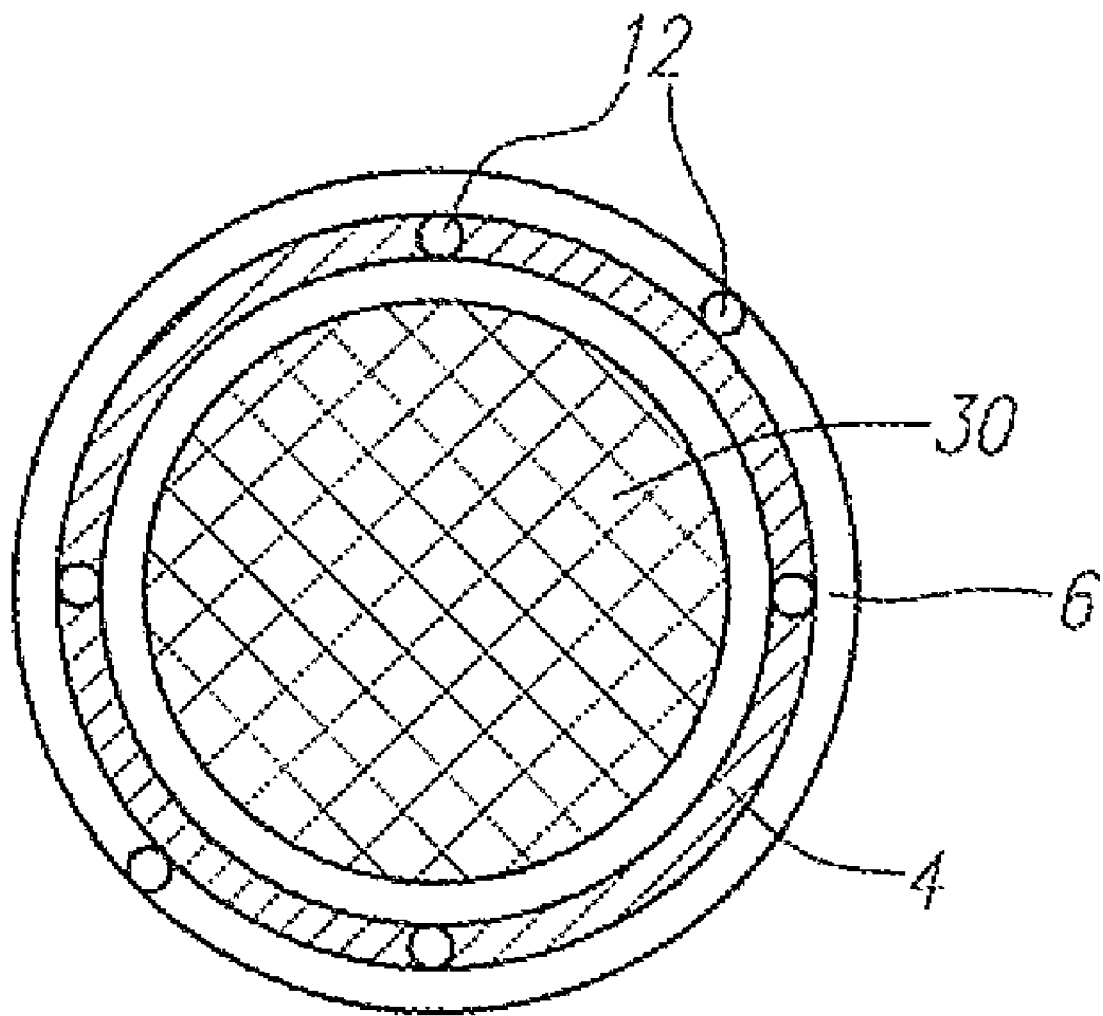
FIG. 2 illustrates a cross-sectional view of the guide instrument, sheath, and working instrument taken along the line A-A' of FIG. 1A.

In the depicted embodiment of FIG. 1A, robotic steering actuation is provided to the sheath and guide instruments in the depicted embodiment by a robotic instrument driver 400. Both the guide instrument 4 and sheath instrument 6 define respective lumens 8, 10, and in the depicted configuration, the sheath instrument 6 coaxially surrounds a portion of the guide instrument 4. The robotically-steerable guide instrument 4 and sheath instrument 6 comprise a number of control members 12, as shown in the cross-sectional view of FIG. 2, that may be used to steer the guide instrument 4 and/or sheath instrument 4 using actuations from the robotic instrument driver 400.

The control members 12 may comprise wires or the like that are selectively tensioned via respective proximal instrument portions or "splayers" 14, 16 that are configured to be interfaced with the robotic instrument driver 400 to provide steering actuation to the guide instrument 4 and sheath instrument 6, along with insertion or retraction along the longitudinal axis of the proximal lumen defined by the guide instrument 4 or sheath instrument 6 via motors within the instrument driver 400 which are configured to insert and retract the splayers 14, 16 independently relative to each other and relative to the outer structure of the instrument driver 400 and/or relative to the operating table. For example, the guide splayer 14 and sheath splayer 16 may comprise a plurality of motor-driven, rotating spools or drums (not shown) that can selectively tension or release the control members 12 of the pertinent instrument to provide controlled steering to the guide instrument 4 and/or sheath instrument 6. As described above, the splayers 14, 16 may also move longitudinally ("insertion" or "retraction") with respect to the robotic instrument driver 400 main structure as illustrated with arrows "A" in FIG. 1A.

As seen in the embodiment depicted in FIG. 1A, the guide instrument 4 passes through the lumen 10 of the sheath instrument 6 and is thus moveable with respect thereto. As seen in the top detail of FIG. 1A, the distal end 18 of the guide instrument 4 projects distally with respect to the distal end 20 of the sheath instrument 6. Of course, in other aspects, the guide instrument 4 may be withdrawn proximally such that the distal end 18 is substantially flush with the distal end 20 of the sheath instrument 6, or withdrawn proximally even further such that the distal end 18 is hidden within the distal end 20 of the sheath instrument. The contact surfaces between the guide instrument 4 and the outer sheath instrument 6 may be coated with a lubricous coating such as, for example, PTFE to reduced frictional forces there between.

Moreover, as explained in more detail below, an optional flushing fluid may be pumped or forcibly moved between the guide instrument 4 and outer sheath instrument 6. The flushing fluid may act as a lubricant in addition to preventing retrograde flow of blood and other biological material into the space between the guide instrument 4 and outer sheath instrument 6.

Still referring to FIG. 1A, a working instrument 30 is shown being secured to the robotic instrument driver 400. The working instrument 30 may comprise any number of types of instruments, including but not limited to guidewires, probes, laser fibers, injection devices, surgical tools, and catheters, such as electrophysiology catheters, ablation catheters, and the like. FIG. 1A illustrates an ablation catheter as the working instrument 30 with electrodes 32 positioned at a distal end 34 of the ablation catheter. The working instrument 30, or "working catheter" in this instance, may be custom designed for use with the robotic instrument system 2 or, alternatively, the working instrument 30 or working catheter may comprise an off-the-shelf catheter such as those used by physicians in conventional, manually-navigated procedures. The working instrument 30 is loaded into the robotic instrument system 2 by passing the distal end 34 through a seal 40. The seal 40 may comprise a "Touhy" that has a small hole or opening through which the working instrument 30 passes. The Touhy seal 40 may have an elongate or rigid body with a proximal end cap 44 (seen e.g., in FIGS. 13, 14, 16, and 17) or the like that is used to create a non-slip, fluid-tight seal between the Touhy 40 and the working instrument 30.

As seen in FIG. 1A, the Touhy seal 40 is secured to a mechanical "ditherer" 50 via a clamp 54. The mechanical ditherer 50 is a mechanical subsystem that moves in a reciprocating or oscillating motion in the direction of arrow B, and may be coupled to other structures, such as a working instrument, to induce oscillatory, reciprocating, or "dithering" motion in such other structures. The mechanical ditherer 50 is driven by a motor (not shown in FIG. 1A) which may be located on-board the robotic instrument driver 400 or, in other embodiments, off-board the robotic instrument driver 400 as a separate dithering actuation subsystem. In the depicted variation, the mechanical ditherer 50 dithers or causes reciprocating axial movement of the working instrument 30 relative to the guide instrument 4 and sheath instrument 6. For example, FIG. 1A illustrates the distal end 34 of the working instrument 30 dithering back and forth in the direction of arrow "C". The length or stroke of the dithering may be adjusted depending on the nature of the procedure but generally is less than a few millimeters. In some embodiments, the stroke of the dithering may be less than about 1.5 mm.

The mechanical ditherer 50 comprises at least one force sensor (not shown in FIG. 1A) that is used to detect the force or load that is being applied to the proximal portion of the working instrument 30. The force sensors are able to determine the insertion and withdrawal forces applied to the working instrument 30 via the mechanical ditherer 50. Over one or more dithering cycles, these force profiles or waveforms can be used to accurately estimate contact forces at the distal end 34 of the working instrument 30. For example, FIG. 1A shows the distal end 34 in close proximity to an anatomical surface 70 which may comprise, for instance, cardiac tissue. Of course, contact forces may also come from other objects in the vicinity of the distal end 34 such as, for instance, medical instruments or the like.

Still referring to FIG. 1A, a flexible bellows 60 connects the distal end of the Touhy seal 40 to the proximal end of the guide instrument 4. In this regard, the flexible bellows 60 compresses and expands as the working instrument 30 is dithered with respect to the guide instrument 4 and sheath instrument 6. The flexible bellows 60 may be connected to a fluid line 64 that is connected to a source of pressurized saline or the like. During use of the robotic instrument system 2, the pressurized saline is pumped into the space between the exterior of the working instrument 30 and the interior of the guide instrument 4 to prevent backflow of blood or other bodily fluids which, if allowed to retrograde into the guide instrument, could disrupt the ability to dither the working instrument 30 inside the guide instrument 4. Additional fluid lines 66, 68 may be coupled, respectively, to the guide instrument splayer 14 and sheath instrument splayer 16 to provide lubrication between guide instrument 4 and sheath instrument 6.

While FIG. 1A illustrates the mechanical ditherer 50 being coupled to the Touhy seal 40 it should be understood that the mechanical ditherer 50 also may be coupled directly to a proximal region of the working instrument 30. FIG. 1A also illustrates a second clamp 58 that is used to secure the handle 36 of the working instrument 30 to the robotic instrument driver 400. In this regard, inadvertent movement of the handle 36 does not affect the force sensing capabilities of the mechanical ditherer 50. The handle 36 is isolated or grounded from the load sensing aspect of the mechanical ditherer 50 which is discussed in more detail below.

By "dithering" the working instrument 30 with respect to the guide instrument 4, the repeated cyclic motion may be utilized to overcome frictional challenges normally complicating the measurement, from a proximal location, of loads at the distal end 34 of the working instrument 30 when in contact with a surface. In one embodiment, the dithering motion may be applied on a proximal region of the working instrument 30 as is illustrated in FIG. 1A and near the location at which relative axial load is measured. In other words, for example, if a user were to position a working instrument 30 down a lumen 8 of a guide instrument 4 so that the distal end 34 of the working instrument 30 is sticking out slightly beyond the distal end 18 of the guide instrument 4, and have both the guide instrument 4 and working instrument 30 threaded through the blood vessel(s) from a femoral location to the chambers of the heart, it may be difficult to sense contact(s) and force(s) applied to the distal end 34 of the working instrument 30 due to the complications of the physical relationship with the associated guide instrument 4. In particular, in a steady state wherein there is little or no relative axial or rotational motion between the working instrument 30 and guide instrument 4, the static coefficient of friction is applicable, and there are relatively large frictional forces keeping the working instrument 30 in place adjacent to the guide instrument 4 (no relative movement between the two).

To release this relatively tight coupling and facilitate proximal measurement of forces applied to the distal end 34 of the working instrument 30, dithering motion may be used to effectively break loose this frictional coupling. In one embodiment, such as the one illustrated in FIG. 1A, the dithering motion may be applied on a proximal region of the working instrument 30. In still other embodiments (not shown), it may be possible to dither the guide instrument 4 with respect to a stationary or substantially stationary working instrument 30. In yet another embodiment, both the guide instrument 4 and working instrument 30 may be dithered with respect to one another.

It should also be understood that FIG. 1A illustrates longitudinal dithering of the working instrument 30 with respect to the guide instrument 4. It is possible in alternative embodiments to dither the working instrument 30 radially with respect to the guide instrument 4. Alternatively, the guide instrument 4 could be dithered radially with respect to the working instrument 30. In yet another alternative, the guide instrument 4 and working instrument 30 could both be dithered in the radial direction at the same time.

The dithering embodiment illustrated in FIG. 1A avoids some of the complexities associated with using custom-made working instruments having embedded, distally-located sensors and instead facilitates the use of standard off-the-shelf working instruments 30. Thus, without altering the working instrument 30, by dithering the proximal region of the working instrument 30, either directly or via the seal 40, and placing the force sensors at the proximal region of the working instrument 30 it is possible to measure the estimated force that is applied at the distal end 34 of the working instrument 30. By dithering the working instrument 30, the same is in motion substantially all of the time, and applied forces are shown in the force readings as incremental forces, thus substantially eliminating the effects of static friction after data processing has been executed, which is described in more detail below.

Still referring to FIG. 1A, the robotic instrument system 2 may comprise an all stop button 74 that is used to terminate activity of the robotic instrument driver 400 when depressed. The button 74 thus acts as a safety feature should one or more aspects of the device fail requiring manual user intervention.

FIG. 1A also illustrates a user interface 80 that is operatively connected to the robotic instrument driver 400 and instrument set. The physician or other user interacts with the user interface 80 to operate the robotic instrument driver 400 and associated guide 4 and/or sheath 6 instruments, and associated working instrument 30. The user interface 80 may be connected to the robotic instrument driver 400 via a cable or the like. Alternatively, the user interface 80 may be located in a geographically remote location and communication is accomplished, at least in part, over a wide area network such as the Internet. Of course the user interface 80 may also be connected to the robotic instrument driver 400 via a local area network or even wireless network that is not located at a geographically remote location.

FIG. 1A also illustrates a display 90 that is used to display various aspects of the robotic instrument system 2. For example, an image of the guide instrument 4, sheath instrument 6, and working instrument 30 may be displayed in real time on the display 90 to provide the physician with the current orientation of the various devices as they are positioned, for example, within a body lumen or region of interest. As also shown in FIG. 1A, the display 90 may include a readout on the estimated force experienced by the distal end 34 of the working instrument 30. For example, the readout may include graded scale 92 with a moveable arrow 94 that rises or falls as the force changes. The display 90 may also include a visual cue 96 indicating the amount of error associated with the estimated force. The visual cue 96 may include error bars as shown in FIG. 1A. Alternatively, the visual cue 96 may include a separate scale or graph that illustrates real time error in the measured force. The visual cue 96 may also include a color change to the arrow 94. In still another alternative, the visual cue or graphical element 96 may include a warning indicator or textual message.

In addition, the display 90 may include a visual cue or signal that is present when the error exceeds a pre-determined threshold value (e.g., +/−20% or +/−20 grams). The estimated measured force at the distal end 34 of the working instrument 30 may also be compared with a pre-determined threshold value. For example, if too much pressure is being applied to the distal end 34, an audible warning signal may be initiated. Alternatively, a visual signal such as a graphical element 98 may be shown on the display 90. In still another aspect, a haptic signal may be returned to the user, for example, a vibrational signal that can be felt by the user.

Figure 3:
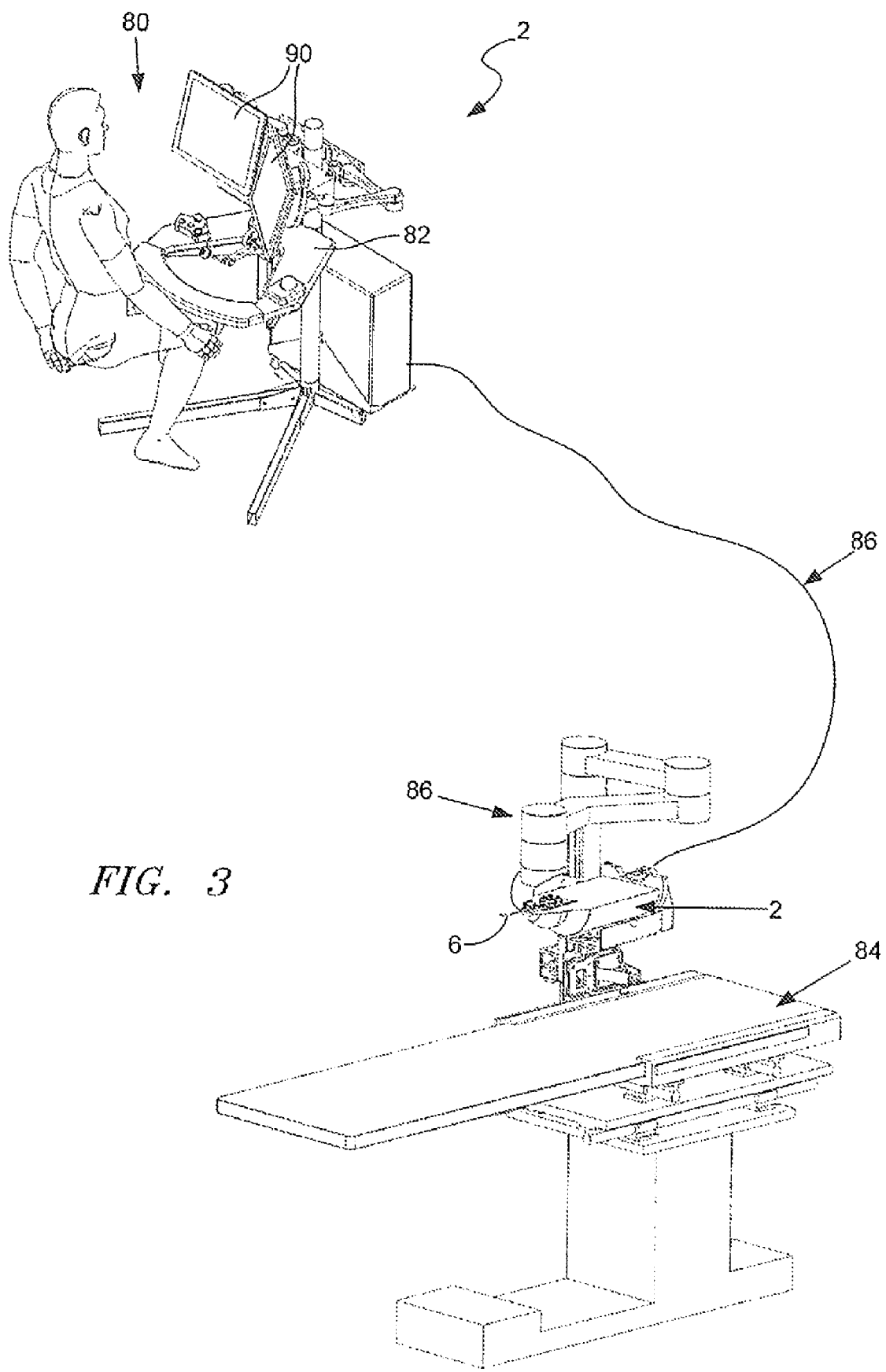
FIG. 3 illustrates a physician or other using stationed at an operator control station that is operatively connected to a robotic instrument system according to one aspect of the invention.

FIG. 3 illustrates a user interface 80 located at an operator control station 82 located remotely from an operating table 84 having a movable support-arm assembly 86. The support assembly 86 is configured to movably support the robotic instrument driver 400 above the operating table 84 in order to position the guide instrument 4, sheath instrument 6, and working instrument 30 (not shown in FIG. 3). A communication link 86 transfers signals between the operator control station 82 and the robotic instrument driver 400.

Figure 4:
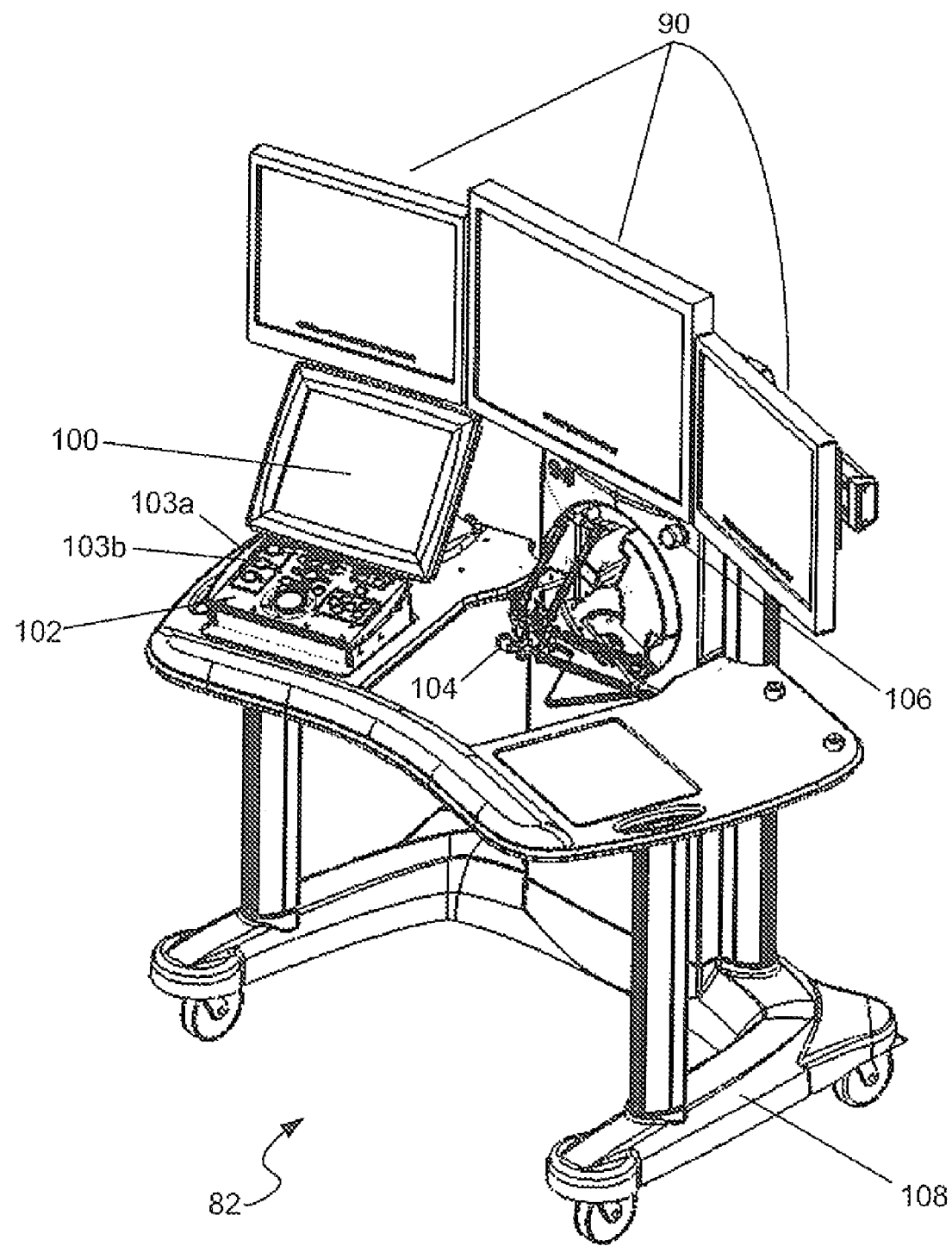
FIG. 4 illustrates a perspective view of an operator control station and associated cart.

Referring now to FIG. 4, a view of another variation of an operator control station 82 is depicted having three displays 90, a touch screen user interface 100, and a control button console 102. The control button console 102 may comprise a button 103a that is used to turn the force sensing capability on or off. In addition, the control button console 102 may comprise a dedicated button 103b that is used to baseline the robotic instrument driver 400 or associated instrument set. Of course, these functions may be implemented instead via the touch screen user interface 100. The operator control station 82 comprises master input device 104 that is manipulated by the physician to translate movement to the robotic instrument driver 400 and associated instruments. Also depicted in FIG. 4 is a device disabling switch 106 configured to disable activity of the instrument temporarily. The cart 108 depicted in FIG. 4 is configured for easy movability within the operating room or catheter lab, one advantage of which is location of the operator control station 82 away from radiation sources, thereby decreasing radiation dosage to the operator.

Figure 5:
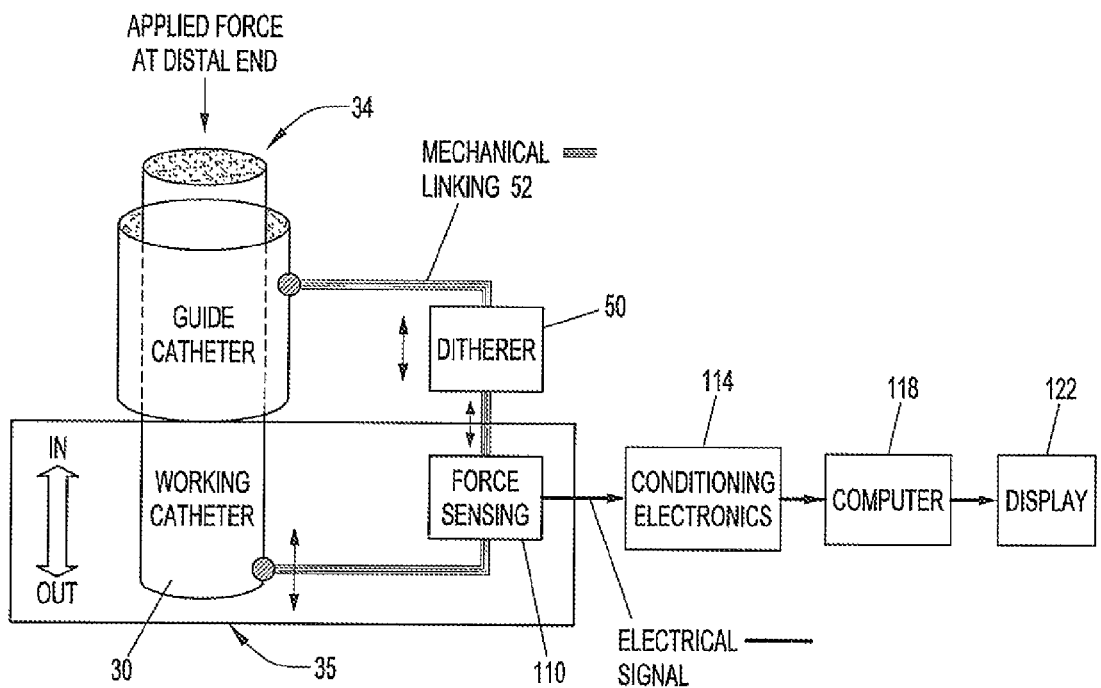
FIG. 5 illustrates a schematic representation of a method and system for dithering a working instrument relative to a guide instrument according to one embodiment of the invention.

FIGS. 5-11 illustrate schematically various methods of accomplishing force estimation at the distal end 34 of a working instrument 30 by using a dithering technique. FIG. 5 illustrates an embodiment in which the working instrument 30 dithers with respect to substantially stationary guide instrument 4. In order to dither the working instrument 30 back and forth (longitudinally), the mechanical ditherer 50 will drive the working instrument 30 through a force sensor 110 which will measure the direct force needed to insert and withdraw the working instrument 30 in and out of the guide instrument 4. The ditherer 50 is mechanically grounded (via a mechanical linkage 52) to a proximal region 35 of the guide instrument 4 and is thus stationary to the guide instrument 4 but the force sensor 110 and working instrument 30 move together relative to the guide instrument 4. Readings from the force sensor 110 may be sent through conditioning electronics 114 then to a computer 118 for data processing, and finally to a display 122.

Figure 6:
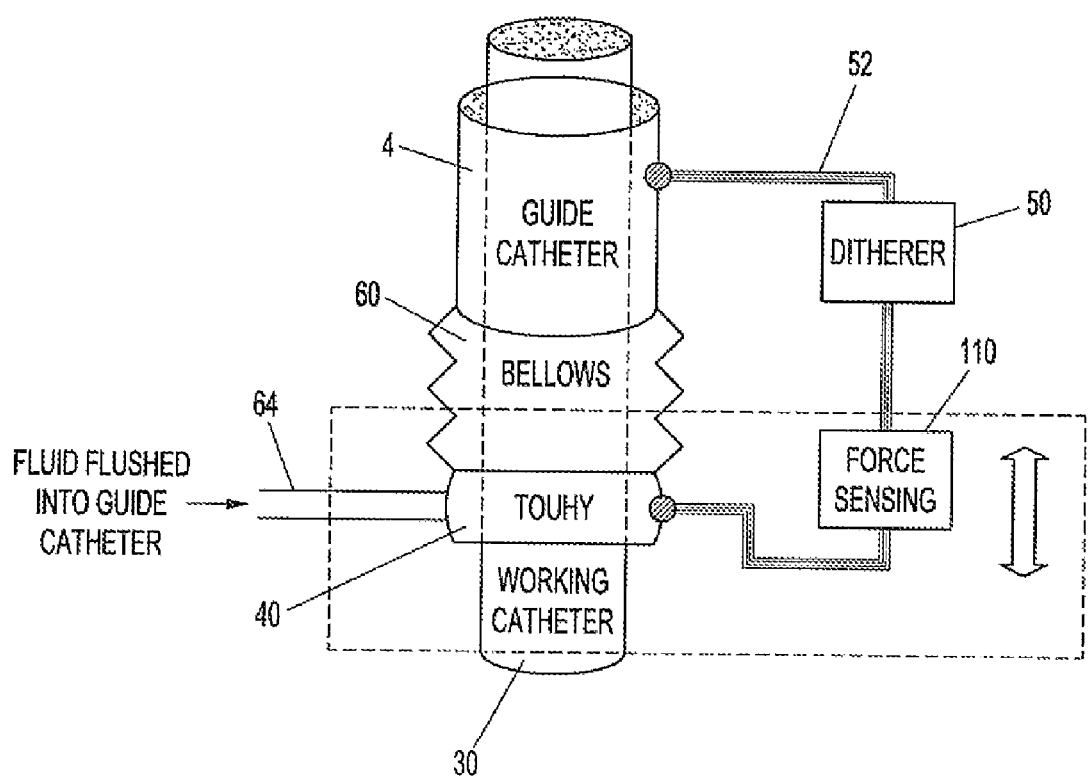
FIG. 6 illustrates a schematic representation of a method and system for dithering a working instrument relative to a guide instrument according to another embodiment of the invention.

FIG. 6 illustrates an alternative embodiment in which the ditherer 50 and force sensor 110 are mechanically linked to a seal 40 such as a Touhy seal. The Touhy seal 40 acts as a fluidic seal which can add significant and erratic drag to the reciprocating in-and-out motion of the working instrument 30 which would adversely affect the accuracy of readings from the force sensor 110. The embodiment of FIG. 6 eliminates this effect by mechanically securing or locking the Touhy seal 40 to the working instrument 30 so the two are dithered together. In addition, FIG. 6 illustrates the flexible bellows 60 that is connected to the proximal end of the guide instrument 4 at one end and secured to the Touhy seal 40 at the other end. The bellows 60 includes a flush line 64 that is used to delivery pressured saline as described herein. The bellows 60 expands and contracts like an accordion with the dithering motion. The bellows 60 advantageously applies a very low drag force on the working instrument 30 during the dithering motion as opposed to the high drag force that would be applied if the working instrument 30 was dithered through the Touhy seal 40.

Figure 7:
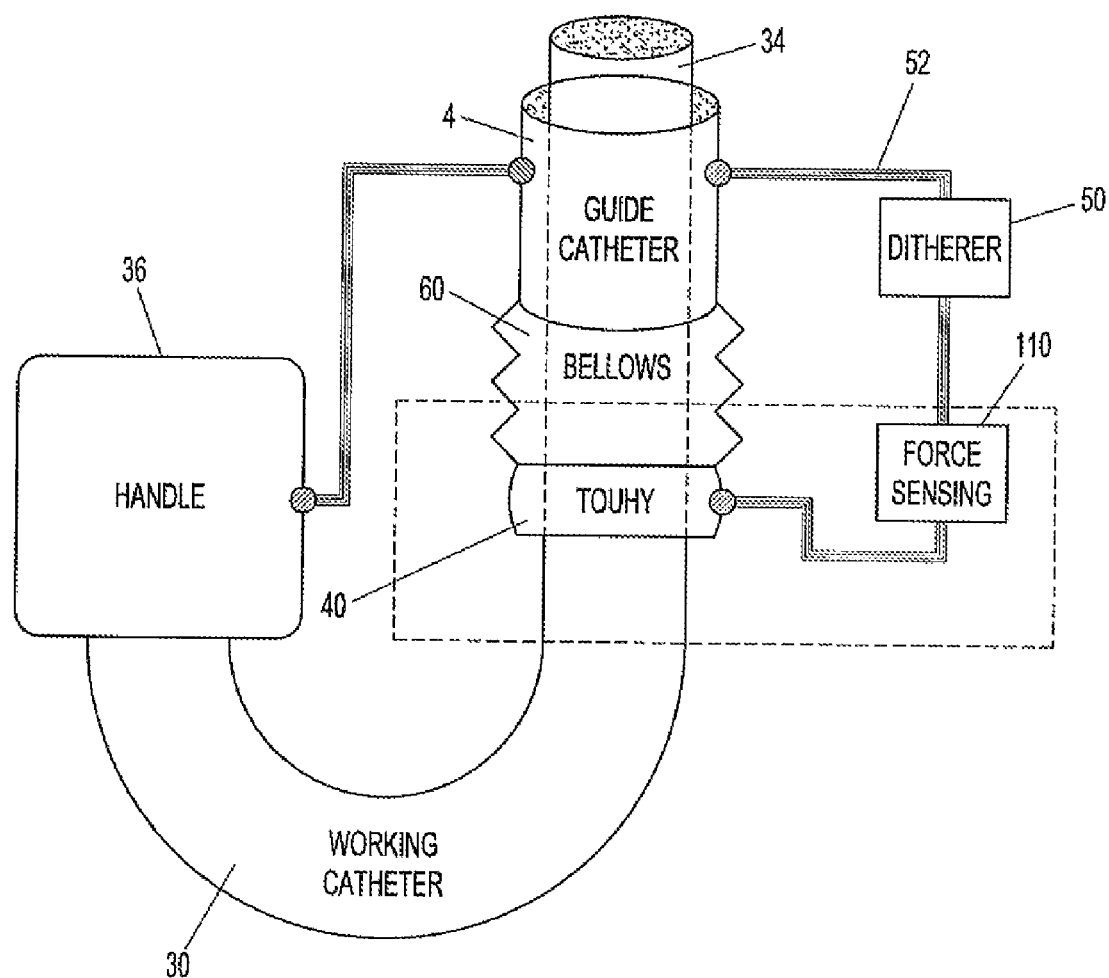
FIG. 7 illustrates a schematic representation of a method and system for dithering a working instrument relative to a guide instrument according to one embodiment of the invention.

FIG. 7 illustrates yet another embodiment which further secures or grounds a handle 36 of the working instrument 30. Generally, disposable working instruments 30, such as the ablation catheters available from such suppliers as Boston Scientific and Biosense Webster under trade names such as "Blazer™" and "NaviStar™" are typically manufactured with a handle 36 located on their proximal end. Unsecured, this handle 36 would likely apply forces on the Touhy seal 40 and/or working instrument 30 that would be read by the force sensor(s) 110 and perhaps mistakenly be interpreted as applied forces at the distal end 34 of the working instrument 30. Because of this, in the embodiment illustrated in FIG. 7, the handle 36 is isolated or guarded from the Touhy seal 40 and the force sensor(s) 110. The "guarding" may be accomplished by securing the instrument handle 36 into a holder such as the clamp 58 as shown in FIG. 1A.

The handle 36 may be grounded in one of a number of ways. One variation is to physically ground the handle 36 to the guide instrument 4 as shown in FIG. 7. In this case the handle 36 would be stationary relative to the guide instrument 4. As another alternative, the handle 36 may be grounded to a common carriage or mounting plate on which the guide and sheath instrument splayers 14, 16 are mounted. In this configuration the handle 36 is again grounded with respect to the guide instrument 4 albeit indirectly via a common carriage or mounting plate.

Figure 8:
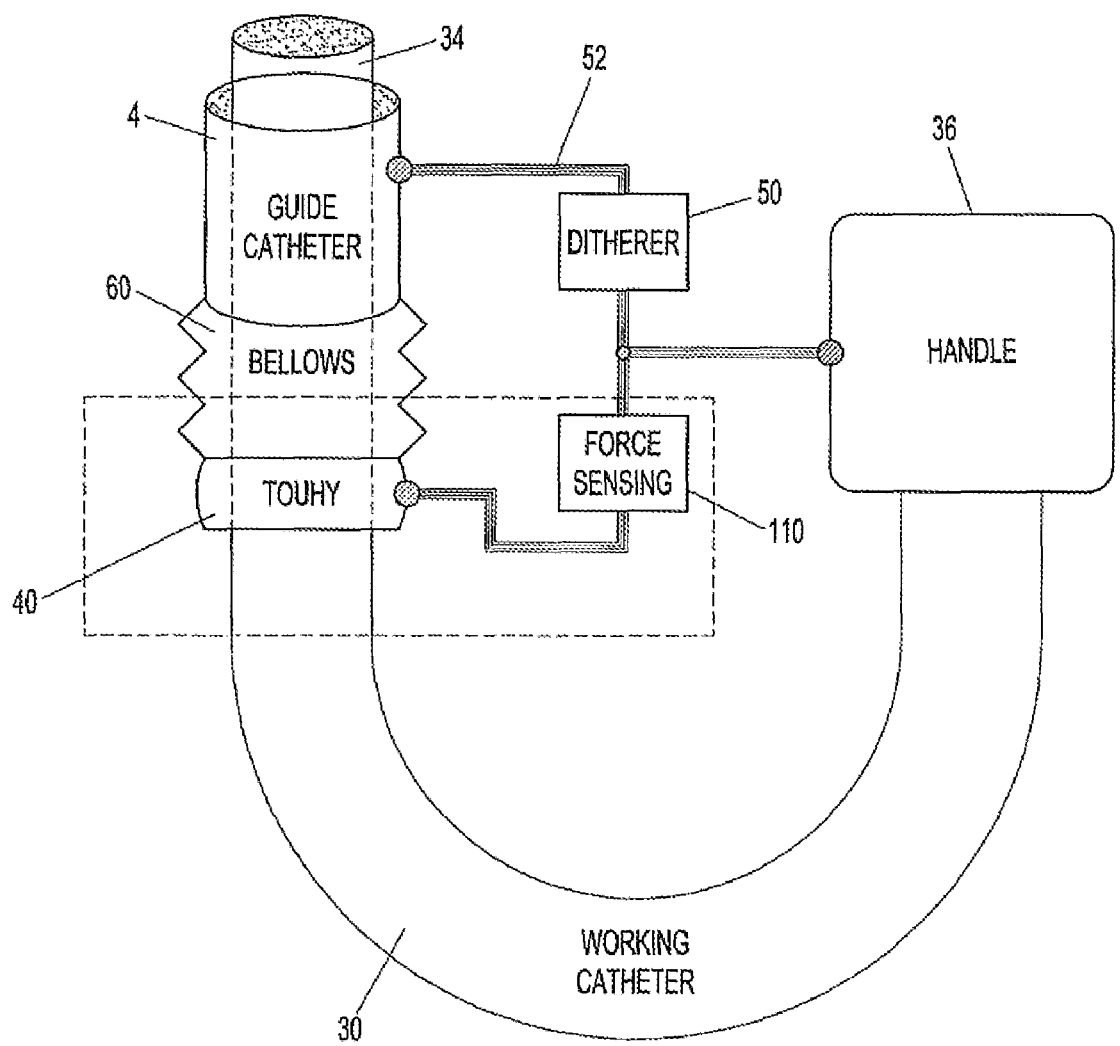
FIG. 8 illustrates a schematic representation of a method and system for dithering a working instrument relative to a guide instrument according to one embodiment of the invention.

FIG. 8 illustrates another embodiment in which the handle 36 is secured to the mechanical ditherer 50 via a securing member such as a clamp. In this embodiment, the handle 36 would dither along with the Touhy seal 40 and the working instrument 30. It is important to note that the force used to dither the handle 36 back and forth does not go through the force sensor(s) 110 and so any forces needed to move the handle 36 (or any accidental forces applied to the handle 36) are not seen by the force sensor(s) 110. Consequently, in this case, the handle 36 would be completely guarded within the system and there would be no periodic offset force.

In one embodiment, a drape 130 may be used to isolate non-sterile equipment from the sterile, surgical environment. In this regard, the drape 130 may cover the ditherer 50. If the drape 130 is attached to the force sensor(s) 110 and happens to catch on a person or equipment, it may pull on the force sensor(s) 110 and add an unwanted force measurement (e.g., artifact). Because of this, the portion of the drape 130 that is around the force sensor(s) 110 preferably is guarded—in this case by attaching it to a rigid ring 132, comprising materials such as metals or polymers, that surrounds the force sensor(s) 110 and Touhy seal 40. The guard ring 132 may be attached to the system with any number of methods.

Figure 9:
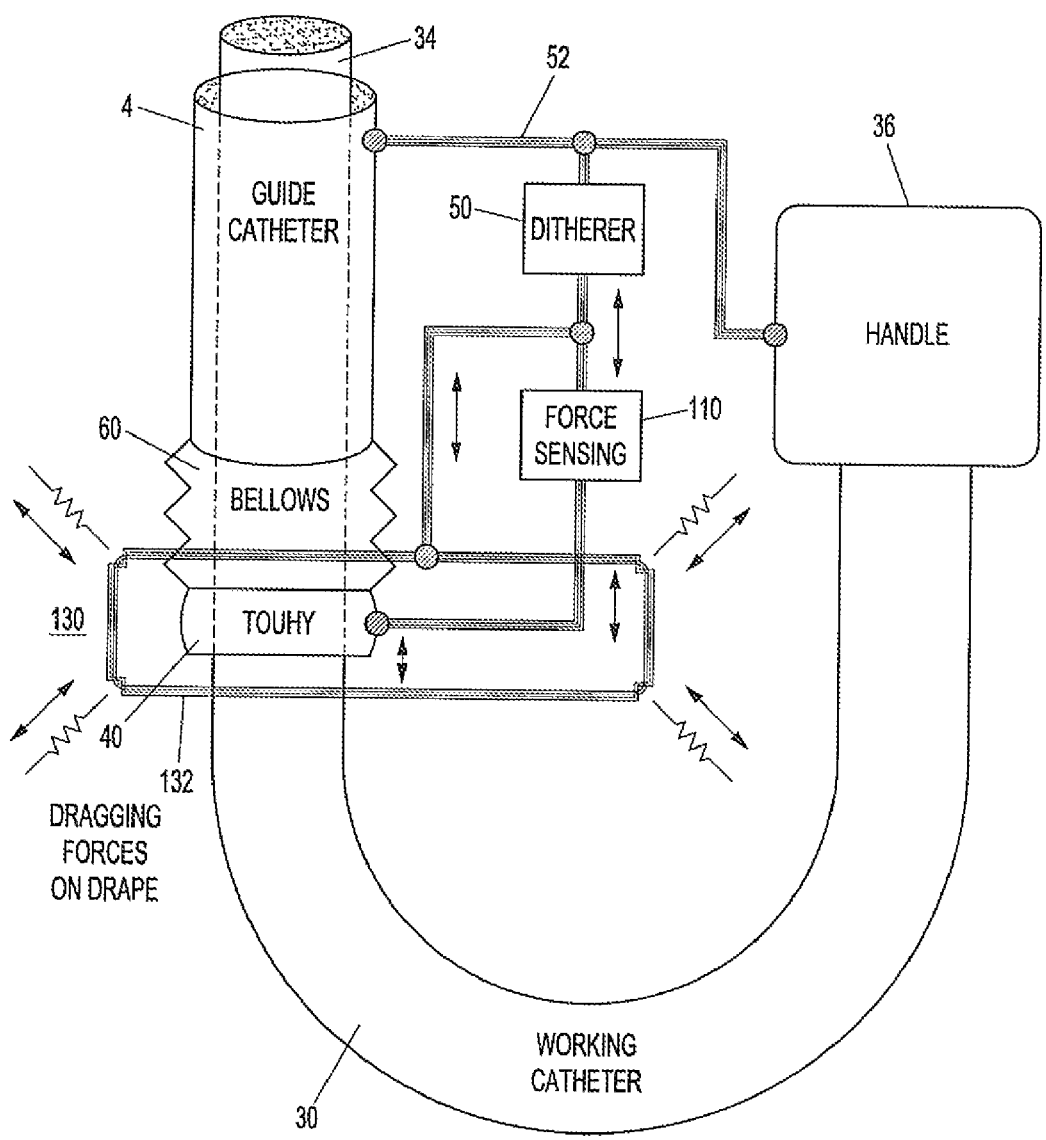
FIG. 9 illustrates a schematic representation of a method and system for dithering a working instrument relative to a guide instrument according to one embodiment of the invention.
Figure 10:
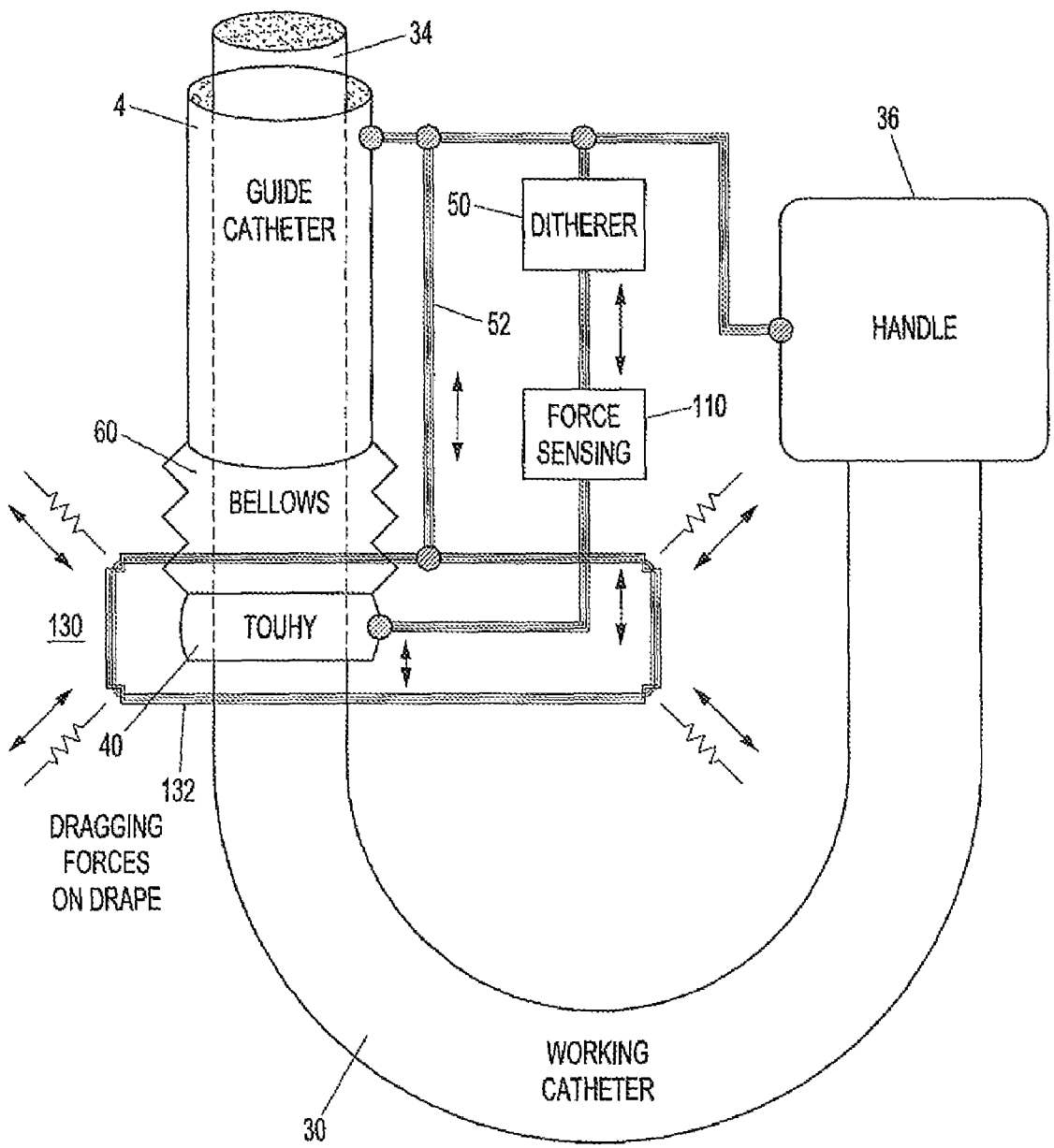
FIG. 10 illustrates a schematic representation of a method and system for dithering a working instrument relative to a guide instrument according to one embodiment of the invention.

As shown in FIG. 9, the ring 132 is attached to a point where the drape 130 dithers along with the working instrument 30. Thus, accidental pulls on the drape 130 (outside of the drape guard 132) generally are not transferred into the force sensor(s) 110 (but is transferred to the ditherer 50) and preferably does not result in a false force measurement. Another variation is illustrated in FIG. 10 in which the drape guard ring 132 is secured to the guide instrument 4. Consequently, an accidental pull on the drape 130 (outside of the drape guard ring 132) advantageously is transferred into the stationary guide instrument 4 and not into the force sensor(s) 110. In this embodiment, there may be a small amount of movement between the Touhy seal 40 and/or force sensor(s) 110 (which is dithered) and the stationary guard ring 132, which will may cause bunching and stretching of the drape 130 inside the guard ring. The drape 130 preferably is very compliant and this differential motion causes a small amplitude periodic force which is substantially the same during insertion and withdrawal and may thus be subtracted in subsequent force sensing data processing.

Figure 11:
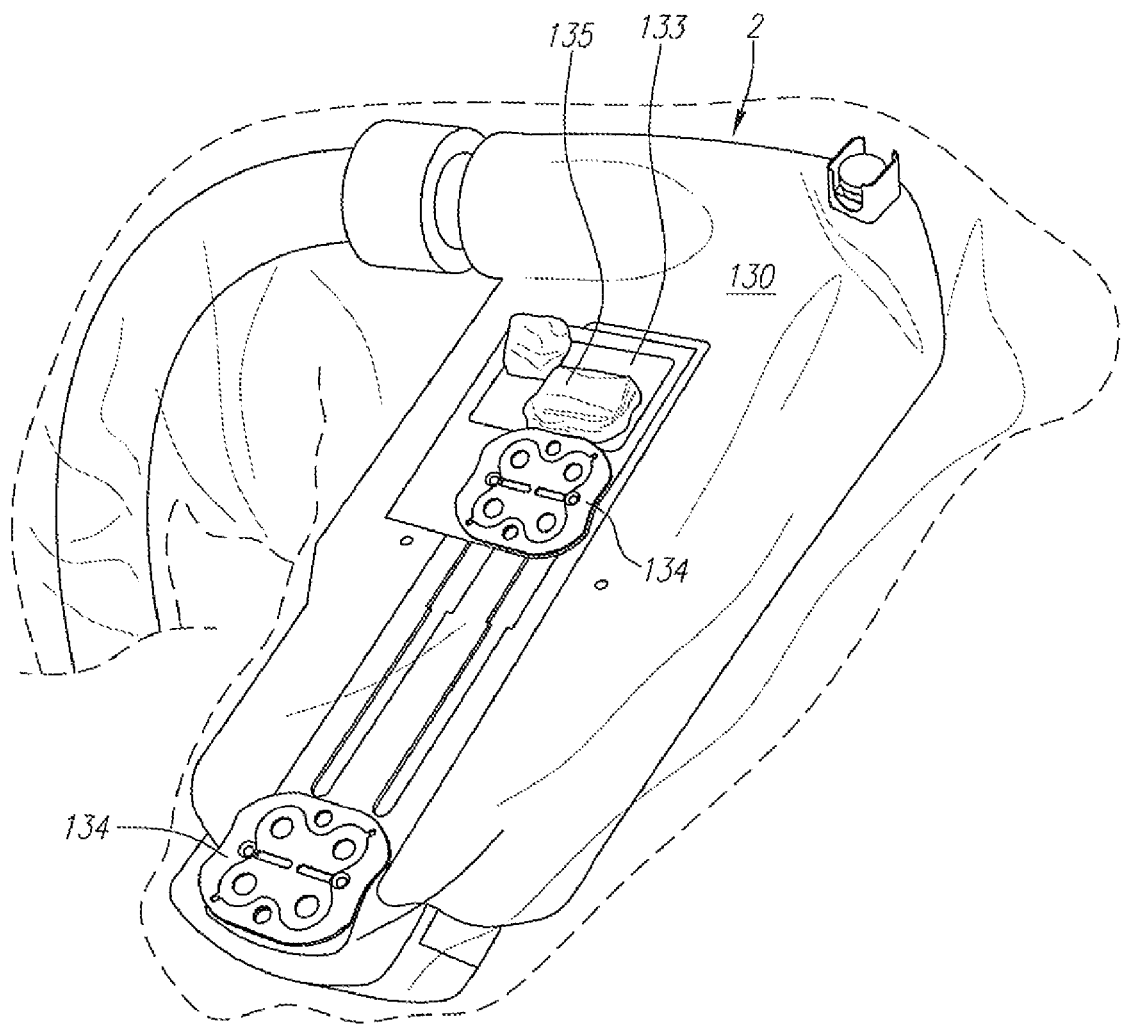
FIG. 11 illustrates a drape being positioned over the robotic instrument system.

FIG. 11 illustrates one embodiment of a drape 130 that is shown loaded onto a robotic instrument driver 400. The drape 130 includes platform covers 134 having a series of holes which are used to mount the splayers 14, 16. Also, proximal of the platform cover 134 for the guide instrument splayer 14 is a flexible boot 136 made of a very flaccid rubber or polymeric material that is surrounded by a ring 133 of semi-rigid material. The ring 133 is secured to the robotic instrument driver 400 such that any pulling, tugging, or other forces are transmitted through the drape 130 to the robotic instrument driver 400 and not the flexible boot 136. For example the semi-rigid ring 133 may be secured to the grounded drape ring 132. In this regard, the boot 136 and ring 133 isolate forces on the drape 130 from affecting the force measurements obtained using the force sensors 110. The working instrument 30 passes through the flexible boot 136 and can be secured to the ditherer 50.

Figure 12:
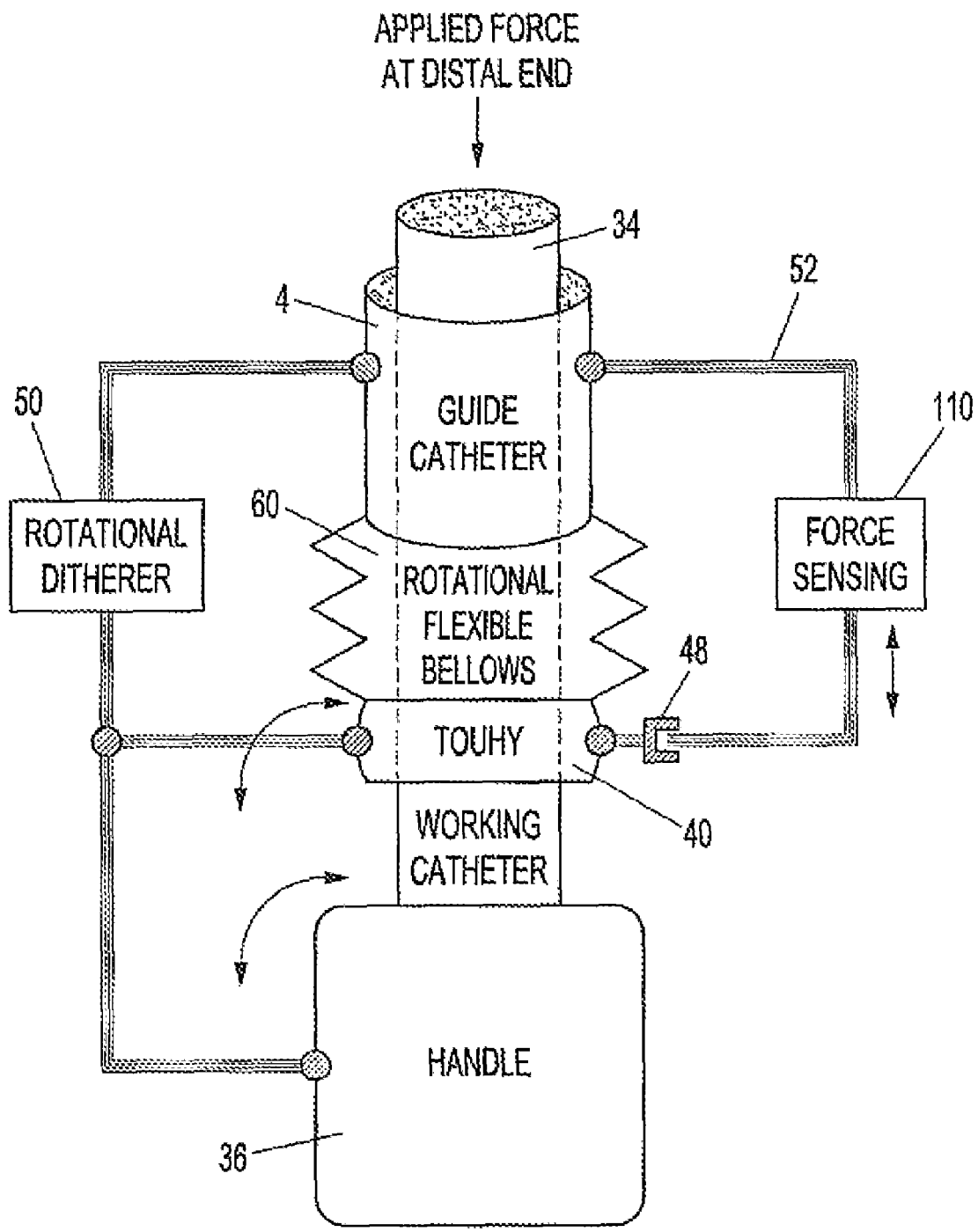
FIG. 12 illustrates a schematic representation of a method and system for dithering a working instrument relative to a guide instrument according to one embodiment of the invention. In this embodiment, the dithering motion is rotational as opposed to longitudinal.

As mentioned above, a different variation of dithering comprises dithering the working instrument 30 rotationally as opposed to longitudinally or axially. As seen in FIG. 12, the force sensor(s) 110 would no longer be in series with the mechanical ditherer 50. Rather, the ditherer 50 would in this case be rotational and because it is an orthogonal motion (relative to the in-and-out motion due to the distal end force which may be applied to the working instrument 30), the orthogonal forces may be isolated from one another by using a bearing 48 allowing the force sensors 110 to measure the applied force at the distal end 34 as isolated from the forces caused by the rotational dithering motion.

Regardless of whether the dithering motion is rotational or longitudinal, the structure of the flexible bellows 60 facilitates the operation of this dithering force measurement system. For example, in the longitudinal embodiment, the bellows 60 provides low force from the longitudinal dithering and is volumetrically compliant to allow for the change of flush volume within the bellows 60 during the dithering process. In the rotational dithering embodiment, the bellows 60 is configured to allow for rotation of the ends of the bellows 60 while not creating a significant longitudinal force offset to the force sensor(s) 110.

Figure 13:
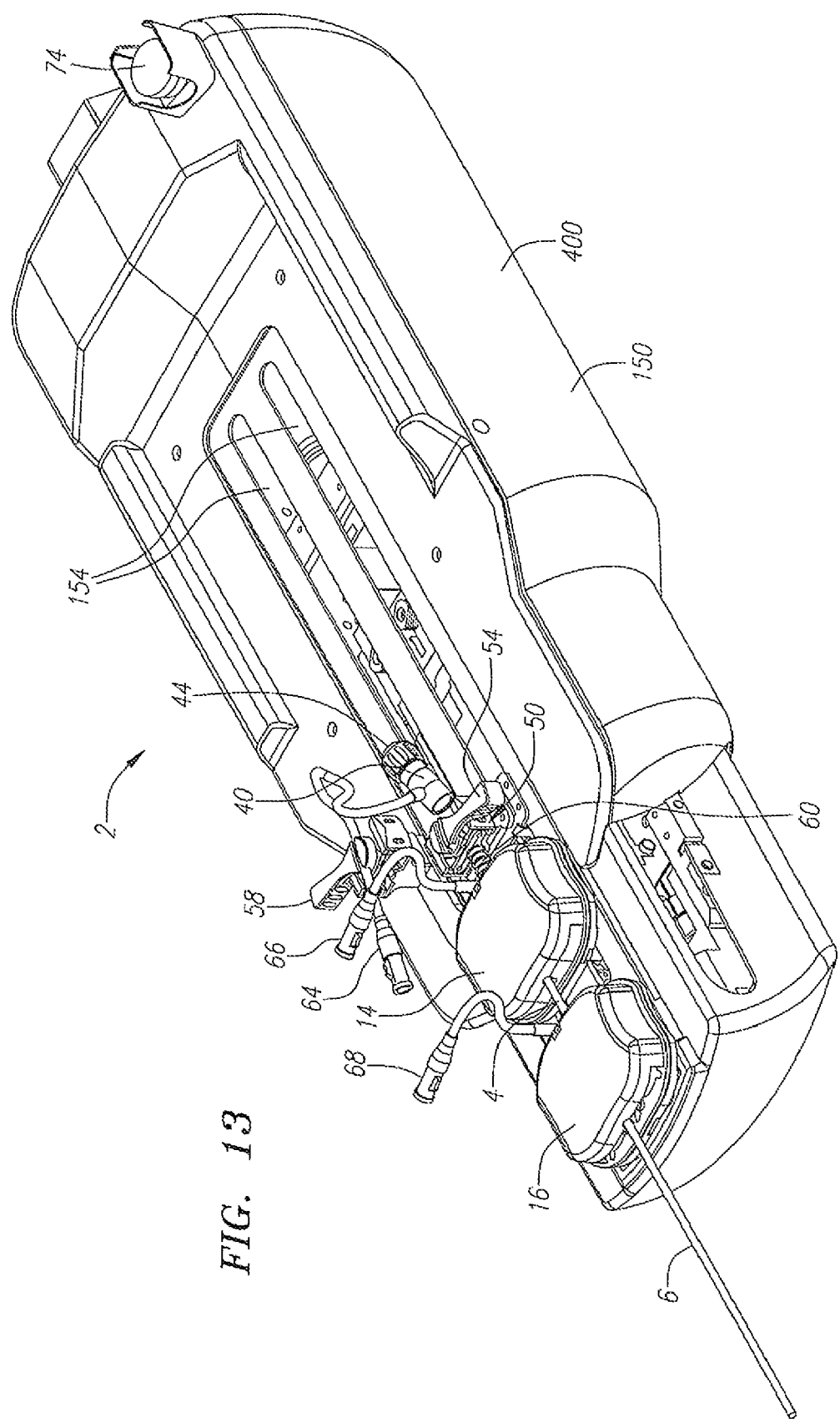
FIG. 13 illustrates a perspective view of a robotic instrument system without the working instrument.

FIG. 13 illustrates a perspective view of a robotic instrument system 2 according to one embodiment of the invention. The robotic instrument system 2 includes a housing 150 that is partially exposed in FIG. 13. The robotic instrument system 2 generally comprises a carriage configured to interface with structures coupled to or comprising the guide instrument splayer 14, and a carriage configured to interface with structures coupled to or comprising the sheath instrument splayer 16. Longitudinal slots 154 defined by the outer housing 150 of the robotic instrument driver 400 are configured to facilitate longitudinal movement of the carriages and associated splayers 14, 16 relative to the outer housing 150 of the robotic instrument driver 400

Figure 14:
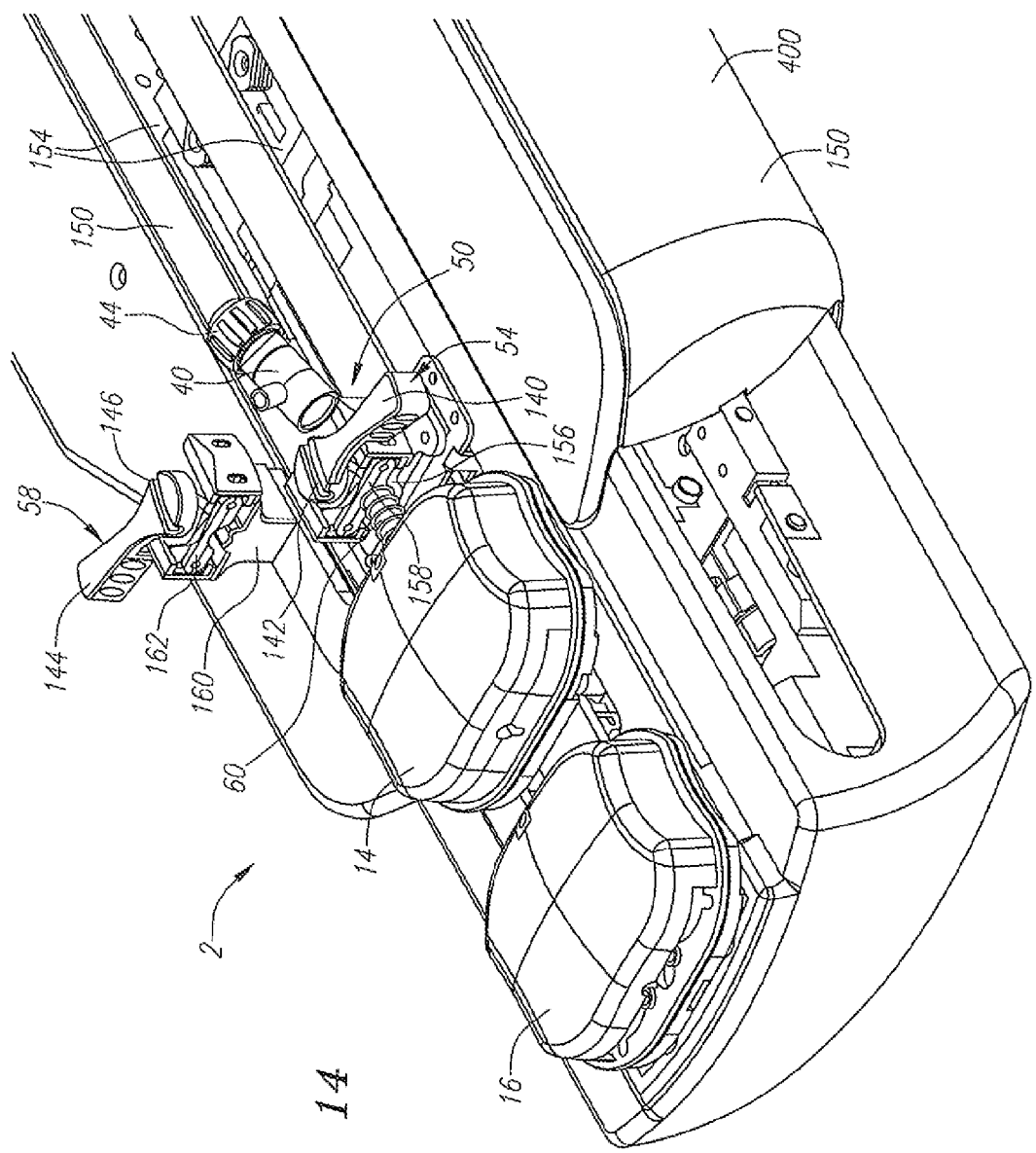
FIG. 14 illustrates a perspective view of a distal end of the robotic instrument system without the working instrument being attached. Also removed are the guide instrument and the outer sheath.

FIG. 14 illustrates a magnified perspective view of the distal portion of the robotic instrument system 2. The guide instrument 4 and sheath instrument 6 are not shown for clarity purposes. As seen in FIG. 14, the clamp 54 for the Touhy seal 40 may comprise a rotatable handle 140 that is used to frictionally hold the Touhy seal 40 in place. For example, the clamp 54 may comprise a lower seat 156 that is positioned on the load bearing aspect of the ditherer 50 and an upper clamping member 158 that, when tightened via the handle 140, frictionally secures the Touhy seal 40 in a sandwich arrangement. The handle 140 may comprise a groove or notch 142 that can be used to temporarily secure a flush line or the like.

FIG. 14 also illustrates a clamp 58 for the handle 56 of the working instrument 30 that also comprises a rotatable handle 144 that is used to frictionally secure the handle 36 of the working instrument 30 in place. The clamp 58 may comprise a lower seat 160 that is fixedly secured to the carriage (or a support member secured to the carriage) and an upper clamping member 162 that, when tightened via the handle 144, frictionally secures the proximal handle 36 in a sandwich arrangement. The rotatable handle 144 comprises a groove or notch 146 that can be used to temporarily secure a flush line or the like.

Figure 15:
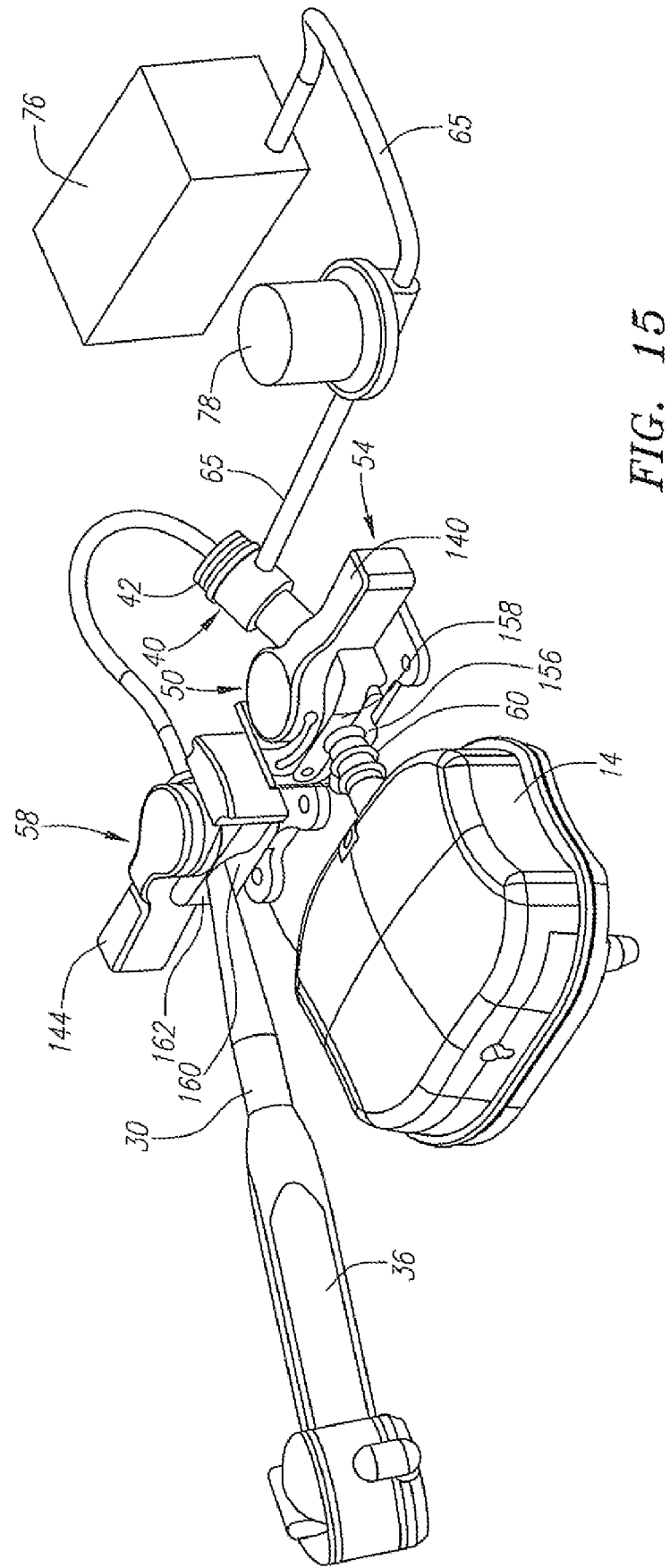
FIG. 15 illustrates a working instrument being secured via two clamps to a seal. The seal interfaces with a flexible bellows that interfaces with the guide splayer. Also illustrated is a source of fluid (e.g., pressurized saline) that is used to flush the region between the guide instrument and the working instrument.

FIG. 15 illustrates an assembly drawing of the guide instrument splayer 14 along with the mechanically coupled mechanical ditherer 50. A working instrument 30 is shown being inserted into the proximal end of the Touhy seal 40. The distal end 34 of the working instrument 30 is not shown in FIG. 15. The Touhy seal 40 of FIG. 15 illustrates a proximal end having a series of threads 42 on which is mounted a cap 44 which is illustrated in, for example, FIGS. 13, 14, 15 (showing threads 42), 16, and 17). The cap 44 may be tightened on the threads 42 to form a fluidic seal that prevents fluid from escaping between the interface of the seal 40 and the working instrument 30. FIG. 15 also illustrates a conduit 65 that is connected to the interior of the Touhy seal 40. The conduit 65 is connected to a source of pressurized flush solution 76 which may comprise, for instance, pressurized saline. A pressure regulator 78 or the like may be interposed in the conduit 65 between the pressurized flush solution 76 and the Touhy seal 40 to ensure that a constant pressure of fluid is applied. Of course, in other embodiments, the conduit 65 may be fluidically coupled to the flexible bellows 60.

Figure 16:
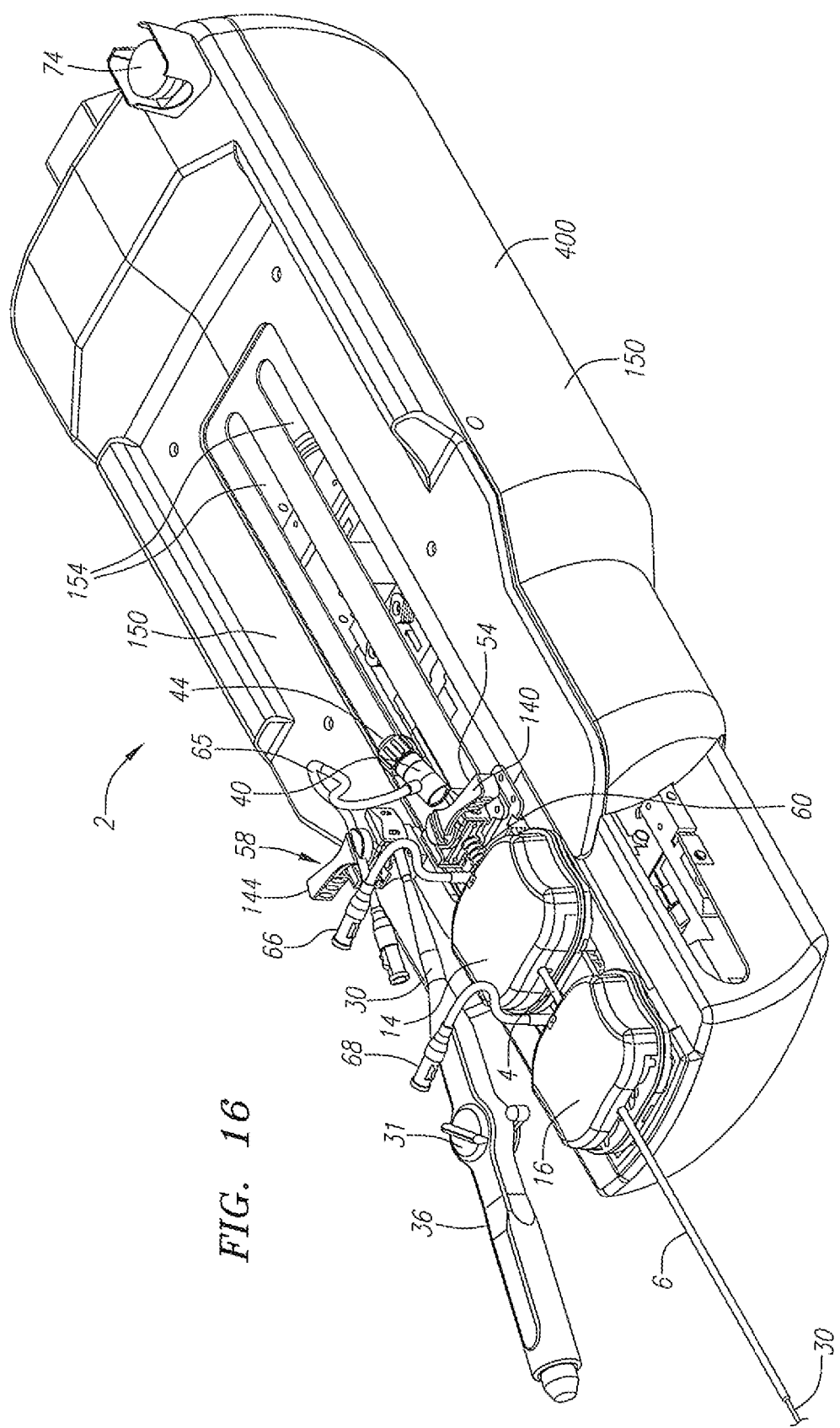
FIG. 16 illustrates a perspective view of a robotic instrument system with the working instrument being loaded thereon.
Figure 17:
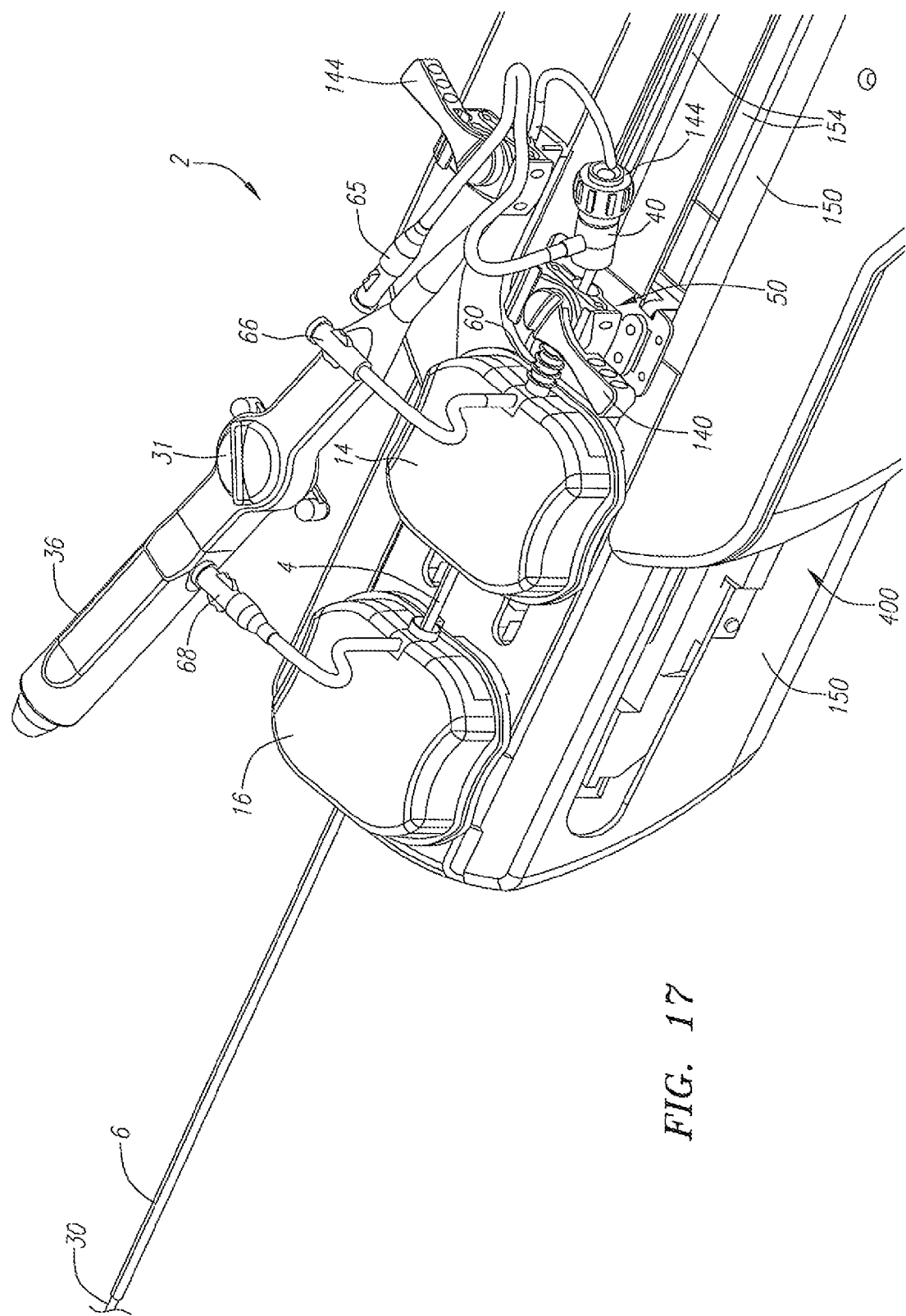
FIG. 17 illustrates another perspective view of a robotic instrument system with the working instrument being loaded thereon.

FIGS. 16 and 17 illustrate perspective views of the robotic instrument system 2 having a working instrument 30 being inserted into the Touhy seal 40. The working instrument 30 passes through the lumen 8 of the guide instrument 4 and the lumen 10 of the sheath instrument 6. The handle 36 of the working instrument 30 is secured to the robotic instrument driver 400 via the clamp 58. FIGS. 16 and 17 also illustrate a flush line or conduit 65 that is held in place via the groove 146 in the handle 144. With reference to FIGS. 16 and 17, the working instrument 30, which in certain embodiments may include an off-the-shelf steerable or nonsteerable catheter, may include a steering member 31 located on the handle 36. In this case, the steering member 31 is preferably placed into a neutral position to permit steering by the robotic instrument driver 400.

Figure 18A:
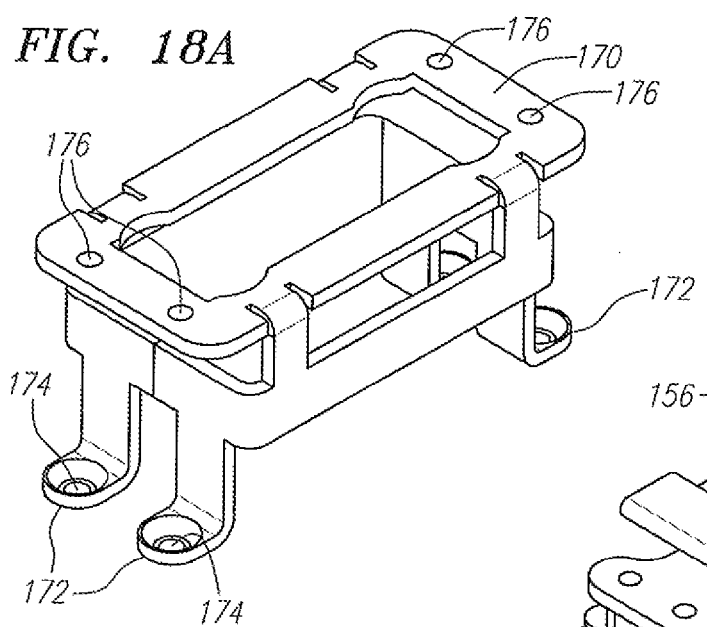
FIG. 18A illustrates a guard ring that is mounted around a load bearing member of the ditherer.
Figure 18B:
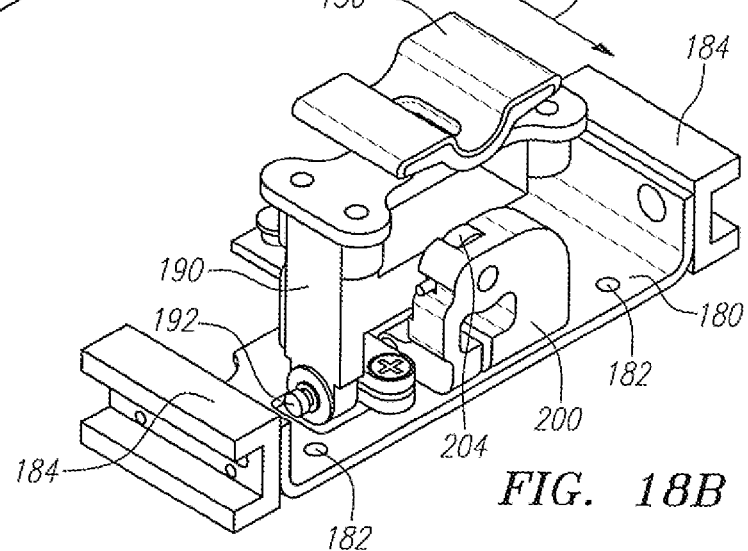
FIG. 18B illustrates the load bearing member being mounted on a pivot point between opposing load cells each of which contain a force sensor for measuring compressive forces.
Figure 18C:
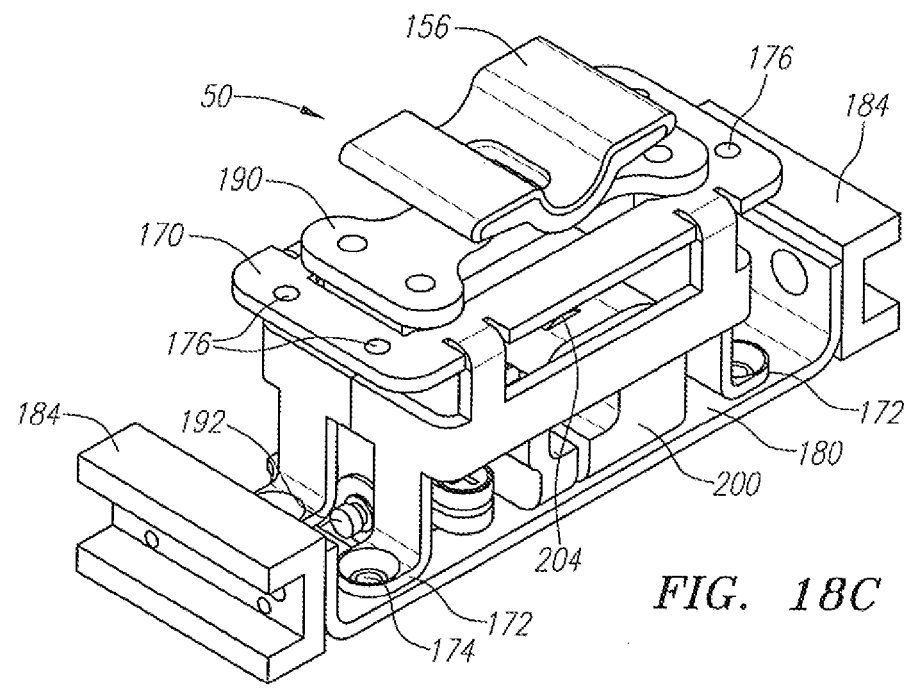
FIG. 18C illustrates the structure of FIG. 18 with the guard ring mounted about the load bearing member.

FIGS. 18A-C illustrate various aspects of the mechanical ditherer 50 according to one embodiment. FIG. 18A illustrates a guard ring or cage 170 that is mounted to a moveable dither carriage 180 (as seen in FIGS. 18B and 18C). The guard ring 170 may be secured via mounting pads 172 having holes therein for passage of a screw, bolt, or the like (not shown) that mates with respective holes 182 in the dither carriage 180. The guard ring 170 may include additional holes 176 on a top surface thereof for mounting, for example, the drape 130. In this regard, the drape 130 dithers along with the working instrument 30. Any accidental pull on the drape 130 would not be transferred into load cells and would not result in a false force measurement.

Figure 19:
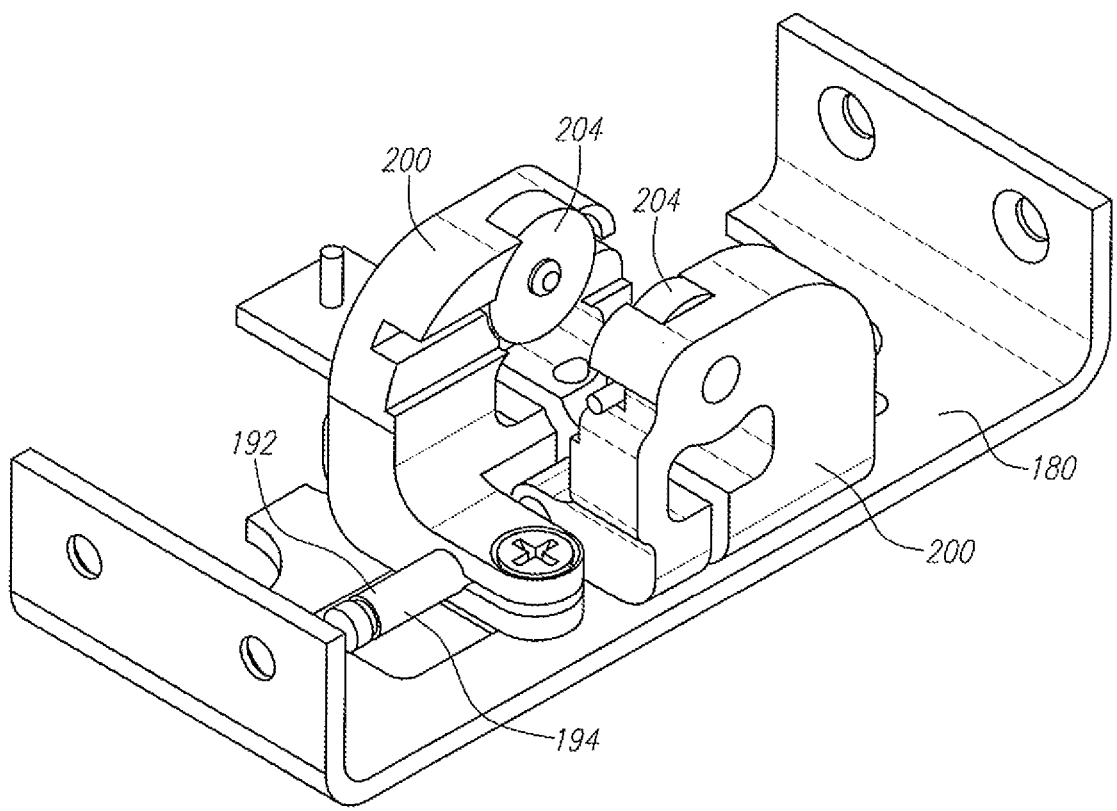
FIG. 19 illustrates a perspective view of the dither carriage holding the opposing load cells. Also shown are the opposing force sensors disposed on the load cells.

FIG. 18B illustrates the load bearing member 190 of the mechanical ditherer 50. The load bearing member 190 is pivotally mounted to the dither carriage 180. The load bearing member 190 pivots about pivot point 192 in the manner of an inverted pendulum. The pivot point 192 may include a shaft 194, pin, bearing or the like that permits dithering movement of the load bearing member 190 along with the dither carriage 180. The dithering motion causes movement of the dither carriage 180 and attached load bearing member 190 in the direction of arrow A in FIG. 18B. Two load cells 200 (one of which is illustrated in FIG. 18B) are positioned on either side of the load bearing member 190 and each contain a force sensor 204. FIG. 19 illustrates a perspective view of the dither carriage 180 including the load cells 200 having the respective force sensors 204 loaded therein. As best seen in FIGS. 18B and 18C, the load bearing member 190 is fixedly secured to the dither carriage 180 via the pivot point 192 and moves along therewith during the dithering movement.

The two force sensors 204 measure compressive forces. In particular, the two force sensors 204 output a small voltage that is proportional to or correlates with the applied force. The load bearing member 190 comprises the seat 156 onto which is mounted the Touhy seal 40 (or in other embodiments the working instrument 30). As the dither carriage 180 is moved back and forth in the reciprocating manner, the forces experienced on the proximal end of the working instrument 30 (or Touhy seal 40) are then measured via the output signals on the two force sensors 204. The load bearing member 190, which swings back-and-forth in a pendulum-like manner, alternatively makes contact with the opposing force sensors 204. When the load bearing member 190 does not contact a force sensor 204, the force sensor 204 outputs a baseline or zero signal (e.g., no voltage).

The analog voltage signal from each force sensor 204 is amplified via an amplifier (not shown). The amplified signal may then pass through a flex circuit on the robotic instrument driver 400 structure to one or more circuit boards (not shown) mounted to the carriage or chassis. The analog signal then is transformed into a digital signal via an analog-to-digital converter (ADC). The digital signals can then be passed to an off-board computer located, for example, at the operator control station 82. The operator control station 82 may then convert the digital data into a usable form using, for example, the single cycle subtraction algorithm described in more detail below. The separation of the load cells 200 is dimensioned such that there is a relatively small gap between the load cells 200 and the load bearing member 190 as there is a small dead band created when the load bearing member 190 is not touching either of the two opposing force sensors 204.

Referring to FIGS. 18B and 18C, the dither carriage 180 is secured to two c-shaped channels 184. The channels 184 engage with correspondingly dimensioned rails (not shown) such that the entire dither carriage 180 is able to move back-and-forth in the direction of arrow A in FIG. 18B.

Figure 20:
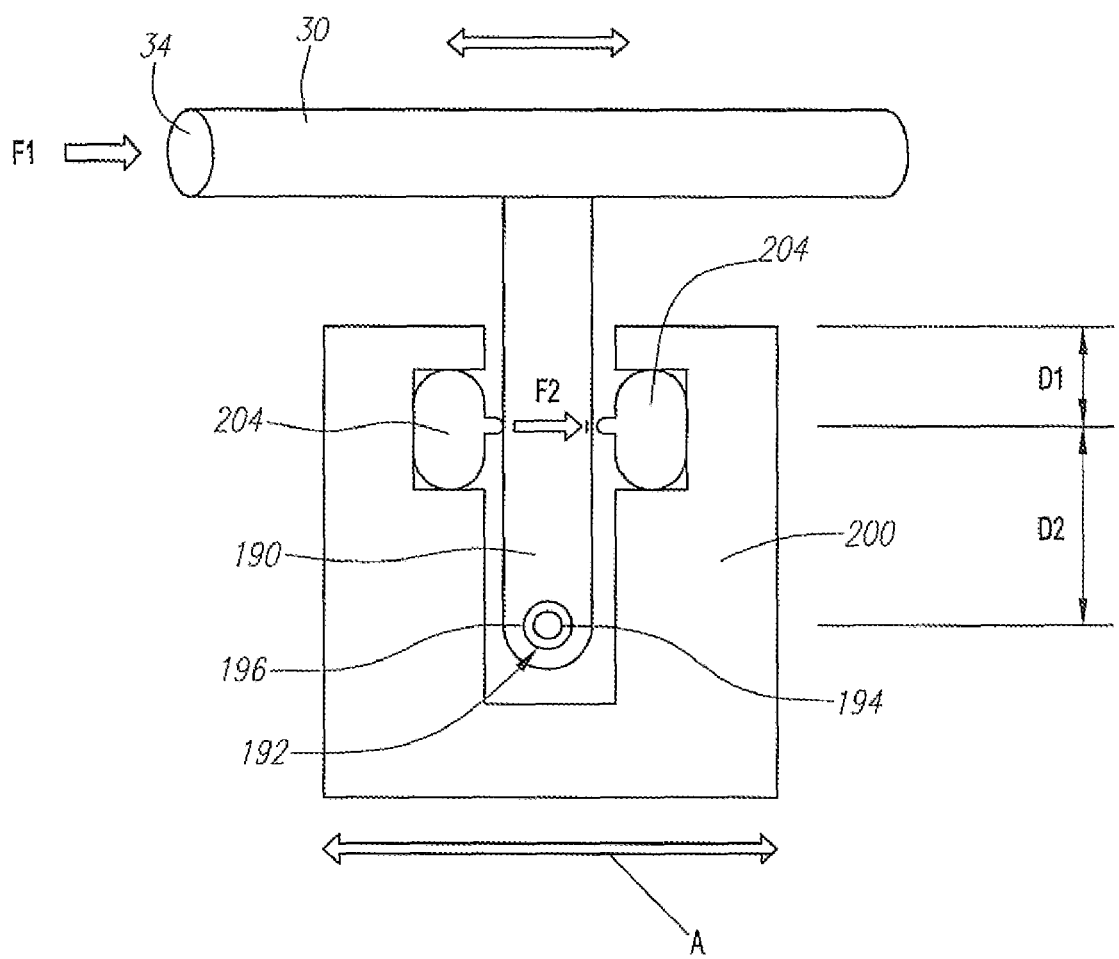
FIG. 20 is a schematic representation of a working instrument being operatively coupled to the load bearing member of the ditherer. Also shown are the force sensors contained in the opposing load cells.

FIG. 20 schematically illustrates the load bearing member 190 moving about pivot point 192 between the opposing load cells 202 holding the force sensors 204. The pivot point 192 may include a stationary shaft 194 that is mounted with respect to the opposing load cells 202. For example, as seen in FIG. 19, the shaft 194 may be driven through the base of both load cells 202. The load bearing member 190 is sandwiched between the two load cells 202 and is held on the shaft 194 via bearings 196 or the like that allows rotational motion of the load bearing member 190 pivot about the shaft 194. Since the pivot 192 ultimately holds the working instrument 30, force felt by the working instrument 30 will cause the load bearing member 190 to rotate about pivot point 192 and press up against (e.g., compress) one of the force sensors 204. The force sensors 204 measure this pivot force from which instrument force feedback can then be calculated.

The mechanical ditherer 50 will dither the load cells 200 back and forth (in a linear displacement fashion approximately 1.5 mm from peak-to-peak). Of course other stroke lengths are also contemplated. As the mechanical ditherer 50 changes direction, the load bearing member 190 rotates a very small amount to exchange force from one force sensor 206 to the other force sensor 206 then the linear motion of the ditherer carriage 180 continues to carry the load bearing member 190 in a linear motion which pushes in or pulls out the working instrument 30. The load bearing member 190 acts as a static lever arm. By using two force sensors 204, each can be used to verify that the other force sensor 204 is working properly. For example, the dead band zone where the load bearing member 190 is not touching either force sensor 204 occurs once per dither cycle and is used to confirm the force sensor 204 "zero load" position and to test proper force sensor 204 operation.

Extremely large forces will not be sensed by the force sensors 204 but will be transferred directly to the load cell mounts 200 so as to protect the force sensors 204 from damage. The load cell mounts 200 are designed to protect the force sensors 204 from excessive forces from the load bearing member 190 (excessive forces applied to a force sensors 204 may permanently damage them leading to incorrect force readings). To achieve this protection the load cell mounts 200 may have a precision ground cup into which the force sensor 204 sits. The depth of this cup may be just slightly shorter than the height of the force sensor 204 sitting in it, so that as the load bearing member 190 rotates to the force sensor 204 and load cell mount 200 it will push on the force sensor 204 at first. As additional force is applied by the load bearing member 190, the force sensor 204 (which has a very slight amount of compliance) reduces in height until the load bearing member 190 strikes the load cell mount 200. Thus, by controlling the depth of the precision ground cup in the load cell mount 200 and by knowing the compliance of the force sensor 204 in compression, the maximum force applied to the force sensor 204 can be set, which will protect the force sensor 204 excessive forces. Other methods of protecting the force sensors 204 can be achieved by using shims or fine pitched screws to adjust for the point where forces to the force sensors 204 are shunted anyway. The force sensors 204 themselves may be uni-directional compression force sensors (sometimes referred to also as load cells) rated at 5 lbs (e.g., available from Honeywell Sensotec-Lebow of Ohio).

Figure 21A:
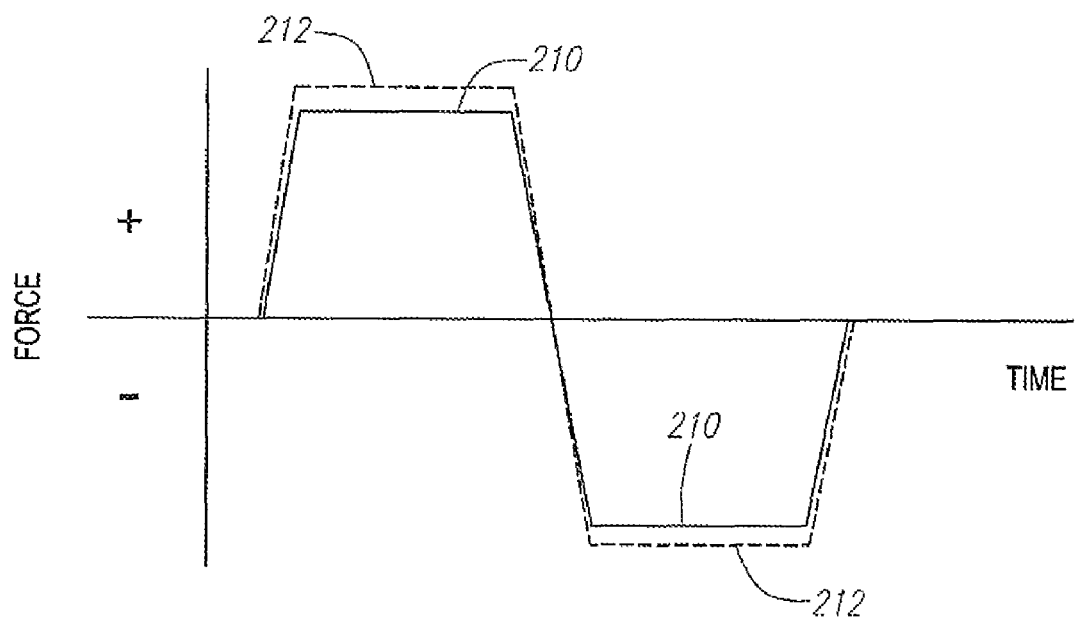
FIGS. 21A-21B illustrate the waveform or force profile obtained from the force sensors during a single insertion and withdrawal cycle.
Figure 21B:
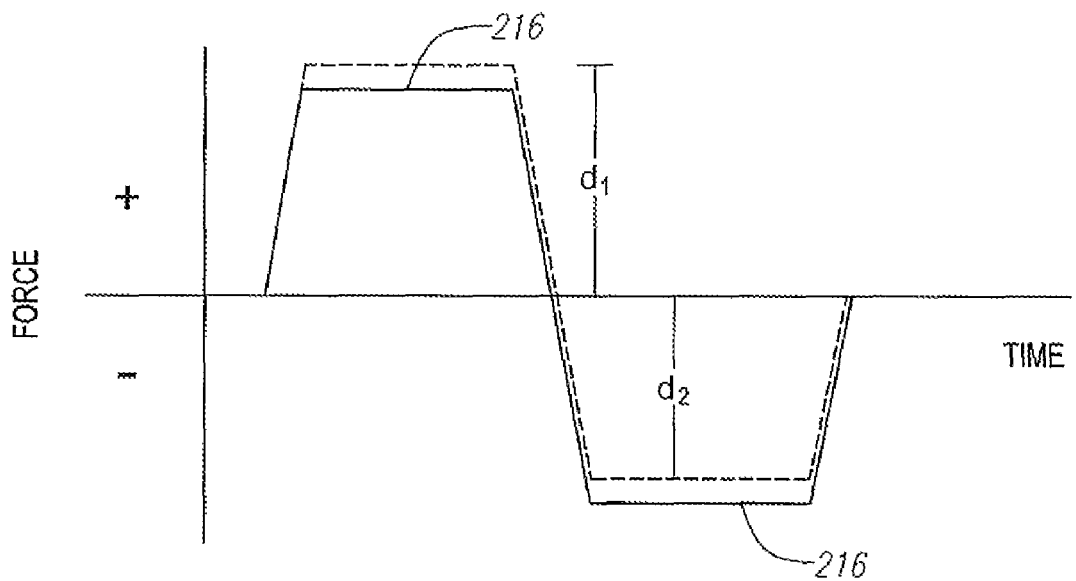

FIGS. 21A and 21B illustrate an exemplary waveform of the measured or observed forces using the force sensors 204 through a single dither cycle. The single dither cycle includes a single insertion stroke followed by a single withdrawal stroke. Positive forces are those measured during insertion while negative forces are those measured during withdrawal. In the embodiment described above, one force sensor 204 is used to measure insertion forces while the other, opposing force sensor 204 is used to measure withdrawal forces. As seen in FIG. 21A, the applied force increases in a substantially linear manner until the force plateaus. The point at which the force begins to plateau is taken at that point when the working instrument 30 begins to dither axially with respect to the guide instrument 4. After a period of constant or substantially constant force, the force then begins to decrease in a substantially linear manner. The force then goes "negative" as the working instrument 30 is withdrawn from the guide instrument 4. The force then plateaus at a negative value before returning to the origin.

FIG. 21A illustrates a condition in which no force is applied to the distal end 34 of the working instrument 30. FIG. 21A illustrates two such waveforms (solid line 210 and dashed line 212). Both waveforms, while having different amplitudes, are substantially symmetrical. This feature is particularly advantageous because the forces are symmetrical in nature, the resulting waveform shows an equal force on insert and on withdrawal. Consequently, in processing the obtained force measurement data from the force sensors 204, it is possible to take a one cycle average of the waveform that will eliminate the substantially symmetrical offset forces from the measurement leaving only the differential shift in force. This differential shift in force is the force that is applied at the distal end 34 of the working instrument 30. Consequently, measured or observed forces at the proximal region 35 of the working instrument 30 may be used to accurately and consistently estimate forces applied to the working instrument 30 at the distal end 34.

FIG. 21B illustrates a first or "baseline" waveform 216 (solid line) taken when no force is applied to the distal end 34 of the working instrument 30. FIG. 21B also shows the waveform 218 (dashed line) taken when a force is applied to the distal end 34 of the working instrument 30. As seen in FIG. 21B, the entire curve is shifted in the upward direction. With reference to FIG. 21B, the amplitude $d_1$ is now larger than the amplitude $d_2$. This difference between the baseline measurement and the measurement obtained upon application of a force may be used to quantify the force applied to the distal end 34 of the working instrument 30.

Figure 22:
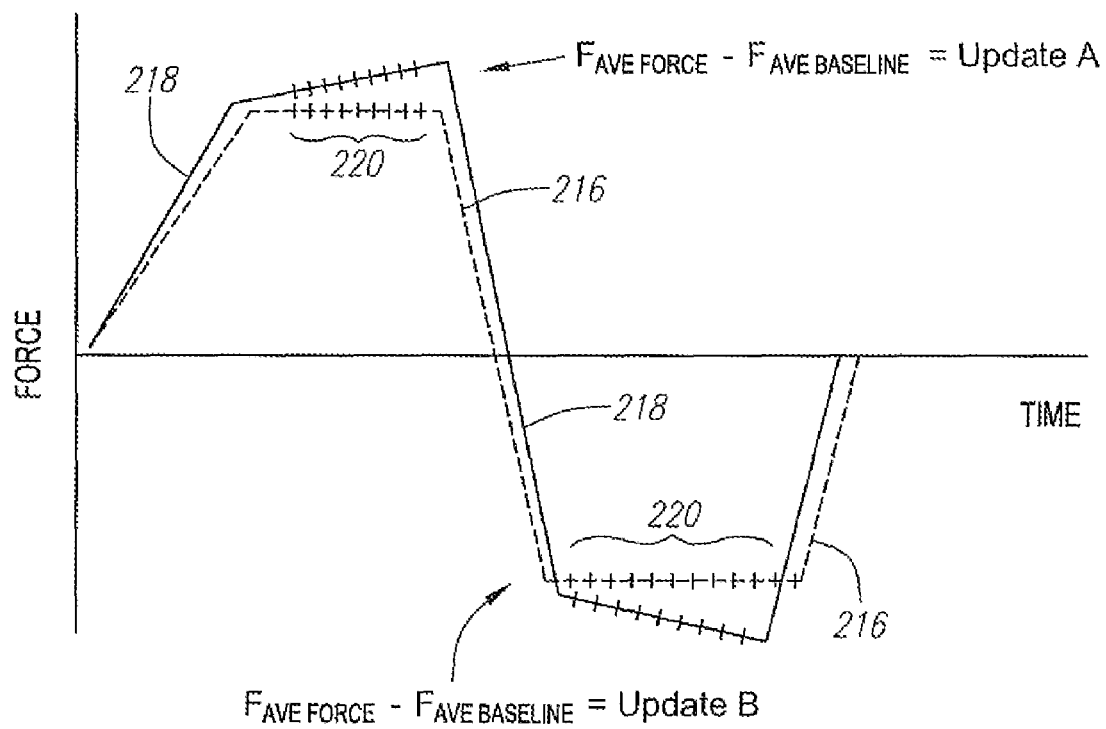
FIG. 22 illustrates a baseline waveform or force profile that is overlaid with the waveform or force profile obtained when the distal end of the working instrument is subject to an external force. The dashed line represents the baseline (no force at distal end) while the solid line represents the measurements obtained in response to an applied force at the distal end of the working instrument.

FIG. 22 illustrates a baseline waveform 216 (dashed line) along with an overlaid waveform 218 (solid line) obtained when a force is applied to the distal end 34 of a working instrument 30. According to one embodiment, a portion 220 of the plateau region of both the baseline waveform 216 and the waveform 218 created from the contact force are sampled in regular increments. For example, the force readouts from the sensors 204 may be sampled at one millisecond increments over their entire cycle. While the entire waveform may be sampled, different embodiments may choose to ignore portions of the sampled waveform. For example, in one embodiment, only those portions 220 of the plateaus are kept or utilized for the force algorithm with the remaining readout figures being ignored or deleted. The portion 220 of the waveform plateau may include a partial segment of the waveform that eliminates the endpoints as is shown in FIG. 22.

With respect to the algorithm, baseline force measurements are obtained at the baseline sampling locations in the plateau regions 220 for both the insertion stroke and the withdrawal stroke with no force applied on distal end 34 of working instrument 30. An average force measurement is then obtained for each binned series of baseline data for both the insertion and withdrawal strokes. For generation of the baseline numbers, the average force measurements within the plateau regions 220 may be averaged over a number of cycles, for example, three cycles. As seen in FIG. 22, sampled force measurements are also obtained over the plateau regions 220 with the working instrument 30 being subject to a force on the distal end 34. Force measurements obtained over the binned insertion period are then averaged and subtracted from the average baseline force described above to produce an Update A value. The Update A value corresponds to the difference of the average forces obtained from the working instrument 30 under the insertion stroke with force applied and under insertion stroke with no force applied (i.e., baseline). Similarly, force measurements obtained over the binned withdrawal period are then averaged and subtracted from the average baseline withdrawal force described above to produce an Update B.

The estimated force on the distal end 34 of the working instrument 30 may then be calculated by the following formula:

$$\text{Force}_{Est.} = (\text{Update } A + \text{Update } B)/2 \quad (1)$$

Under this algorithm, Update A is determined at the completion of the insertion portion of the stroke while Update B is determined at the completion of the withdrawal portion of the stroke. For example, for a dithering rate of 2 Hz, the values (Update A or Update B) are updated about every ¼ second. Thus, as time progresses, Update A is updated, then Update B, then Update A, and so on and so forth. After each update step, the force value is re-calculated. It should be understood that a dither rate may be altered as needed. For example, in certain embodiments, the dither rate may vary between 0 Hz and about 10 Hz.

While the algorithm described above uses a single cycle differential average of selected portions of the waveforms obtained during a contact state and a non-contact state there are other ways of obtaining similar information. For example, the averages may be calculated over more than one cycle. In addition, the estimated force may be obtained by comparing the profile or shape of the measured waveforms when the working instrument is in a contact state (e.g., experiencing a force) with the measured waveform obtained in a baseline state (e.g., no force). For instance, other embodiments might consider waveform slope, representative of mechanical stiffnesses in the system, as an indicator for which portion of the waveform contains useful data (i.e., signal) and which portion of the waveform is superfluous (i.e., noise).

Figure 23:
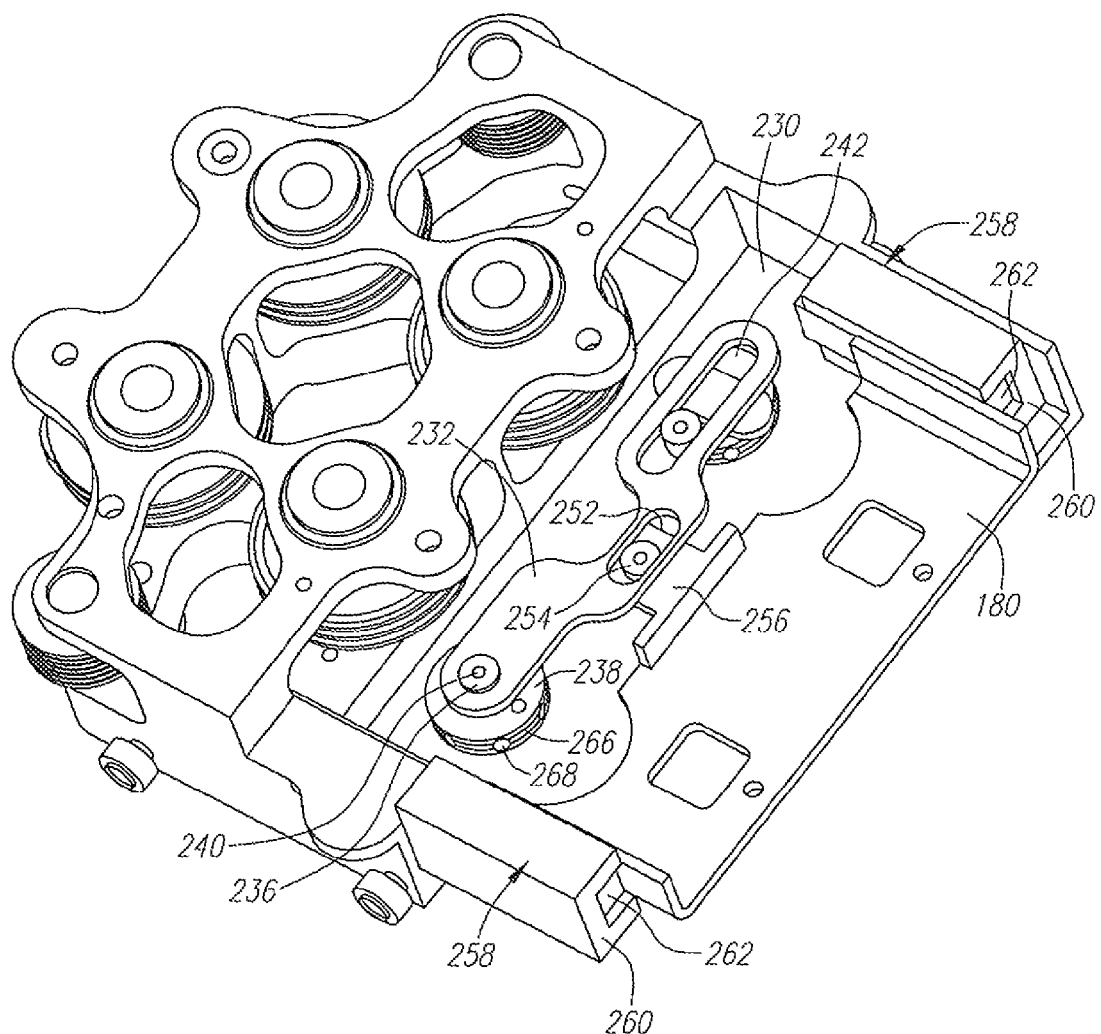
FIG. 23 illustrates a perspective view of a chassis for the robotic instrument system that holds the pivoting lever arm that moves the dither carriage back-and-forth in response to the cable-driven pulleys (cable not shown).
Figure 24:
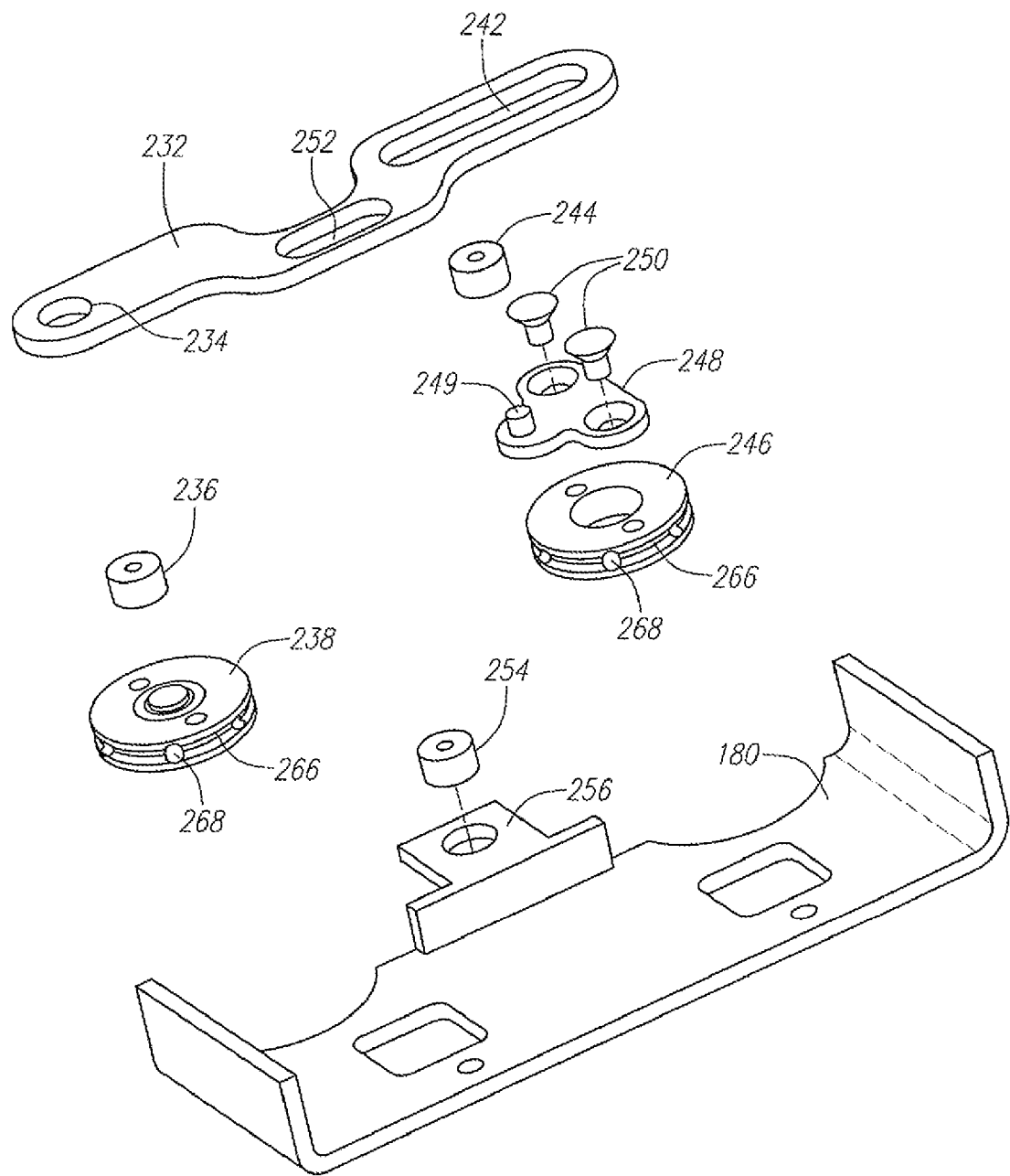
FIG. 24 illustrates an exploded view of the ditherer carriage and the lever arm components that is used to dither the dither carriage back-and-forth according to one aspect of the invention.

FIG. 23 illustrates a perspective view of a chassis 230 on which the guide splayer 14 (not shown) is mounted. FIG. 23 further illustrates the pivotable lever arm 232 that mechanically connected to the dither carriage 180. As best seen in FIGS. 23 and 24, the lever arm 232 includes a hole 234 for receiving a bearing 236 that is mounted to a surface (e.g., top surface) of a pulley 238. During the dithering operation, the lever arm 132 pivots about pivot point 240 which is the rotational axis of the bearing 236. The lever arm 232 further includes a slot 242 that traverses a portion of the length of the lever arm 232. The slot 242 is dimensioned to receive a bearing 244 mounted in an eccentric manner on a pulley 246. As best seen in FIG. 24, the bearing 244 is mounted in an eccentric or offset manner by using a cam 248 that is affixed to the upper surface of the pulley 246 by, for instance, screws 250. The cam 248 may be "T-shaped" and include a pin or shaft 249 on which the bearing 244 is mounted. Different cams 248 having different distances between the center of rotation of the pulley 246 to the pin 249 may be used to alter the degree of eccentricity. This, in turn, would alter the stroke distance of the mechanical ditherer 50.

Still referring to FIGS. 23 and 24, the lever arm 232 includes another slotted portion 252 in a central region of the lever arm 232. The slotted portion 252 is generally oriented longitudinally along the length of the lever arm 232. The slotted portion 252 is dimensioned to receive a bearing 254 this is rotationally mounted to the dither carriage 180. The bearing 254 may be positioned on a mount 256 that elevates a portion of the dither carriage 180.

As seen in FIG. 23, the dither carriage 180 is mounted to the chassis 230 using two crossed roller slides 258. The crossed roller slides 258 includes a base 260 that is fixedly secured to the chassis 230 and an inner slidable carriage 262 that is coupled to the dither carriage 180. A series of bearings or cylindrical steel rollers (not shown) enables the carriage 262 to glide, almost friction-free, over the base 260. For example, the cross roller slides 258 may be obtained from Del-Tron Inc., 5 Trowbridge Drive, Bethel, Conn. 06801 (model no. RD-1).

Figure 25:
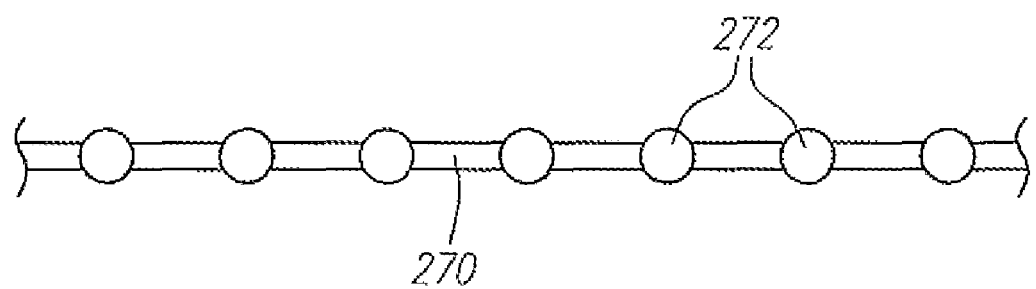
FIG. 25 illustrates a cable with crimp balls that is used to drive the ditherer according to one embodiment.

The pulleys 238, 246 used to drive the lever arm 232 include a circumferential groove 266 that is used to hold a drive cable 270 (shown in FIG. 25). The drive cable 270 may be formed from a bundle of numerous smaller wires formed from, for example, tungsten. As an example, the drive cable 270 may have an 8×19 construction formed from 152 wires having a diameter of 0.008" that results in a drive cable 270 having an overall diameter of around 0.018." The pulleys 238, 246 also include a plurality of recesses 268 that formed in the groove 266 and are used to mate with regular spaced crimp balls 272 that located along the length of the drive cable 270. The use of the crimp balls 272 along with the mating recesses 268 ensures that there will be no slippage between the drive cable 270 and the pulleys 238, 246 during the dithering process.

Figure 26:
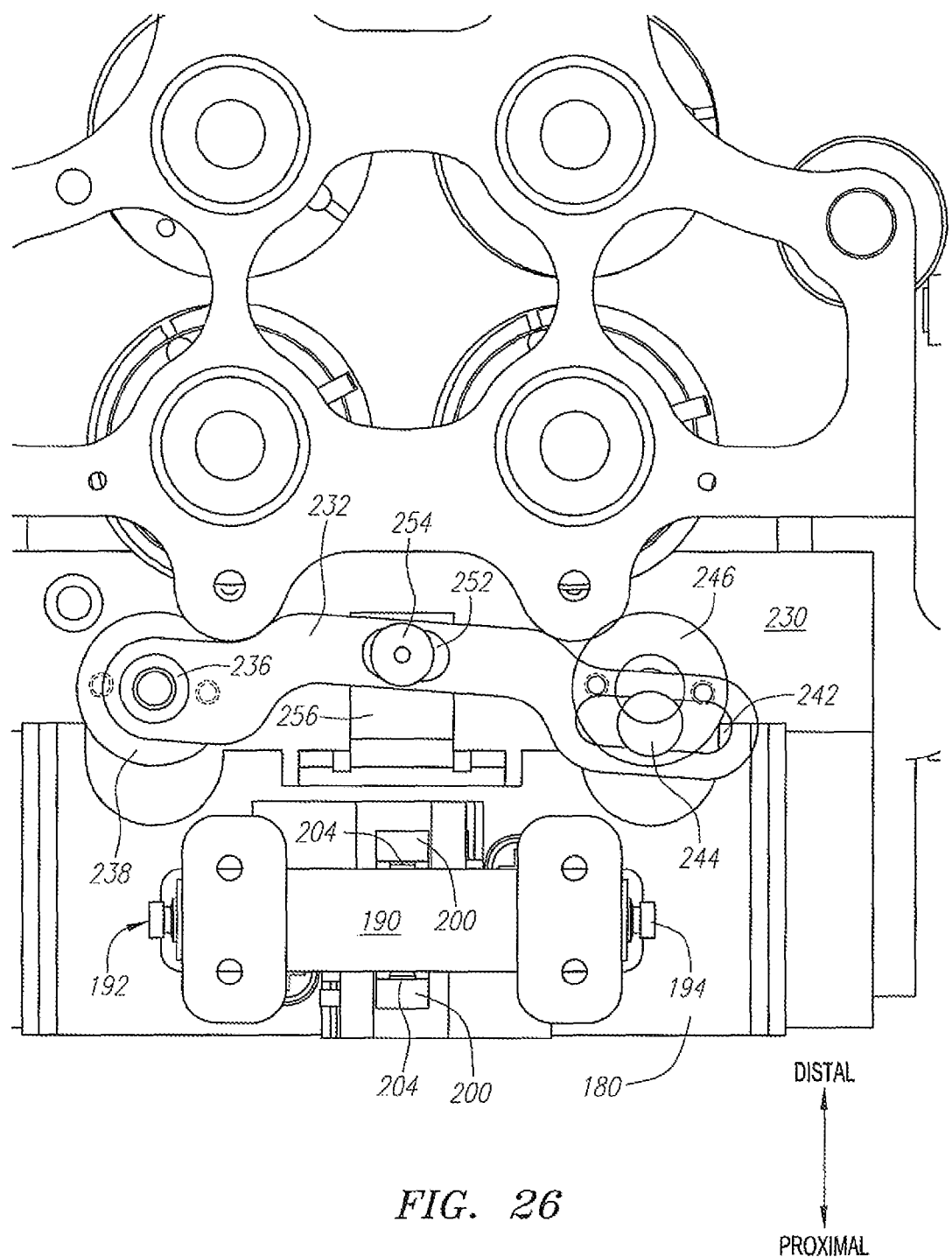
FIG. 26 illustrates a top-down plan view of the lever arm and mechanical ditherer mounted on the dither carriage. The lever arm is shown at or near the "six o-clock" position in which the mechanical ditherer is at the end of withdrawal or the beginning of insertion into the guide instrument.
Figure 27:
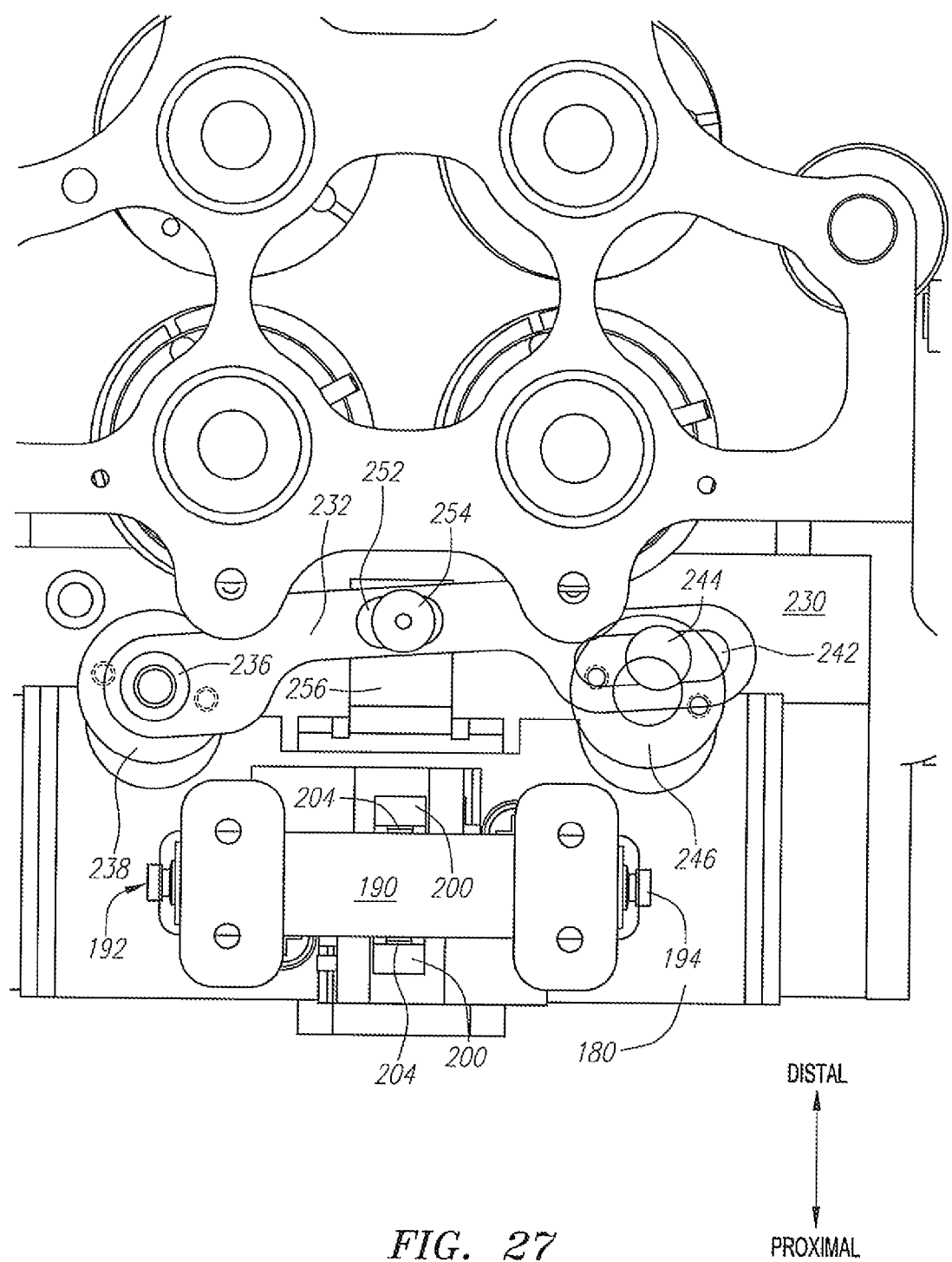
FIG. 27 illustrates a top-down plan view of the lever arm and mechanical ditherer mounted on the dither carriage. The lever arm is shown at or near the "twelve o-clock" position in which the mechanical ditherer is at the end of insertion or the beginning of withdrawal into the guide instrument.

FIGS. 26 and 27 illustrate top down plan views of the lever arm 232 and ditherer 50 as the lever arm 232 is pivoted back and forth in the withdrawal and insertion strokes. FIG. 26 illustrates the eccentrically offset bearing 244 in roughly a "six o'clock" position wherein the lever arm 232 is at or near the maximal displacement in the proximal direction. The lever arm 232 in FIG. 26 is thus at the beginning of the insertion stroke or, alternatively, the end of the withdrawal stroke. In contrast, FIG. 27 illustrates the eccentrically offset bearing 244 in roughly a "twelve o'clock" position wherein the lever arm 232 is at or near the maximal displacement in the distal direction. The lever arm 232 in FIG. 27 is thus at the beginning of the withdrawal stroke or, alternatively, the end of the insertion stroke.

Figure 28:
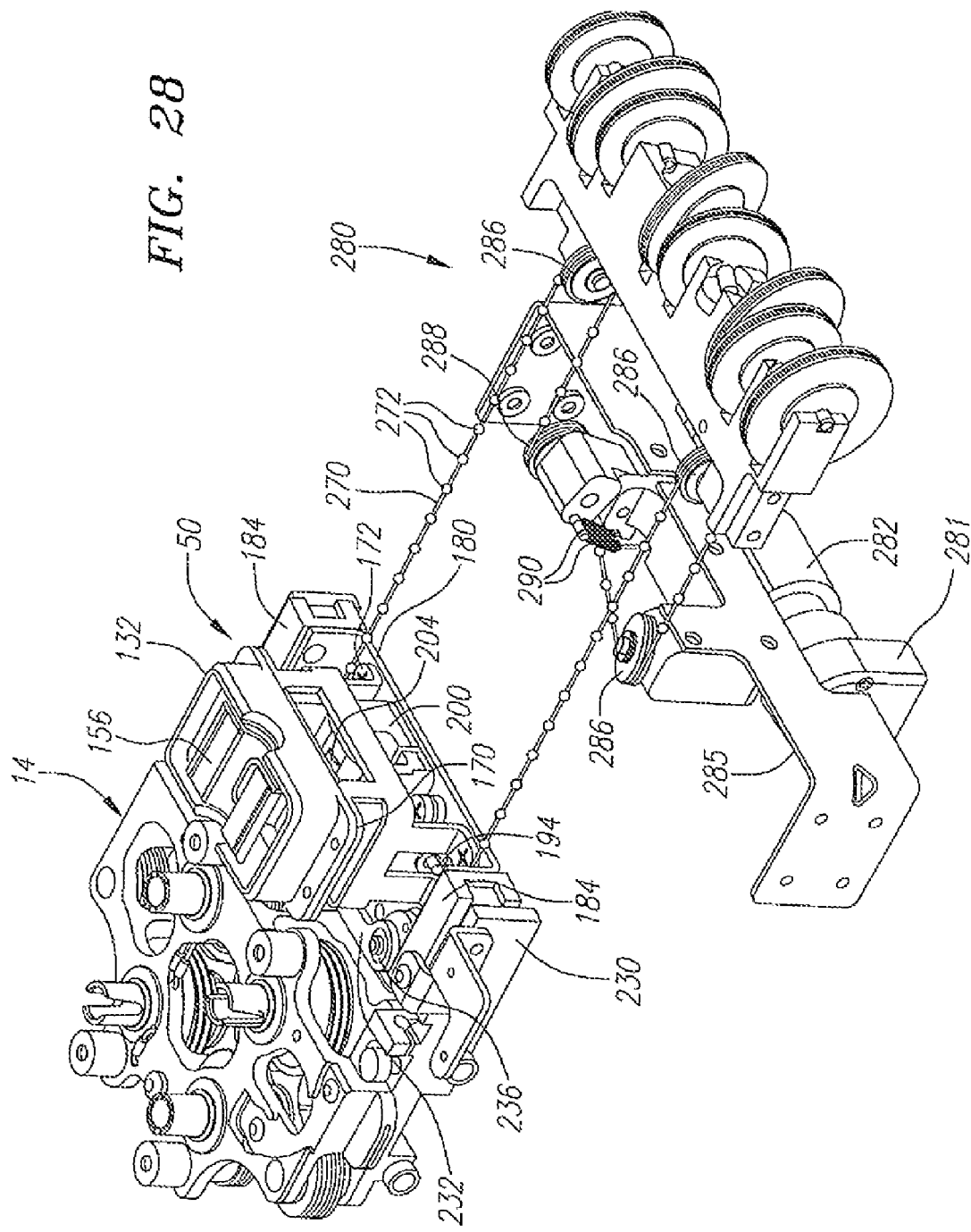
FIG. 28 is a perspective view of the motor-based drive system that uses a plurality of pulleys to pivot the lever arm back-and-forth to cause reciprocating motion in the ditherer.
Figure 29:
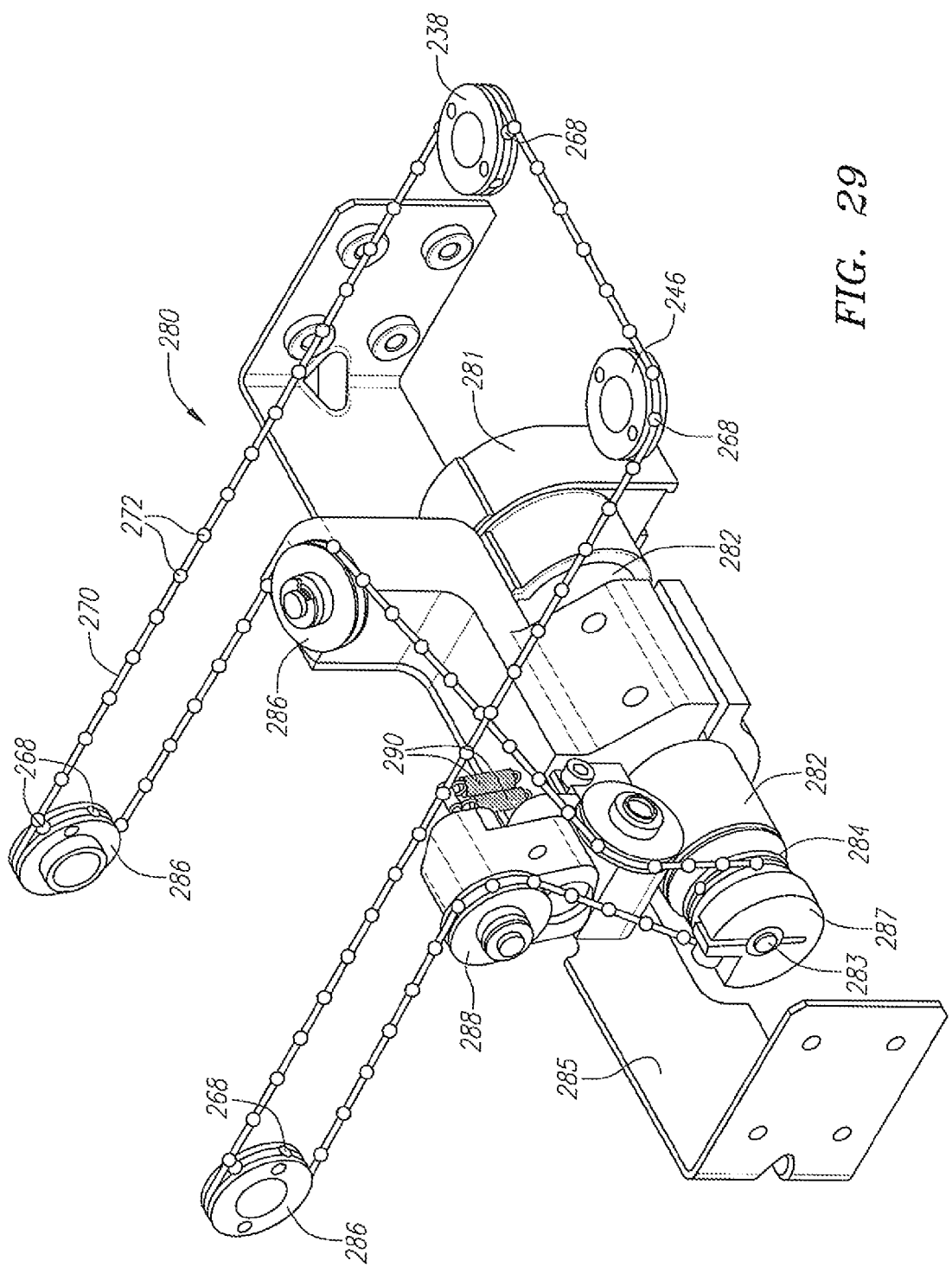
FIG. 29 is another perspective view of the drive system illustrated in FIG. 28.

Referring now to FIGS. 28 and 29, a motor driven pulley system 280 is used to pivot the lever arm 232 back and forth which, in turn, causes the reciprocating motion of the mechanical ditherer 50. As best seen in FIG. 29, the drive cable 270 is secured to a motor 282 having positioned thereon a drive pulley 284. The drive pulley 284 is secured to a shaft 283 of the motor using a clamp 287. The motor 282 is secured to, for example, a chassis 285 of the robotic instrument driver 400. The motor 282 may be mounted so as to be stationary with respect to the chassis 230 holding the lever arm 232. An encoder 281 is affixed to the backside of the motor 282 as seen in FIG. 29 and is used to accurately determine the position of the shaft 283 at any given point of time.

As seen in FIGS. 28 and 29, the drive cable 270 then passes through a series of proximally positioned pulleys 286. The pulley system 280 may also include a tensioning pulley 288 that is used to provide a biasing force, for example, via springs 290, to ensure that the drive cable 270 remains taught. The tensioning pulley 288 may be used to provide tension to the drive cable 270, for example, if the guide splayer 14 were moved longitudinally. As seen in FIGS. 28 and 29, the crimp balls 272 positioned along the length of the drive cable 270 ensure proper registration between the cable 270 and the various pulleys.

Figure 30A:
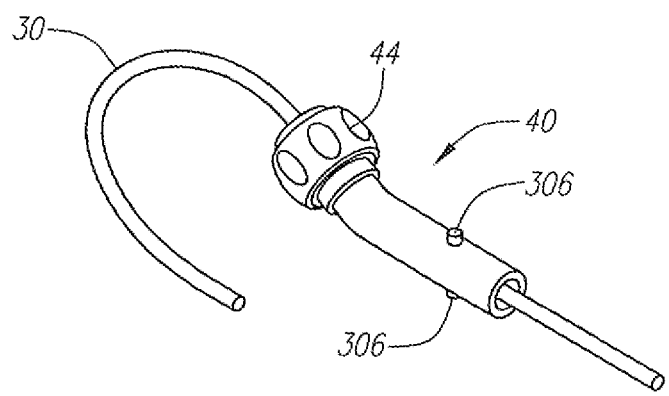
FIG. 30A illustrates a Touhy seal having a working instrument disposed therein.
Figure 30B:
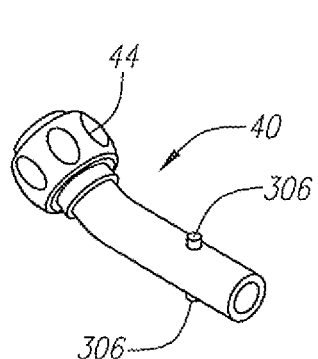
FIG. 30B illustrates another view of a Touhy seal.
Figure 30C:
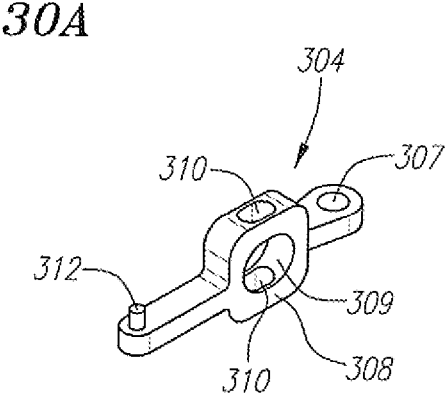
FIG. 30C illustrates a perspective view of a pivoting holder used as part of a mechanical ditherer according to one embodiment.
Figure 30D:
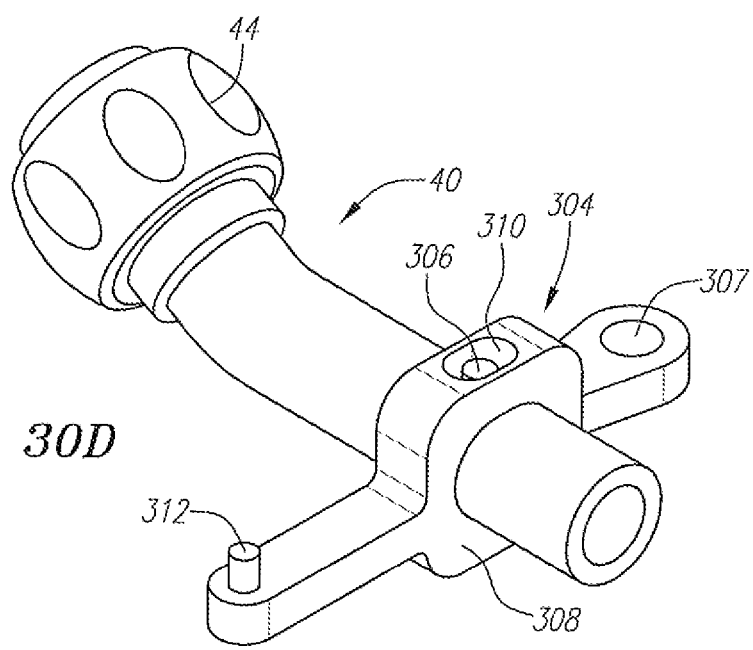
FIG. 30D illustrates the Touhy being inserted into the pivoting holder of FIG. 30C.
Figure 30E:
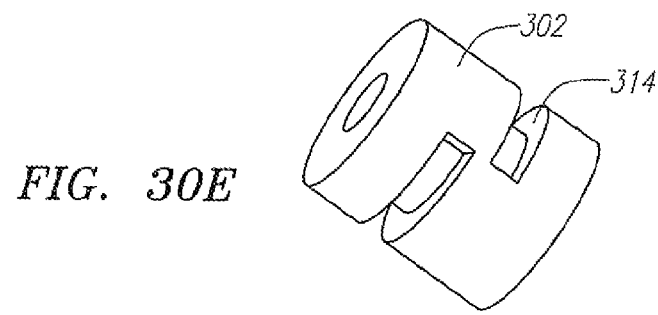
FIG. 30E illustrates a perspective view of a cam having a groove therein.
Figure 30F:
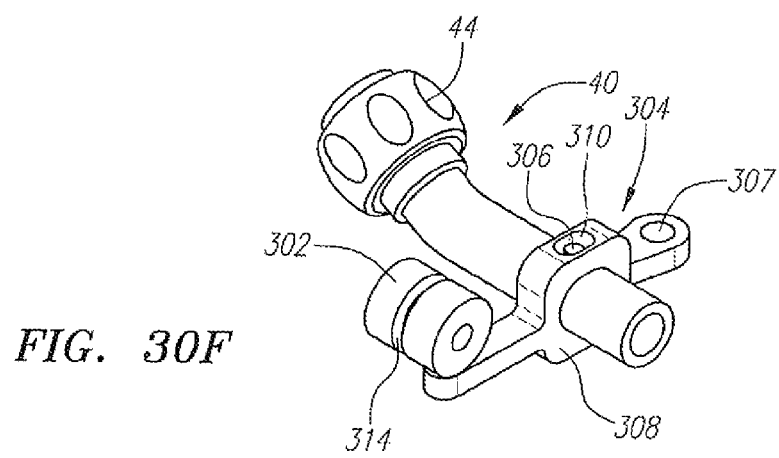
FIG. 30F illustrates the cam of FIG. 30E engaged with the pivoting holder of FIG. 30C.

FIGS. 30A-30G, and FIGS. 31-33 illustrate another embodiment of a mechanical ditherer 300. In this embodiment, a rotationally driven cam 302 (best seen in FIGS. 30E and 30G) is used to drive pivoting holder 304 that is secured to the guide instrument 30 and/or Touhy seal 40. FIGS. 30A and 30B illustrate a Touhy seal 40 that includes two tabs or detents 306 that are used to mate with the pivoting holder 304. FIG. 30C illustrates the pivoting holder 304 which includes a hole 307 at one end thereof that is used as the pivot point during operation of the mechanical ditherer 300. The holder includes a main body section 308 that includes an aperture 309 for the Touhy seal 40 along with recesses 310 for the tabs or detents 306. The recesses 310 serve to properly orient or register the Touhy seal 40 within the pivoting holder 304. The pivoting holder 304 further includes a pin 312 or other projection that is used to mate with a corresponding groove 314 located in the rotationally driven cam 302, as is shown in FIGS. 30E and 30F. The groove 314 is spirally cut into the main, cylindrically-shaped body of the cam 302. Different cams 302 having grooves 314 with varying degrees of pitch may be used to adjust the stroke of the ditherer 300.

Figure 30G:
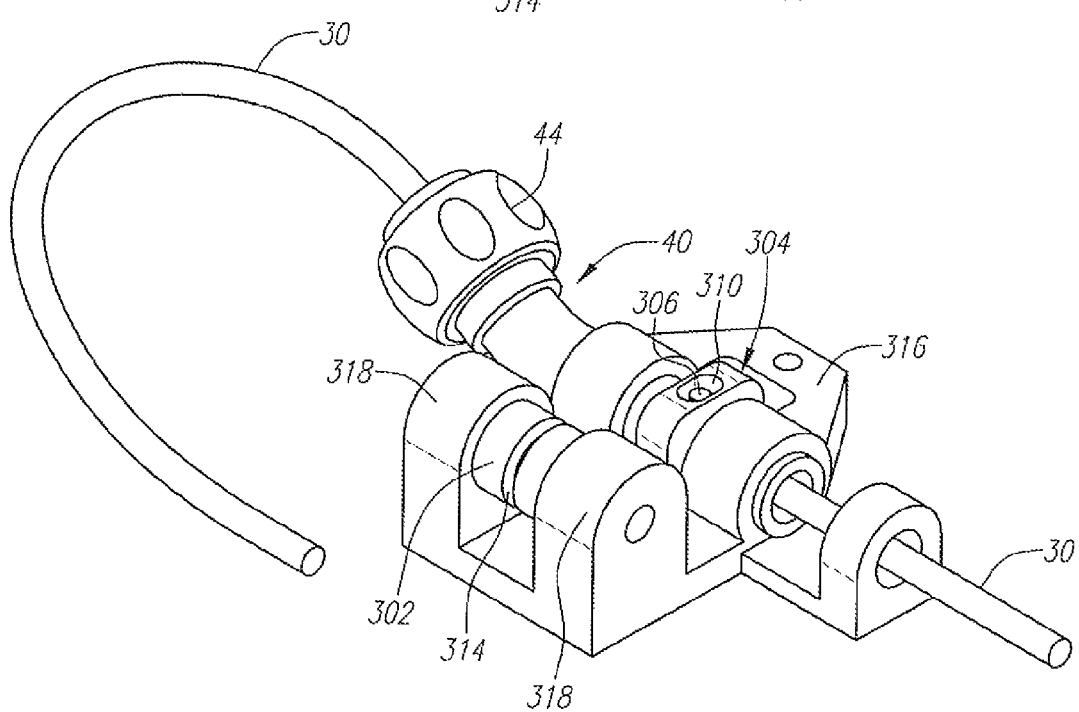
FIG. 30G illustrates a dither support block that holds the cam and pivoting holder. Also shown is a working instrument passing through the Touhy seal.

FIG. 30G illustrates the pivoting holder 304 and cam 302 contained in a dither support block 316. The pivoting holder 304 may be pinned to the dither support block 316 via the hole 307 so as to permit pivoting about the pivot point. The cam 302 is mounted via a shaft, axle, or the like to supports 318 on the dither support block 316. FIG. 30G further illustrates a portion of the working instrument 30 passing through the Touhy seal 40 that is positioned within the pivoting holder 304.

Figure 31:
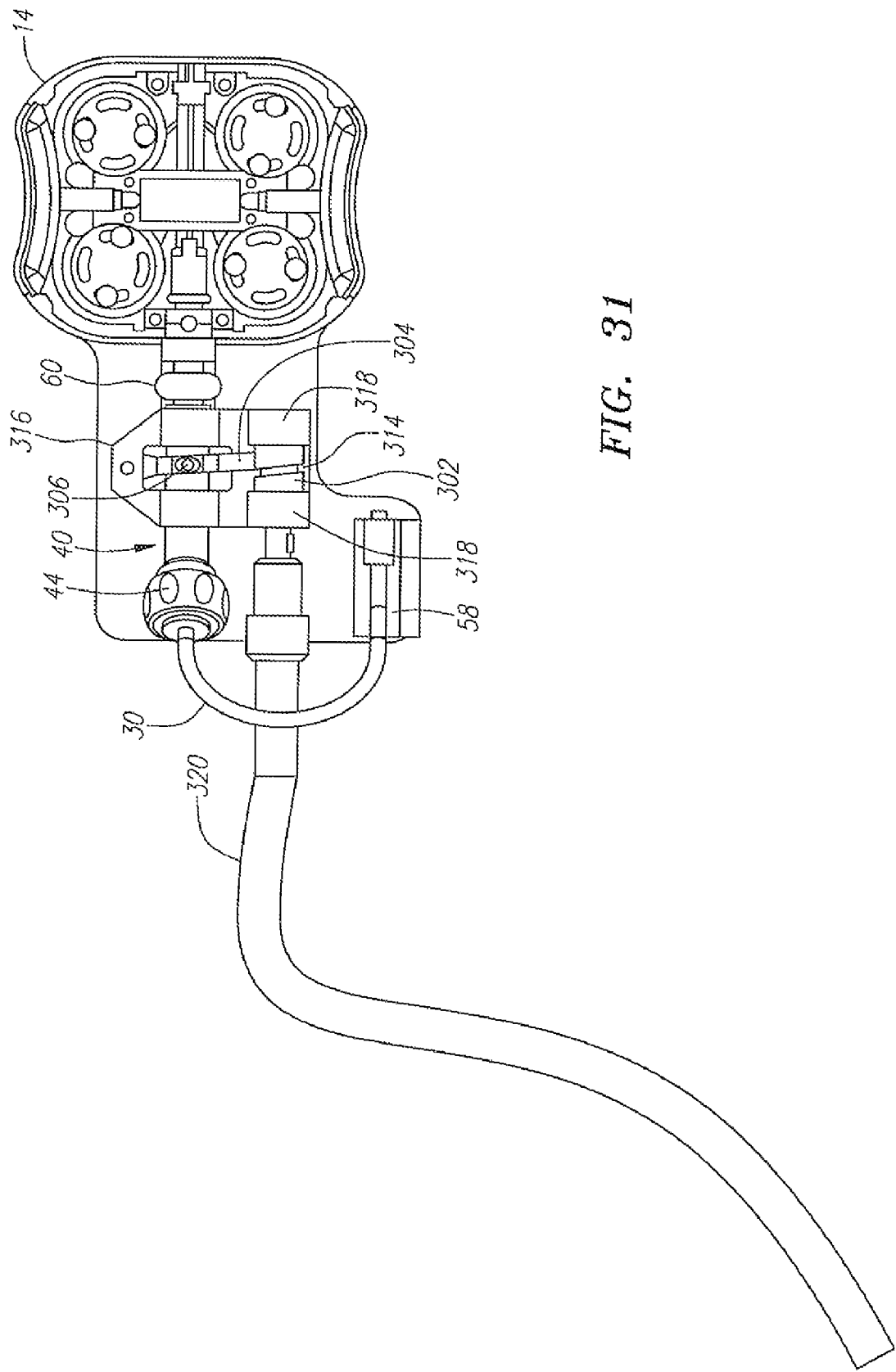
FIG. 31 illustrates a top down plan view of the guide splayer along with the mechanical ditherer embodiment illustrated in FIGS. 30A-30G. A drive cable is shown coupled to the cam. A flexible bellows is also illustrated that is connected to the Touhy seal.

FIG. 31 illustrates a top down view of the ditherer 300 being integrated into the guide instrument splayer 14. As seen in FIG. 31, the Touhy seal 40 may be secured at a distal end to a flexible bellows 60. The other end of the bellows 60 may be coupled to the guide instrument 4. Also shown in FIG. 31 is a drive cable 320. The drive cable 320 is connected at a proximal end to a motor, servo or the like (not shown) to power the ditherer 300. The motor or servo may be located on-board the robotic instrument driver 400 or off-board. The drive cable 320 may include, for example, a bicycle cable that is rotationally driven back and forth. Rotational movement of the drive cable 320 may be translated to the cam 302 which, in turn, causes the pivoting holder 304 to pivot back and forth. In one aspect, the groove 314 is cut in such a manner (e.g., sinusoidal wave) that the cam 302 is rotated in a single direction to cause the back and forth movement of the pivoting holder 304. In this regard, the drive cable 320 may be driven in a single direction. In another embodiment, the driven cable 320 may be driven in different directions to cause the cam 302 to rotate in different directions (e.g., clockwise then counter-clockwise).

Figure 32A:
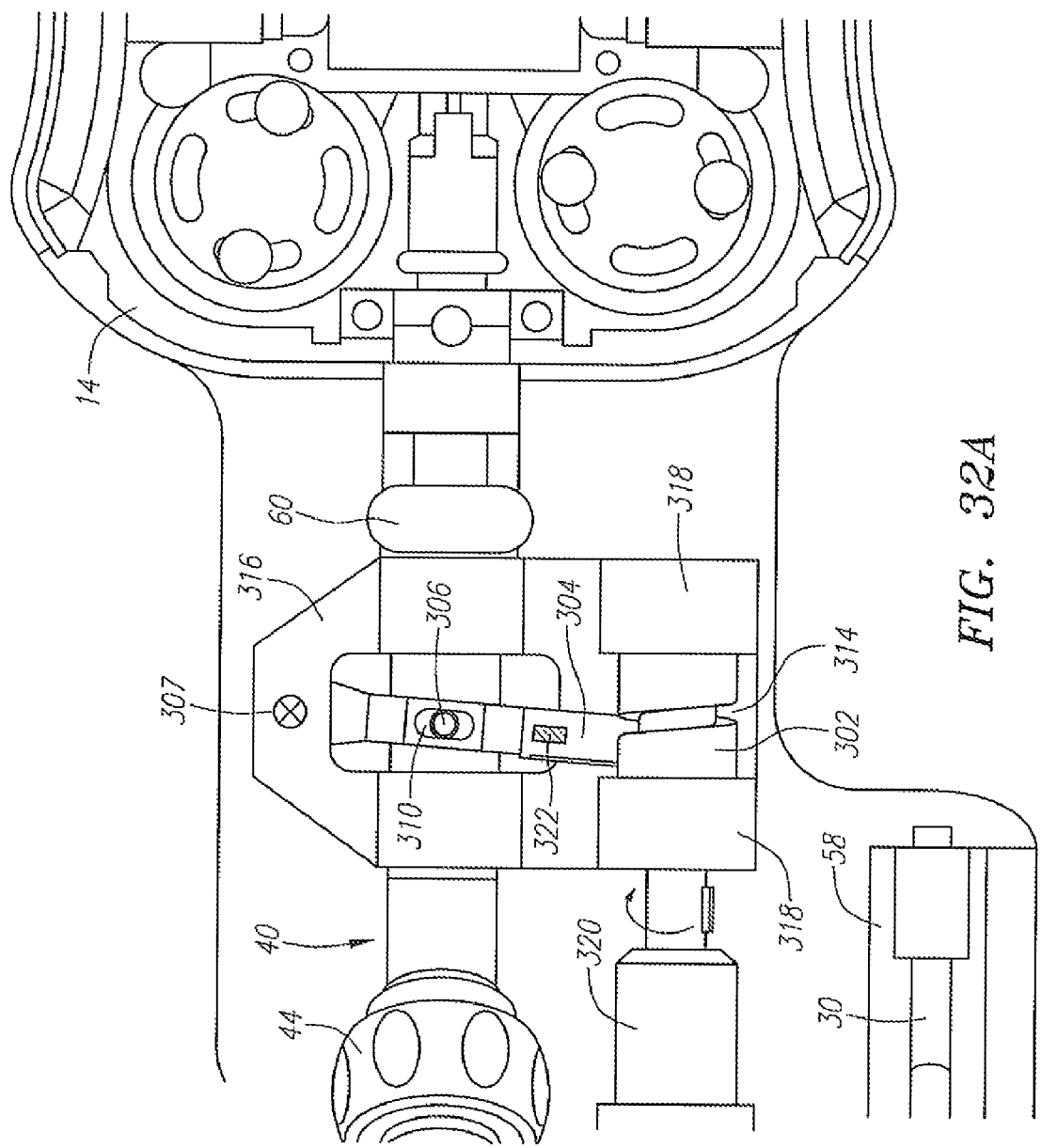
FIG. 32A is an enlarged, top down plan view of the mechanical ditherer illustrated in FIGS. 30A-30G and FIG. 31. A strain gauge is shown on the pivoting holder.
Figure 32B:
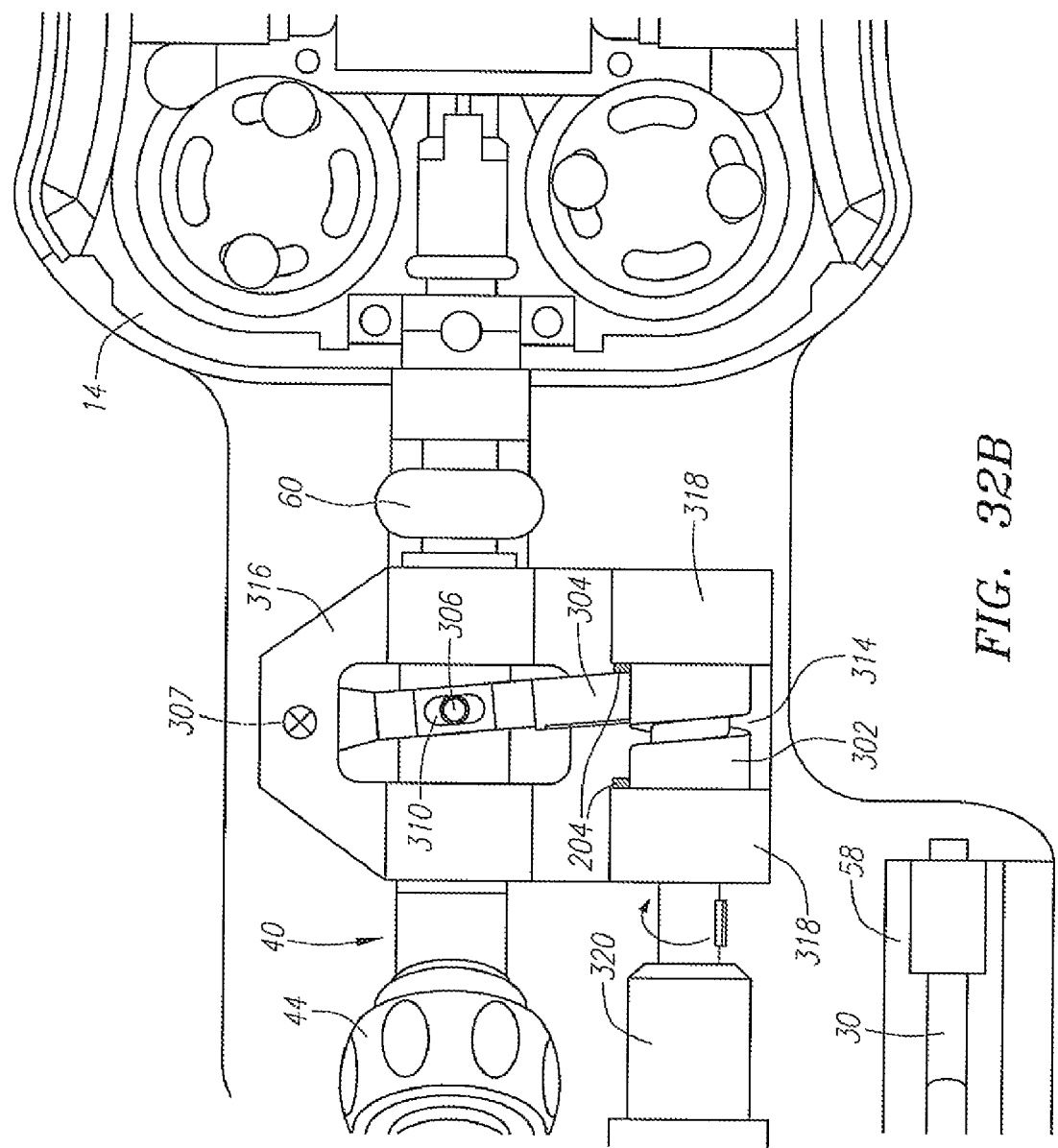
FIG. 32B is an enlarged, top down plan view of the mechanical ditherer illustrated in FIGS. 30A-30G and FIG. 31. In this embodiment, two opposing force sensors are affixed to the supports on either side of the pivoting member.

FIGS. 32A and 32B illustrate a magnified view of the ditherer 300 and its components as it dithers in and out. The pivoting holder 304 pivots and follows the groove 314 in the cam 302 via the mechanically linked pin 312 (obscured from view). In this embodiment, the Touhy 40 is thus moved back and forth along with the pivoting holder 304. Because the working instrument 30 is also securely fastened to the Touhy 40, the working instrument 30 also is dithered back and forth. In order to measure the insert and withdrawal forces, a strain gauge 322 may be mounted to the pivoting holder 304 to measure stresses therein so the force on the distal end 34 of the working instrument 30 can be calculated, for example, in the manner described herein.

FIG. 32B illustrates another embodiment for measuring force. In this embodiment, force sensors 204 are disposed on opposing sides of the supports 318 of the dither support block 316. The force sensors 204 may include unidirectional force sensors as described herein. In the embodiment illustrated in FIG. 32B, there may be a dead band zone when the pivoting holder 304 is not contacting either force sensor 204. The displacement of the pivoting holder 304 as well as the distances between the force sensors 204 may be engineered to minimize this dead band zone.

Figure 33A:
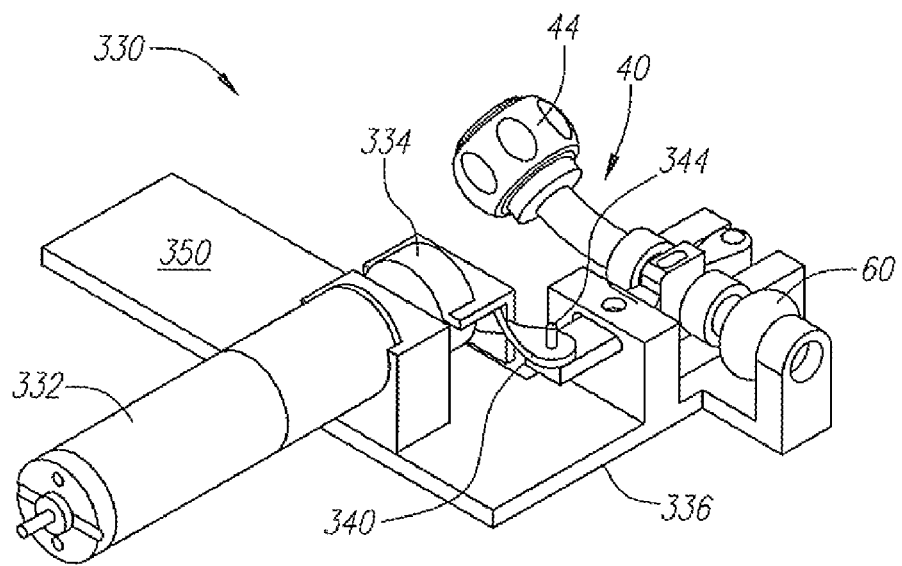
FIGS. 33A and 33B illustrate perspective views of a mechanical ditherer according to another embodiment.
Figure 33B:
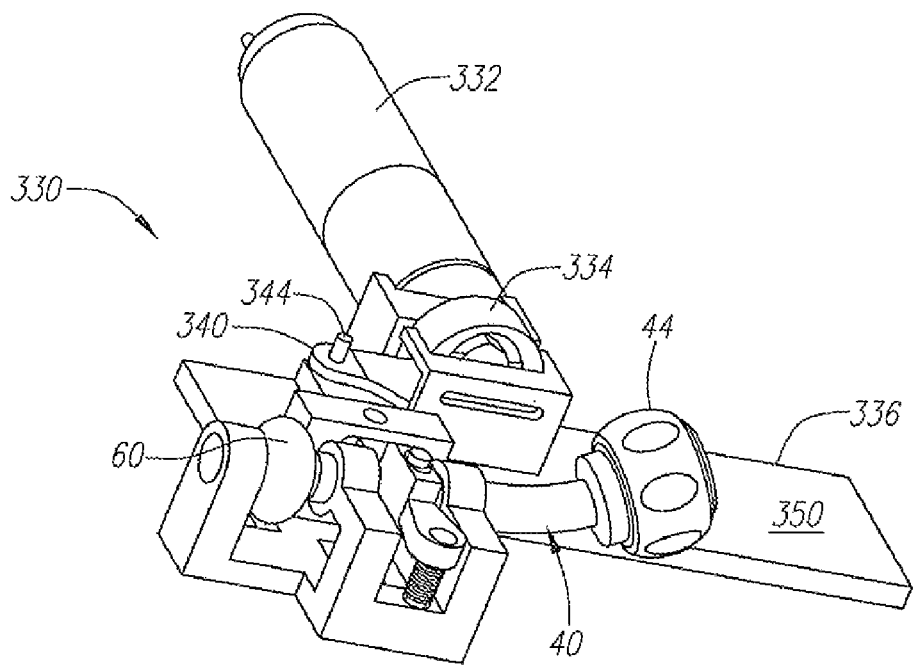

FIGS. 33A-33G illustrate another embodiment of a mechanical ditherer 330. In this embodiment, a dither assembly 336 includes an electric motor or servo 332 that is used to directly drive a cam 334. The direct drive motor 332 is mounted to a base 350. The electric motor 332 directly engages with a cam 334 that has a heart-shaped machined slot 338 as illustrated in FIGS. 33C and 33E. A drive linkage 340 interfaces with the cam 334 via a pin 342 (best seen in FIG. 33E) that travels in the cam slot 338. The opposing end of the drive linkage 340 contains a pin 344 that engages with the pivoting holder 346 that is secured to the Touhy seal 40. In this embodiment, as the electric motor 332 turns, the motor drives the cam 334, causing the pivoting holder 346 to pivot about its pin 348 (FIG. 33B) and translate back and forth to effectuate the dithering motion. FIG. 33G illustrates a base 350 that is used to support the various components of the dither assembly 336. Force measurements may be obtained using either a strain gauge or one or more force sensors as described in the previous embodiment.

Figure 34A:
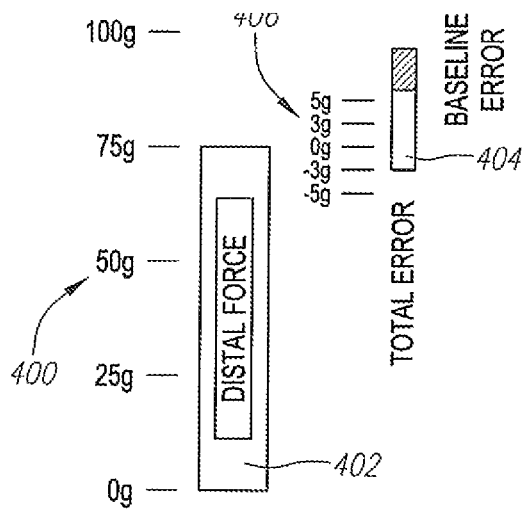

FIGS. 34A-34D illustrate various embodiments of how the estimated force at the proximal end 34 of the working instrument 30 is displayed to the physician or user. In one aspect, a force scale 400 is displayed on, for instance, a display 90 (e.g., FIGS. 3 and 4) associated with the operator control station 82. The force scale 400 may include a number of gradations positioned at regular intervals. For instance, FIG. 34A illustrates a force scale ranging from 0 grams to 100 grams of force with gradations every 25 grams. In one aspect, the user may control the scaling of the force scale 400 via a button, switch, menu or the like at the operator control station 82. As seen in FIG. 34A, the magnitude of the estimated force at the distal end 34 of the working instrument 30 at any particular point in time is displayed via a bar 402. The bar 402 rises or falls as the force dynamically changes. Advantageously, the bar 402 is displayed in real-time or near real time as often as the algorithm described herein is updated. Still referring to FIG. 34A, a visual cue 404 indicative of the estimated error in the measured force is also displayed alongside the estimated force. In FIG. 34A, the visual cue 404 may include an error bar that is displayed alongside its own force scale 406 that indicates the amount of error associated with the particular measurement. As seen in FIG. 34A, the error bar 404 combines total error with the baseline error on a single force scale 406. The visual cue 404 may be updated in real-time or near real-time as the algorithm is updated. The system may be programmed such that if the baseline error goes above a pre-determined threshold value, the user is prompted to re-baseline the device.

Figure 34B:
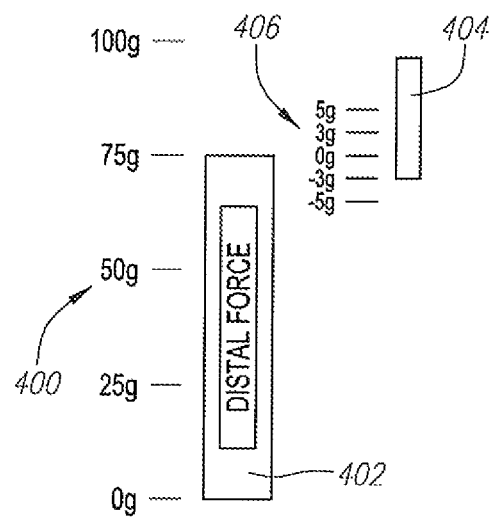
Figure 34C:
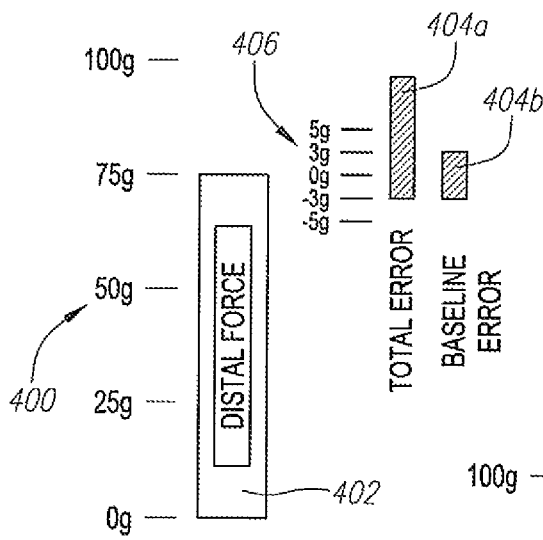
Figure 34D:
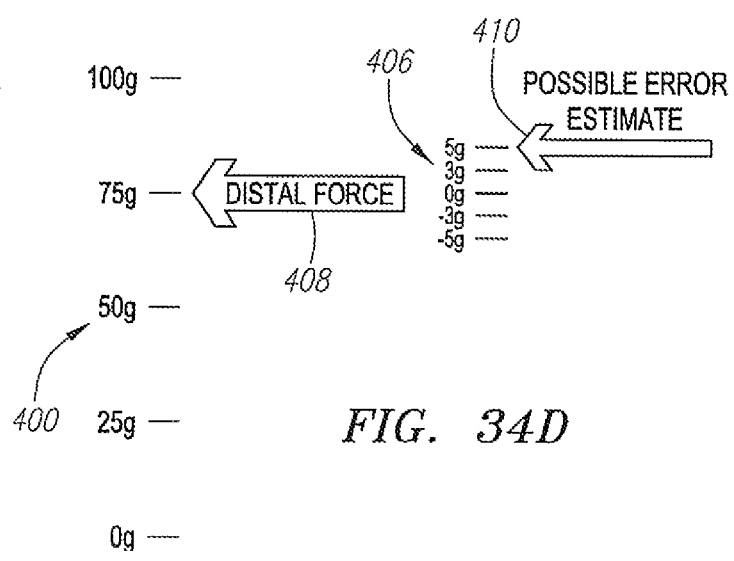

FIG. 34B illustrates an embodiment like that disclosed in FIG. 34A with the difference being that only total error is displayed on the error bar 404 adjacent to the force scale 406 associated with the error visual cue 404. FIG. 34C illustrates another embodiment in which the baseline error and total error are displayed as separate error bars 404a, 404b. FIG. 34D illustrates still another embodiment in which a pointer 408 which, for example, is the form of an arrow or the like is used to display the estimated force. The pointer 408 dynamically moves up and down as force is applied to the distal end 34 of the working instrument 30. In one aspect, the pointer 408 may get larger as the force increases and, conversely, may get smaller as the force decreases. Also, the pointer 408 may change color as the force dynamically changes. For example, the pointer 408 may appear to have a "hot" color (e.g., red) if the estimated force is relatively high. In contrast, if there were little or no force experienced by the working instrument 30, the color may be a "cool" color (e.g., blue). An intermediate level of force may be shown using a medium color such as, for instance, yellow. In this regard, the physician is given an extra visual cue as to the forces experienced by the working instrument 30. FIG. 34D also illustrates a pointer 410 that is used to display the estimated error in the force measurement. Like the force measurement pointer 408, the error pointer 410 dynamically moves as the error changes. The error pointer 410 may also change color in response to the degree of error. The estimated error may be displayed as a force (e.g., grams) or it may be displayed as a percentage or degree of deviation.

The estimated error that is displayed to the physician is based on a number of parameters that are empirically determined. For example, the estimated error may be based on the angle of the sheath 6, articulation angle, rate of change of articulation angle, insertion distance, peak-to-peak forces, as well as the magnitude of the forces applied to the distal end 34 of the working instrument 30. The estimated error may also be a function of the type or model of working instrument 30 that is used. This information may be gathered and input via the operator control station 82. Information pertaining to the type of working instrument 30 as well as the empirical data may be stored in a memory or look up table that can then be compared with measured force values to output an estimated error.

Other methods for displaying force may include using a sound where the tone, pitch, or volume varies according to the measured force. Additionally, an audible warning may sound if a force reading (or a series of readings) reach a pre-determined, unsafe level. A warning light or graphical element 96 (e.g., as shown in FIG. 1) or other type of alert such as a warning dialogue box can indicate when the force reaches unsafe levels. Haptic feedback can also indicate force increases so that as force readings increase, proportional force is felt on the master controller 104 at the operator control station 82. A vibrational warning may be sent through the master controller 104 so that the physician feels a vibration when force levels have become unsafe.

Figure 35:
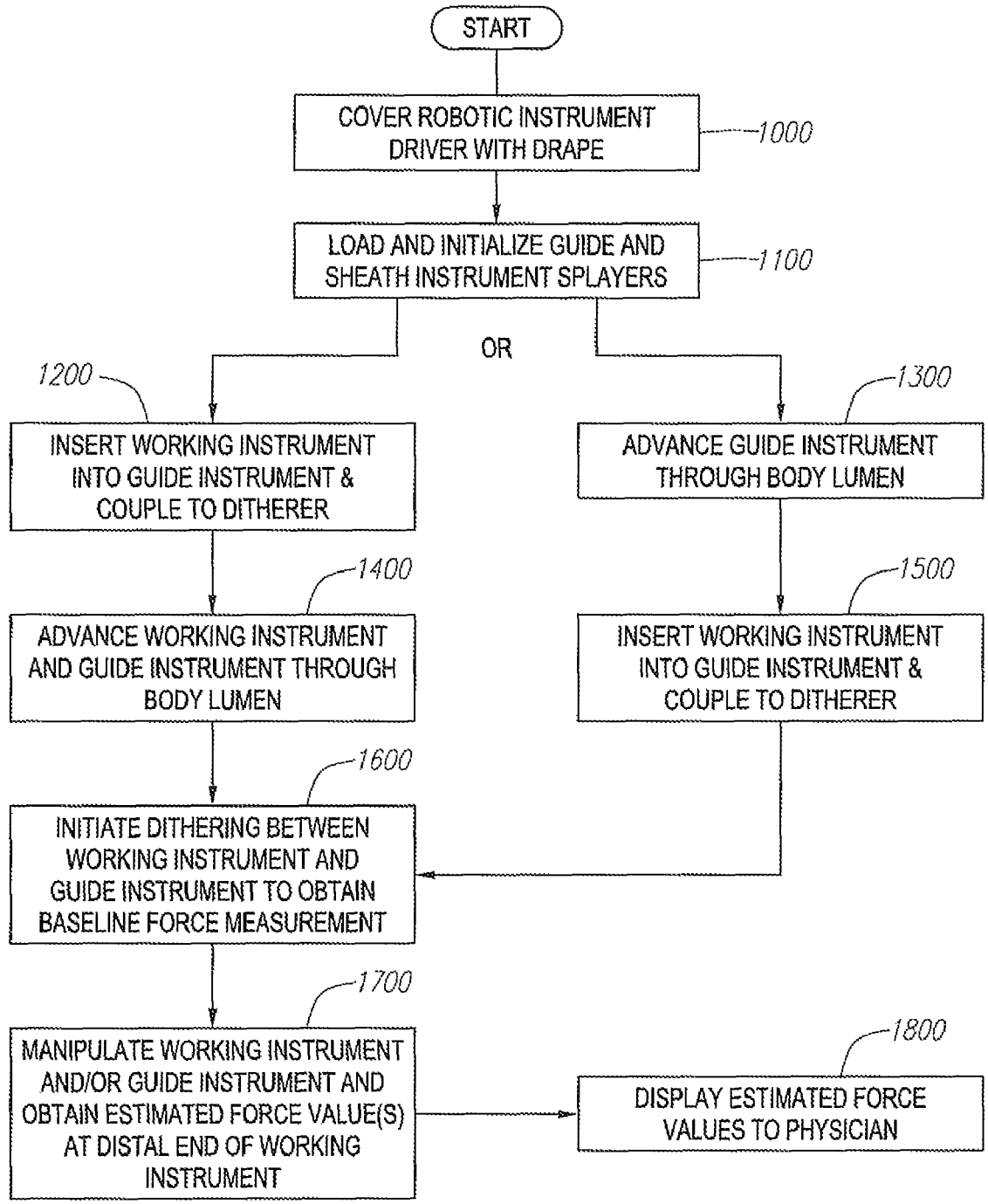
FIG. 35 illustrates a process flow diagram for operating a robotic instrument system according to one embodiment.

With reference to FIG. 35, in a typical use of the device, the robotic instrument driver 400 is first mounted (step 1000) with the drape 130 as illustrated, for example, in FIG. 11. The guide and sheath instrument splayers 14, 16 are loaded onto the robotic instrument driver 400 and initialized as illustrated in step 1100. In one aspect of the method, as illustrated in step 1200 of FIG. 35, the working instrument 30 is loaded onto the robotic instrument system 2 and coupled to the ditherer 50 prior to inserting and/or advancing (step 1400) the guide instrument 4 and sheath instrument 6 into a body region (e.g., blood vessel) of the patient. Alternatively, as illustrated in step 1300 of FIG. 35, the guide instrument 4 and sheath instrument 6 may first be inserted into the body region of interest so as to place the distal tip of the guide instrument 4 near or adjacent to the region or site of interest. As seen in step 1500 in FIG. 35, the working instrument 30 may then be back loaded through the seal 40 an into the guide instrument 4 until the distal end 34 projects at least partially from the distal end of the guide instrument 4. A flushing fluid like pressurized saline may be pumped or forced in between the working instrument 30 and guide instrument 4 to reduce friction and prevent retrograde flow through the device. Similar flushing fluids may be delivered between the guide instrument 4 and the sheath instrument 6.

To use to force sensing feature of the robotic instrument system 2, the physician or user may enable this functionality by, for example, pressing a button 103a (FIG. 4) or by using the graphical user interface (GUI) located at the operator control station 82. The graphical user interface (GUI) may include a touch screen 100 or another input device such as mouse, keyboard, pencil, pointer, or the like. Initiation of the force sensing feature causes, for example, the mechanical ditherer 50 to move back and forth and described herein. First, an initialization sequence is performed to establish a baseline. The process is represented as step 1600 in FIGS. 35 and 36. The system may prompt the physician or user to verify (e.g., step 2000 in FIG. 36) that the distal end 34 of the working instrument 30 is not contacting any objects (e.g., tissue, other instruments, etc.). For example, a message may be displayed on the display 90 associated with the operator control station 82.

In one aspect of using the system described herein, the guide instrument 4/sheath instrument 6 and working instrument 30 undergo the baseline process at an articulation position that closely approximates the articulation that will be used during the diagnostic or therapeutic procedure. For example, the guide instrument 4 with the working instrument 30 may be articulated into position in which the distal end of the working instrument 30 may contact a surface. The guide instrument 4 and or sheath instrument 6 subsequently may be retracted proximally to ensure that the distal end 34 of the working instrument 30 is free of tissue or other objects. Optionally, ECG or other diagnostic modalities may be used to confirm that the distal end 34 of the working instrument 30 is indeed free of any contact with tissue. Once the physician is confident that the distal end 34 is free from any contact with tissue or objects, the physician may then baseline the system by, for example, pressing a button 103b (FIG. 4) or by using the graphical user interface (GUI) located at the operator control station 82. The baseline is then taken and stored as illustrated in step 2100 of FIG. 36 for use in subsequent processing according to the algorithms described in detail herein.

If an unacceptable baseline measurement is taken, for example, if the system detects forces indicative of touching with a surface or object, the physician may be prompted with a warning that requests confirmation of the current baseline. For instance, a warning such as "There are indications that you are touching tissue. Are you sure you want to proceed?" may be displayed to the physician on the display 90. The physician may then re-baseline the system or, alternatively, accept the current baseline. Once an acceptable baseline has been accepted by the physician, the guide instrument 4 and/or sheath 6 and working instrument 30 may be manipulated by the physician (step 1700 in FIG. 35) and the estimated force experienced at the distal end 34 of the working instrument 30 is preferably displayed (step 1800 in FIG. 35) to the physician. In addition, a visual cue 404 or pointer 410 of the estimated error may also be displayed as described herein with respect to FIGS. 34A-34D.

The physician continues with the operation as desired with real-time or near-real time display of the estimated contact forces experienced by the distal end 34 of the working instrument 30. For example, the procedure may include mapping heart tissue using a mapping catheter as a working instrument 30. Alternatively, the procedure may include the ablation of tissue using an ablation catheter as a working instrument 30. While these two specific examples of procedures have been described herein it should be understood, that the system is not limited to the particular diagnostic or therapeutic procedure performed by the working instrument 30.

Figure 36:
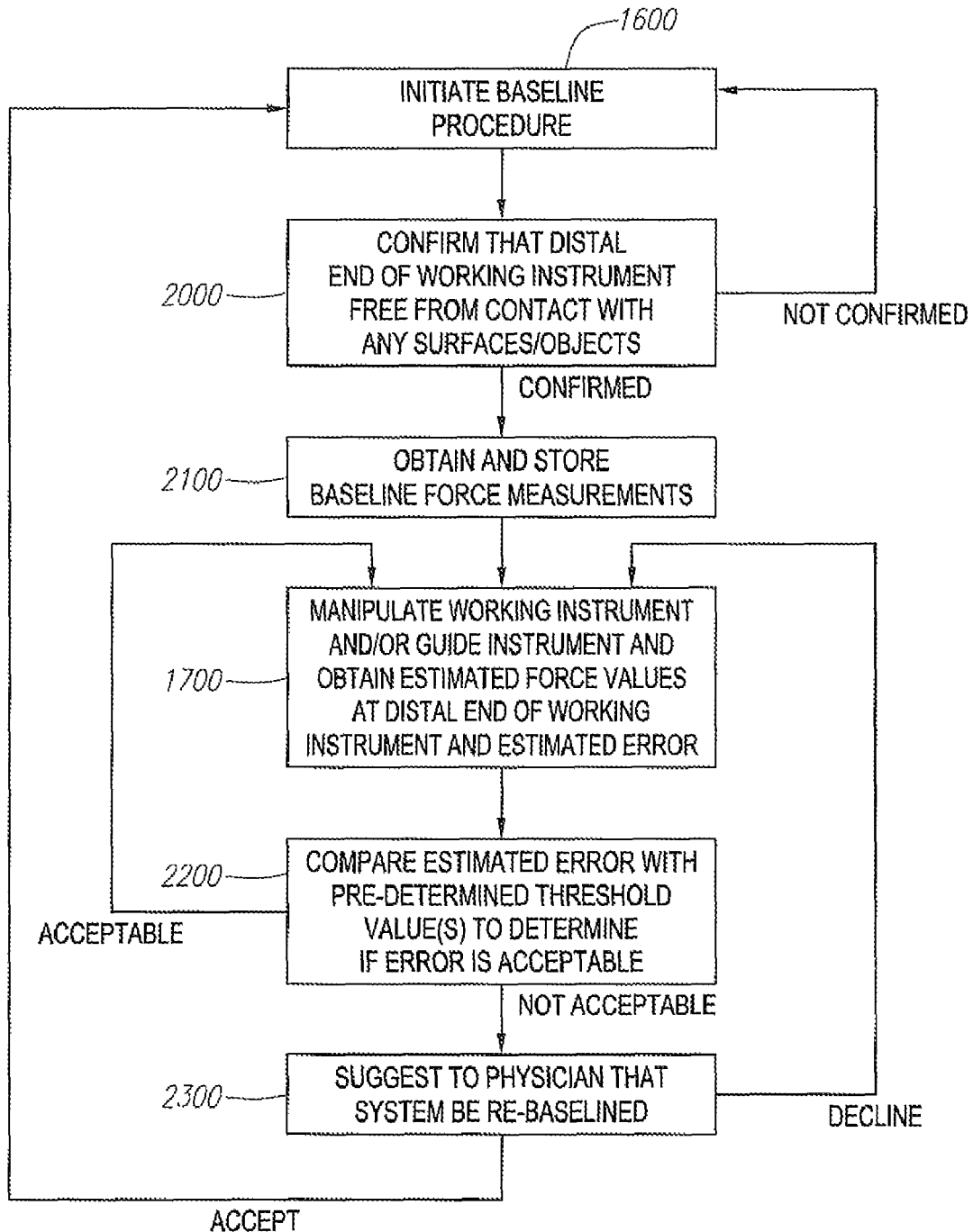
FIG. 36 illustrates a process flow diagram for operating a robotic instrument system according to another embodiment.

During the procedure, the computer(s) 118 or other processors operatively coupled to the robotic instrument system 2 may track the position and/or orientation of the guide instrument 4, sheath instrument 6, and working instrument 30 so that the physician may be prompted to re-baseline if the articulation meets or exceeds a pre-determined threshold value that has been established for movement of the guide 4 instrument and/or sheath instrument 6. As explained with respect to FIG. 1A, the articulation of the guide instrument 4, sheath instrument 6, and working instrument 30 may be visualized by the physician on a display 90. The underlying articulation data may optionally be displayed as well. Likewise, as illustrated in step 2200 of FIG. 36, if the error associated with a particular force measurement is too large (e.g., above a pre-determined threshold value), the system will prompt or suggest (step 2300) the physician to re-baseline the system. For example, a message may be displayed on the display 90 or an audible tone or alarm may sound when the error becomes too large. In one aspect, the system may automatically retract the guide instrument 4, sheath instrument 6, and working instrument 30 when the upper error limit is reached or surpassed. This procedure would forcibly require the physician to re-baseline. Of course, as illustrated in FIG. 36, the prompt or suggestion made to the physician may be advisory and the physician may choose to ignore or disregard the suggestion made by the system and continue with the manipulation of the working instrument 30, guide instrument 4 and/or sheath 6 instrument.

While embodiments of the present invention have been shown and described, various modifications may be made without departing from the scope of the present invention. The invention, therefore, should not be limited, except to the following claims, and their equivalents.

What is claimed is:

1. An apparatus for sensing forces applied to a distal end of a robotically controlled flexible working catheter, comprising:
    a robotically controlled guide catheter configured for insertion into a body lumen of a patient, the robotically controlled guide catheter comprising a flexible, steerable catheter including a lumen extending from a proximal end to a distal end;
    the robotically controlled flexible working catheter disposed in the lumen of the robotically controlled guide catheter, the robotically controlled flexible working catheter including a distal end that projects distally from the distal end of the robotically controlled guide catheter, the robotically controlled flexible working catheter including a proximal region extending proximally from the robotically controlled guide catheter;
    a ditherer operatively connected to the proximal region of the robotically controlled flexible working catheter for moving the robotically controlled flexible working catheter in a relatively rapid, reciprocating or oscillatory motion relative to the robotically controlled guide catheter; and
    at least one force sensor for measuring the forces applied to the robotically controlled flexible working catheter by the ditherer.

2. The apparatus of claim 1, wherein the at least one force sensor comprises two force sensors.

3. The apparatus of claim 2, wherein the two force sensors are disposed on opposing sides of the ditherer.

4. The apparatus of claim 3, wherein the two force sensors comprise compression force sensors.

5. The apparatus of claim 4, further comprising a computer configured for calculating an estimated force based at least in part on the obtained force measurement for at least one dither cycle.

6. The apparatus of claim 5, further comprising a monitor for displaying the estimated force.

7. The apparatus of claim 1, wherein the proximal region of the robotically controlled flexible working catheter is sealed from the lumen of the robotically controlled guide catheter via a fluid-tight seal.

8. The apparatus of claim 7, wherein the seal comprises a Touhy seal.

9. The apparatus of claim 7, wherein the seal is connected to a flexible bellows.

10. The apparatus of claim 1, wherein the ditherer comprises a moveable ditherer carriage and a load sensing member pivotally mounted with respect to the ditherer carriage.

11. The apparatus of claim 10, wherein the ditherer carriage includes opposing load cell holders disposed on opposing sides of the load sensing member, each holder containing a compression force sensor.

12. The apparatus of claim 10, further comprising a clamp on the load sensing member, the clamp being configured to secure the working catheter.

13. The apparatus of claim 10, further comprising a clamp for securing a handle of the working catheter.

14. The apparatus of claim 1, further comprising a removable drape for covering at least a portion of the robotically controlled guide catheter.

15. The apparatus of claim 7, further comprising an inlet port in communication with the lumen of the guide catheter, the inlet port being configured to receive a pressurized saline solution.

16. The apparatus of claim 1, wherein the robotically controlled guide catheter comprises a robotically operated inner guide catheter surrounded at least in part by a robotically operated outer sheath.

17. The apparatus of claim 16, wherein the robotically controlled guide catheter is connected to a guide catheter splayer.

18. The apparatus of claim 16, wherein the robotically controlled sheath is connected to a sheath splayer.

19. The apparatus of claim 11, wherein the ditherer carriage is coupled to a reciprocating lever arm, the lever arm operatively connected at one end thereof to a bearing eccentrically mounted to a pulley, the pulley being driven by a cable.

20. The system of claim 1, the at least one force sensor comprising
- a first force sensor for measuring the insertion forces applied to the working catheter by the ditherer; and
- a second force sensor for measuring the withdrawal forces applied to the working catheter by the ditherer; the system further comprising
- a processor for calculating an estimated force on the distal end of the working catheter based at least in part on the measured forces obtained by the first and second force sensors.

21. The system of claim 20, further comprising a monitor for displaying the estimated force.

22. The system of claim 20, wherein the processor further calculates an error associated with the estimated force.

23. The system of claim 20, further comprising a sheath catheter mounted to the robotic catheter manipulator, the sheath catheter including a lumen therein adapted to receive the guide catheter.

24. The system of claim 20, wherein the working catheter comprises an electrophysiology catheter.

25. The system of claim 20, wherein the working catheter comprises an ablation catheter.

26. The system of claim 20, wherein the reciprocating ditherer is operatively connected to a proximal region of the working catheter via a fluid-tight seal.

27. The system of claim 26, wherein the seal is a Touhy.

28. The system of claim 26, wherein the seal is secured to a proximal end of the guide catheter via a flexible bellows.

29. The system of claim 20, wherein the reciprocating ditherer is operatively connected to a proximal region of the working catheter by a clamp.

30. The system of claim 26, the reciprocating ditherer including a reciprocating carriage containing a pivoting load bearing member, the clamp being positioned on the pivoting load bearing member.

31. The system of claim 26, wherein the reciprocating ditherer is operatively connected to the seal by a clamp.

32. The system of claim 31, the reciprocating ditherer including a reciprocating carriage containing a pivoting load bearing member, the clamp being positioned on the pivoting load bearing member.

33. The system of claim 1, wherein the robotically controlled flexible working catheter is dithered longitudinally back and forth relative to the robotically controlled guide catheter.

34. The system of claim 1, wherein the robotically controlled flexible working catheter is arranged concentrically within the robotically controlled guide catheter and is dithered rotationally relative to the robotically controlled guide catheter.

35. The system of claim 1, wherein a stroke length of the dithered robotically controlled flexible working catheter is less than about 1.5 mm.

36. The system of claim 1, wherein a dither rate of the robotically controlled flexible working catheter is between 0 and about 10 Hz.

\* \* \* \* \*